(12) United States Patent
Matsoukas et al.

(10) Patent No.: US 8,563,586 B2
(45) Date of Patent: Oct. 22, 2013

(54) 1,(3,)5-SUBSTITUTED IMIDAZOLES, THEIR USE IN THE TREATMENT OF HYPERTENSION AND METHODS FOR THEIR PREPARATION

(75) Inventors: John Matsoukas, Patras (GR); Michael Maragoudakis, Patras (GR); Dimitrios Vlaxakos, Athens (GR)

(73) Assignee: Eldrug S.A., Patras (GR)

(*) Notice: Subject to any disclaimer, the term of this patent is extended or adjusted under 35 U.S.C. 154(b) by 644 days.

(21) Appl. No.: 12/601,402

(22) PCT Filed: May 23, 2008

(86) PCT No.: PCT/IB2008/002184
§ 371 (c)(1),
(2), (4) Date: Feb. 1, 2010

(87) PCT Pub. No.: WO2008/142576
PCT Pub. Date: Nov. 27, 2008

(65) Prior Publication Data
US 2010/0166837 A1 Jul. 1, 2010

(30) Foreign Application Priority Data
May 24, 2007 (GR) .............................. 20070100312
Jul. 26, 2007 (GB) .................................. 0714603.8

(51) Int. Cl.
A61K 31/4174 (2006.01)
A61K 31/41 (2006.01)
C07D 257/04 (2006.01)
C07D 233/68 (2006.01)
C07D 233/64 (2006.01)

(52) U.S. Cl.
USPC ........... 514/381; 514/396; 548/254; 548/250; 548/311.1; 548/335.1

(58) Field of Classification Search
USPC ............ 548/250, 254, 311.1, 335.1; 514/381, 514/396
See application file for complete search history.

(56) References Cited

U.S. PATENT DOCUMENTS 5,128,356 A * 7/1992 Naka et al. ..................... 514/381
5,250,554 A * 10/1993 Naka et al. ..................... 514/381
2010/0216854 A1 8/2010 Matsoukas

FOREIGN PATENT DOCUMENTS

| CA | 2092852 A1 | 10/1993 |
| EP | 0 427 463 A1 | 5/1991 |
| EP | 0 564 356 A1 | 10/1993 |
| JP | 06087833 A * | 3/1994 |
| WO | WO 2006/103068 A1 | 10/2006 |

OTHER PUBLICATIONS

Nouet, S. et al., "Specific Nonpeptide Photoprobes as Tools for the Structural Study of the Angiotensin II $AT_1$ Receptor," *J. Med. Chem.*, 1999, 42, pp. 4572-4583.
Tuccinardi, T. et al., "Proposal of a New Binding Orientation for Non-Peptide AT1 Antagonists: Homology Modeling, Docking and Three-Dimensional Quantitative Structure-Activity Relationship Analysis," *J. Med. Chem.* 2006, 49, pp. 4305-4316.
Berge, S.M. et al., "Pharmaceutical Salts," *J. Pharm. Sci.* 1977, 66, pp. 1-19.
Hedner, T. et al., "The efficacy and tolerance of one or two daily doses of eprosartan in essential hypertension," *Journal of Hypertension*, 17, 1999, pp. 129-136.
Adang, A. et al., "Case Histories of Peptidomimetics: Progression from Peptides to Drugs," *J.R. Neth. Chem. Soc.*, 113, 1994, 63-78.
Alexopoulos, K. et al., "Design and Synthesis of Thrombin Receptor-Derived Non-Peptide Mimetics Utilizing a Piperazine Scallold," *Bioorganic and Medicinal Chemistry*, 7, 1999, 1033-1041.
Ashton, W.T., "Nonpeptide Angiotensin II Receptor Antagonists," *Exp. Opin. Invest. Drugs*, 3, 1994, pp. 1105-1142.
Athanasopoulos, C. et al., "*N*-Tritylamino Acids in the Synthesis of Analogs of Bioactive Compounds for Structure-Activity Relationship Studies," *Bioactive Peptides in Drug Discovery and Design: Medical Aspects* J. Matsoukas and T. Mavromoustakos (Eds.) IOS Press, 22, 1999, pp. 137-151.
Athanassopoulos, P. et al., "Application of 2-Chlorotrityl Chloride in Convergent Peptide Synthesis," *Tetr. Lett.*, vol. 36, No. 31, 1995, pp. 5645-5648.
Barlos, K. et al., "9-Fluorenylmethyloxycarbonyl/tbutyl-based convergent protein synthesis," *Biopolymers*, 51 (4), 1999, pp. 266-278.
Barlos, K. et al., "Efficient "one-pot" Synthesis of N-trityl Amino Acids," *J. Org. Chem.*, 47, 1991, p. 1324-1326.
Berecek, K.H. et al., "Angiotensin-Converting Enzyme and Converting Enzyme Inhibitors," *Cellular and Molecular Biology of the Renin-Angiotensin System*,Raizada, MK, Phillips, MI Sumners C. (eds.), *CRC Press*: Boca Raton, FL, 1993, pp. 183-220.
Bottari, S.P. et al., "Angiotensin II Receptor Subtypes: Characterization, Signalling Mechanisms, and Possible Physiological Implications," *Front. Neuroendocrinol.*, 14, 1993, pp. 123-171.
Bottorff, M.B. et al., "Pharmacokinetics of eprosartan in healthy subjects, patients with hypertension and special population," *Pharmacotherapy*, 19, 1999, pp. 73S-78S.
Bovy, P.R. et al., "Influence of Polyfluorination of the Phenylalanine Ring of Angiotensin II on Conformation and Biological Activity," *Biochimica et Biophysica Acta*, 1079, 1991, pp. 23-28.
Bradbury, R.H. et al., New nonpeptide Angiotensin II receptor antagonists, 2 Synthesis, biological properties, and structure-activity relationships of 2-alkyl-4-(biphenylylmethoxy)quinoline derivatives, *J. Med. Chem.*, 35, 1992, pp. 4027-4038.

(Continued)

*Primary Examiner* — Jason M Nolan
(74) *Attorney, Agent, or Firm* — Brinks Hofer Gilson & Lione

(57) ABSTRACT

The present invention provides novel 1,5 and 1,3,5-substituted imidazole compounds in hydrophilic or lipophilic form, which are useful as angiotensin II ATI receptor antagonists suitable for transdermal delivery. The invention also provides pharmaceutical compositions containing such compounds, processes and intermediates for preparing compounds and their use in methods of treating hypertension and cardiovascular diseases.

28 Claims, 1 Drawing Sheet

(56) References Cited

OTHER PUBLICATIONS

Brunner, H.R. et al., Angiotensin blockade for hypertension: a promise fulfilled, *The Lancet*, 359, 2002, 990-992.

Buhlmayer, P., "Angiotensin II Antagonists: Patent Activity since the Discovery of DuP753," *Curro Opin. Ther. Pat.*, 2, 1992, pp. 1693-1718.

Carini, D.J. et al., "Nonpeptide Angiotensin II Receptor Antagonists: The Discovery of a Series of N-(Biphenylmethyl)-imidazoles as Potent, Orally Active Antihypertensives," *J. Med. Chem.*, 34, 1991, pp. 2525-2547.

Carini, D.J. et al., "Nonpeptide Angiotensin II Receptor Antagonists: N-[(Benzyloxy)benzyl]imidazoles and Related Compounds as Potent Antihypertensives," *J. Med. Chem.*, 33, 1990, pp. 1330-1336.

Cheng-Lai, A., "Eprosartan: an angiotensin-II receptor antagonist for the management of hypertension," *Heart Dis.*, 4(1), 2002, pp. 54-59.

Christen, Y. et al., "Oral administration of DuP753, a specific angiotensin II receptor antagonist, to normal male volunteers," *Circulation*, 83, 1991, pp. 1333-1342.

Corvol, P., "New Therapeutic Prospects of Renin-Angiotensin System Inhibition," *Clin. Exp. Hypertens.*, Part A, A11 (Suppl. 2), 1989, pp. 463-470.

Dordor, I.M. et al., "Reaction of Oxazolines with Phosphorus Oxychloride," *Tetrahedron Lett.*, 1983, pp. 1437-1440.

Duncia J.V. et al., "The Discovery of Potent Nonpeptide Angiotensin II Receptor Antagonists: A New Class of Potent Antihypertensives," *Med. Chem.*, 33, 1990, p. 1312-1329.

Duncia J.V. et al., "The Discovery of DuP 753, a Potent, Orally Active Nonpeptide Angiotensin II Receptor Antagonist," *Med. Res. Rev.*, 12, 1992, p. 149-191.

Duncia, J.V. et al., "DuP753 Losartan Potassium (MK-954)," *Drugs Future*, 17, 1992, pp. 326-331.

Duncia, J.V. et al., "The Discovery of Potent Nonpeptide Angiotensin II Receptor Antagonists: A New Class of Potent Antihypertensives." *J. Med. Chem.*, 33, 1990, pp. 1312-1329.

Duncia, J.V. et al., "Three Synthetic Routes to a Sterically Hindered Tetrazole. A New One-Step Mild Conversion of an Amide into a Tetrazole," *J Org. Chem.*, 56, 1991, pp. 2395-2400.

Earle, Martyn J. et al. "Regioselective alkylation in ionic liquids," *Chem. Commun.*, 1998, pp. 2245-2246.

Easthope, S.E. et al., "Candesartan cilexetil: an update of its use in essential hypertension," *Drugs*, 62(8), 2002, pp. 1253-1287.

Ellingboe, J.W. et al., "Metabolites of the angiotensin II antagonist tasosartan: The importance of a second acidic group," *J. Med. Chem.*, 41, 425, 1998, pp. 4251-4260.

Faulhaber, H.D. et al., "Effect of valsartan on renal function in patients with hypertension and stable renal insufficiency," *Current Therapeutic Research—Clinical and Experimental*, 60, 1999, pp. 170-183.

Ferrario, C.M., "The Renin-Angiotensin System: Importance in Physiology and Pathology," *J. Cardiovasc. Pharmacol.*, 15 (3), 1990, pp. 51-55.

Gavras, H. et al., "An angiotensin converting enzyme inhibitor to identify and treat vasoconstrictor and volume factors in hypertensive patients," *N. Engl. J. Med.*, 291, 1974, pp. 817-821.

Gavras, H. et al., "Angiotensin II inhibition: treatment of congestive cardiac failure in a high-renin hypertension," *JAMA*, 238, 1977, pp. 880-882.

Gavras, H. et al., "Anti-hypertensive effect of the oral angiotensin converting-enzyme inhibitor SQ 14225 in man," *N. Engl. J. Med.*, 20, 1978, pp. 298, 991-995.

Gavras, H. et al., "Bioactive Peptides in the Treatment of Hypertension and Heart Failure. Bioactive Peptides in Drug Discovery and Design: Medical Aspects," (Eds.) J. Matsoukas and T. Mavromoustakos, *Biomedical and Health Research*, IOS Press, 22, 1999, pp. 41-50.

Gavras, H. et al., "Effects of specific inhibitor of the vascular action of vasopressin in humans," *Hypertension*, 6 (Suppl 1), 1984, pp. I-156-I-160.

Ghiadoni, L. et al., "Effects of the angiotensin II type 1 receptor blocker candesartan on endothelial function in patients with essential hypertension," *Hypertension*, 35, 2000, 501-506.

Giannis, A. et al., "Peptidomimetics in Drug Design," *Adv. Drug. Res.*, 29, 1997, pp. 1-78.

Gillis, J.C. et al., "Irbesartan. A review of its pharmacodynamic and pharmacokinetic properties and therapeutic use in the management of hypertension," *Drugs*, 54, 1997, pp. 885-902.

Greenlee, W.J. et al., "Hypertension, Treatment by Blockade of the Renin-Angiotensin System," In *Proceedings, XIVth International Symposium on Medicinal Chemistry*, Awouters, F., Eds., Elsevien: Amsterdam, 1997, pp. 97-107.

Karlberg, E. et al., "Efficacy and safety of telmisartan, a selective AT 1 receptor antagonist, compared with enalapril in elderly patients with primary hypertension," *Journal of Hypertension*, 17, 1999, pp. 293-302.

Krambovitis, E. et al., "Preparation of MUC-1 oligomers using an improved convergent solid-phase peptide synthesis," *J Biol Chem.*, 273 (18), 1998, pp. 10874-10879.

Lammek, B. et al., "Synthesis and some pharmacologic properties of five novel V1 or Z1/V2 antagonists of AVP," *Peptides*, 10, 1989, pp. 1109-1112.

Levens, N.R. et al., "Could the Pharmacological Differences Observed Between Angiotensin II Antagonists and Inhibitors of Angiotensin Converting Enzyme be Clinically Beneficial?" *Pharmacol. Toxicol.*, 71, 1992, pp. 241-249.

Lindgren, B.R. et al., "Angiotensin-Converting Enzyme Inhibitors and Their Influence on Inflammation," *Bronchial Reactivity and Cough. Med. Toxicol. Adverse Drug Exp.*, 4, 1989, pp. 369-380.

Maillard, M.P. et al., "Tasosartan, enoltasosartan, and angiotensin II receptor blockade: the confounding role of protein binding," *J. Pharmacol Exp Ther.*, 295(2), 2000, pp. 649-654.

Manolis, A.J. et al., "Combined sympathetic suppression and angiotensin converting enzyme inhibition in congestive heart failure," *Hypertension*, 29 No. 1, (part 2), 1997, pp. 525-530.

Manolis, A.J. et al., "Suppressing sympathetic activation in congestive heart failure," *Hypertension*, 26, 1995, pp. 719-724.

Markham, K.L. Goa, "Valsartan. A review of its pharmacology and therapeutic us in essential hypertension," *Drugs*, 54, 1997, 299-311.

Masek, B.B. et al., "Molecular shape comparison of Angiotensin II receptor antagonists," *J. Med. Chem.*, 36, 1993 pp. 1230-1238.

Matsoukas, J. et al., "$^1$H-NMR Studies of [Sar[1]] Angiotensin II Conformation by Nuclear Overhauser Effect Spectroscopy in the Rotating Frame (ROESY): Clustering of the Aromatic Rings in Dimethylsulfoxide," *Peptides*, 11, 1990, pp. 359-366.

Matsoukas, J. et al., "Novel Synthesis of Cyclic Amidelinked Analogues of Angiotensin II and III," *J. Med Chem.*, 37, 1994, pp. 2958-2969.

Matsoukas, J. et al., "The bioactive conformation of Angiotensin II. The design and synthesis of a potent Angiotensin II cyclic analogue confirms the ring cluster receptor conformation of the hormone," *Bioorg. Med Chem.*, 8, 2000, pp. 1-10.

Matsoukas, J.M. et al., "Differences in Backbone Structure between Angiotensin II Agonists and Type I Antagonists," *J. Med. Chem.*, 38, 1995, pp. 4660-4669.

Matsoukas, J.M. et al., "Importance of the N-terminal domain of the type II angiotensin antagonist Sarmesin for receptor blockade," *J. Med Chem.*, 31, 1998, pp. 1418-1421.

Matsoukas, J.M. et al., "Role of the N-terminal Domain of ANG II and [Sar [1]]ANGII on Conformation and Activity," *J. Biol. Chem.*, 269, 1994, pp. 5303-5312.

Matsoukas, J.M. et al., "Studies of Sarmesin and [Des[1]] Sarmesin conformation in dimethyl sulfoxide by Nuclear Overhauser. Effect (NOE) enhancement spectroscopy: folding of the N- and C-terminal domains," *Peptides*, 11, 1990, pp. 367-374.

Matsoukas, J.M. et al., "Synthesis and biological activities of Angiotensin II, Sarilesin and Sarmesin anologues containing Aze or Pip at postition 7: conformational properties of [Sar[1], Aze[7]] ANG II determined by nuclear overhauser effect (NOE) enhancement spectroscopy," *J. Med. Chem.*, 36, 1993, pp. 904-911.

Matsoukas, J.M. et al., "Synthesis and biological activities of analogues of angiotensin II and III containing O-methyltyrosine and D-tryptophan," *J. Med. Chem.*, 28, 1985, pp. 780-783.

Mavromoustakos, T. et al., "An Effort to Understand the Molecular Basis of Hypertension through the Study of Conformational Analysis of Losartan and Sarmesin Using a Combination of Nuclear Magnetic Resonance Spectroscopy and Theoretical Calculations," *J. Med Chem.*, 42, 1999, pp. 1714-1722.

McAreavey D. et al., "Angiotensin Converting Enzyme Inhibitors and Moderate Hypertension," *Drugs*, 40 (3), 1990, p. 326-345.

McClellan, K.J. et al., Candesartan cilexetil: A review of its use in essential hypertension, *Drugs*, 56, 1998, pp. 847-869.

(56) References Cited

OTHER PUBLICATIONS

Meyers, A.I. et al., "Oxazolines XXII. Nucleophilic Aromatic Substitution on Aryl Oxazolines. An Efficient Approach to Unsymmetrically Substituted Biphenyls and o-Alkyl Benzoic Acids," *J. Am. Chem. Soc.*, 97, 1975, pp. 7383-7385.
Moore, G. et al., "J. Design and Pharmacology of Peptide Mimetics," *Adv. Pharmacol.* (San Diego), 6, 1995, pp. 91-141.
Moore, G.J. et al., "Receptor interactions of the position 4 side chain of angiotensin II analogues: Importance of aromatic ring quadrupole," *J. Mol. Rec.*, 7, 1994, pp. 251-256.
Morsing, P., "Candesartan: A new generation angiotensin II AT1 receptor blocker: Pharmacology, antihypertensive efficacy, renal function, and renoprotection," *Journal of the American Society of Nephrology*, 10, 1999, pp. 8248-8254.
Murphy, T.J. et al., "Isolation of a cDNA Encoding the Vascular Type-I Angiotensin II Receptor," *Nature*, 351, 1991, pp. 233-236.
Neutel, J.M. et al., "The efficacy and safety of telmisartan compared to enalapril in patients with severe hypertension," *International Journal of Clinical Practice*, 53, 1999, pp. 175-178.
Ondetti, M.A, et al., "Design of Specific Inhibitors of Angiotensin-Converting Enzyme: New Class of Orally Active Antihypertensive Agents," *Science*, 196, 1977, p. 441-444.
Ondetti, M.A. et al., "Inhibition of the Renin-Angiotensin System: A New Approach to the Therapy of Hypertension," *J. Med. Chem.*, 24, 1981, pp. 355-361.
Oparil, S. et al., "Tolerability profile of tasosartan, a long-acting angiotensin II ATI receptor blocker, in the treatment of patients with essential hypertension," *Current Therapeutic Research—Clinical and Experimental*, 58, 1997, pp. 930-943.
Page I.H., "In Hypertension Mechanisms," Harcourt Brace Jovanovich, New York, 1987, pp. 347-470.
Plum, J. et al., "Treatment with the angiotensin II antagonist valsartan in patients with chronic renal failure and hypertension," *Nephrology Dialysis Transplantation*, 14, 1999, pp. 25-27.
Polevaya, L. et al., "Design, synthesis and biological evaluation of cyclic angiotensin II analogues with 3,5 side-chain bridges: Role of C-terminal residue and positions 3,5 for activity," In *Drug Discovery and Design: Medical Aspects*, vol. 55, Matsoukas, J., Mavromoustakos, T., Eds., IOS Press: The Netherlands, 2002, pp. 3-12.
Polevaya, L. et al., "Synthesis and Study of a Cyclic Angiotensin II Antagonist Analogue Reveals the Role of $\pi^*$-$\pi^*$ Interactions in the C-terminal Aromatic Residue for Agonist Activity and its Structure Resemblance with ATI Non-peptide Antagonists," *Bioorg. Med Chem.*, 9, 2001, pp. 1639-1647.
Rabbat, C.G., "Irbesartan was renoprotective in patients with type 2 diabetes, hypertension, and microalbuminuria," *ACP J Club.*, 136(3), 2002, pp. 82-84.
Rheaume, P.H. et al., "Effects of angiotensin antagonism with tasosartan on regianal and systemic haemodynamics in hypertensive patients," *Journal of Hypertension*, 16, 1998, pp. 2085-2089.
Rippin, J. et al., "Rationale and design of diabetics exposed to telmisartan and enalapril (DETAIL) study," *J Diabetes Complications*, 16(3), 2002, pp. 195-200.
Roumelioti, P. et al., "Design, Synthesis and Biological Evaluation of Cyclic Angiotensin II Analogues with 3, 5 Side-Chain Bridges: Role of C-Terminal Aromatic Residue and Ring Cluster for Activity and Implications in the Drug Design of ATI Non Peptide Antagonists," *Bioorg Med Chem.*, 12, 2002, pp. 2627-2633.
Roumelioti, P. et al., "Structural Comparison Between Type I and Type II Antagonists: Possible Implications in the Drug Design of ATI Antagonists," *Bioorg. and Med. Chem. Letters*, 10, 2000, pp. 755-758.
Sasaki, K. et al., "Cloning and Expression of a Complementary DNA Encoding a Bovine Adrenal Angiotensin II Type-I Receptor," *Nature*, 1991, pp. 230-233.
Sealey, J.E. et al., "The Renin-Angiotensin-Aldosteronie System for Normal Regulation of Blood Pressure and Sodium and Potassium Homeostasis," In *Hypertension: Pathophysiology, Diagnosis and Management*, Laragh, J.H., Brenner, B.M., Eds., Raven Press: New York, 1990, pp. 1287-1317.
Shusterman, N. H., "Safety and efficacy of eprosartan, a new angiotensin II receptor blocker," *American Heart Journal*, 138, 1999, pp. S238-S245.
Sica, D.A., "Review of eprosartan: A new angiotensin II receptor antagonist: Summary," *Pharmacotherapy*, 19, 1999, pp. 108S-109S.
Simon, T.A. et al., "Safety of irbesartan in the treatment of mild to moderate systemic hypertension," *The American Journal of Cardiology*, 82, 1998, pp. 179-182.
Smith, J. et al., "Advances in Antihypertensive Therapy: Non-Peptide Angiotensin II Receptor Antagonists as Potent Therapeutic Agents," *Letters in Peptide Science (LIPS)*, 3, 1996, pp. 169-174 (Guest Editor of Special Issue).
Stoukides, A. et al., "Candesartan cilexetil: an angiotensin II receptor blocker," *Annals of Pharmacology*, 33, 1999, pp. 1287-1298.
Theodoropoulou, E. et al., "Superimposition of potent non-peptide ATI receptor antagonists with Angiotensin II," *Lett. Pept. Sci.*, 3, 1996, pp. 209-215.
Thurmann, P.A. et al., "Influence of the angiotensin II antagonist valsartan on left ventricular hypertrophy in patients with essential hypertension," *Circulation*, 98, 1998, pp. 2037-2042.
Timmermans P.B.M.W.M. et al., "Nonpeptide angiotensin II receptor antagonists," *Trends Pharmacol. Sci.*, 12, 1991, pp. 55-62.
Timmermans, P.B.M.W.M. et al., "In Hypertension: Pathophysiology, Diagnosis and Management," Raven Press: New York, 235, 1990, pp. 2351-2360.
Timmermans, P.B.M.W.M. et al., "Nonpeptide Angiotensin II Receptor Antagonists," *Am. J. Hypertens.*, 3, 1990, pp. 599-604.
Timmermans, P.B.M.W.M. et al., "Angiotensin II Receptors and Angiotensin II Receptor Antagonists," *Pharmacol. Rev.*, 45, 1993, pp. 205-251.
Turner, R.J. et al., "Fluorescence properties of Angiotensin II analogues in receptor-simulating invironments: relationship between tyrosinate fluorescence lifetime and biological activity," *Biochim. Biophys. Acta*, 1065, 1991, pp. 21-28.
Turner, R.J. et al., "Tyrosinate Flyorescence Life Times for Oxytocin and Vasopressin in Receptor Simulating Environments: Relationship to Biological Activity and IH-NMR Data," *Bioch. Bioph. Res. Commun.*, 171, 1990, pp. 996-1001.
Van Meel, J.C.A. et al., "Hypotensive effects of the angiotensin II antagonist telmisartan in conscious chronically-instrumented transgenic rats," *Arzn.-Forsch. / Drug Research*, 46, 1996, pp. 755-759.
Man in't Veld, et al., "Clinical overview of irbesartan: Expanding the therapeutic window in hupertension," *Journal of Hypertension, Supplement*, 15, 1997, pp. S27-S33.
Vlahakos, D.V. et al., "Association Between Activation of the Renin-Angiotensin System and Secondary Erythrocytosis in Patients With Chronic Obstructive Pulmonary Disease," *Am J Med.*, 106(2), 1999, pp. 158-164.
Vlahakos, D.V. et al., "Biological Activity of the Novel Cyclic Angiotensin II Analogues [Sar$^1$, Lys$^3$, Glu$^5$] ANG II," *Letters in Peptide Science (LIPS)*, 3, 1996, pp. 191-194.
Wahhab, A. et al., "Imidazole Based Non-Peptide Angiotensin II Receptor Antagonists," *Arzn.-Forsch./Drug Research*, 43(1), 11, 1993, pp. 1157-1168.
Waeber, B. et al., "Angiotensin-Converting-Enzyme Inhibitors in Hypertension," In *Hypertension: Pathophysiology, Diagnosis and Management*, Laragh, J.H., Brenner, B.M., Eds., Raven Press: New York, 1990, pp. 2209-2232.
Waeber, B., "Blood pressure control: A review on irbesartan," *European Heart Journal*, Supplements, 2, (Supplemental B), 2000, pp. B2-B7.
Wexler, R.R. et al., "Nonpeptide Angiotensin II receptor antagonists: the next generation in antihypertensive therapy," *J. Med. Chem.*, 39, 1996, pp. 625-655.
Jones, J.B. et al., "Alkylations of the Side-chain Nucleophiles of Cysteine, Methionine, Histidine, and Lysine Derivatives with Allyl Bromide, 1-Bromo-2-butyne, and 2-Bromoacetophenone," *Canadian Journal of Chemistry* 49, (1971), pp. 3012-3019.

\* cited by examiner

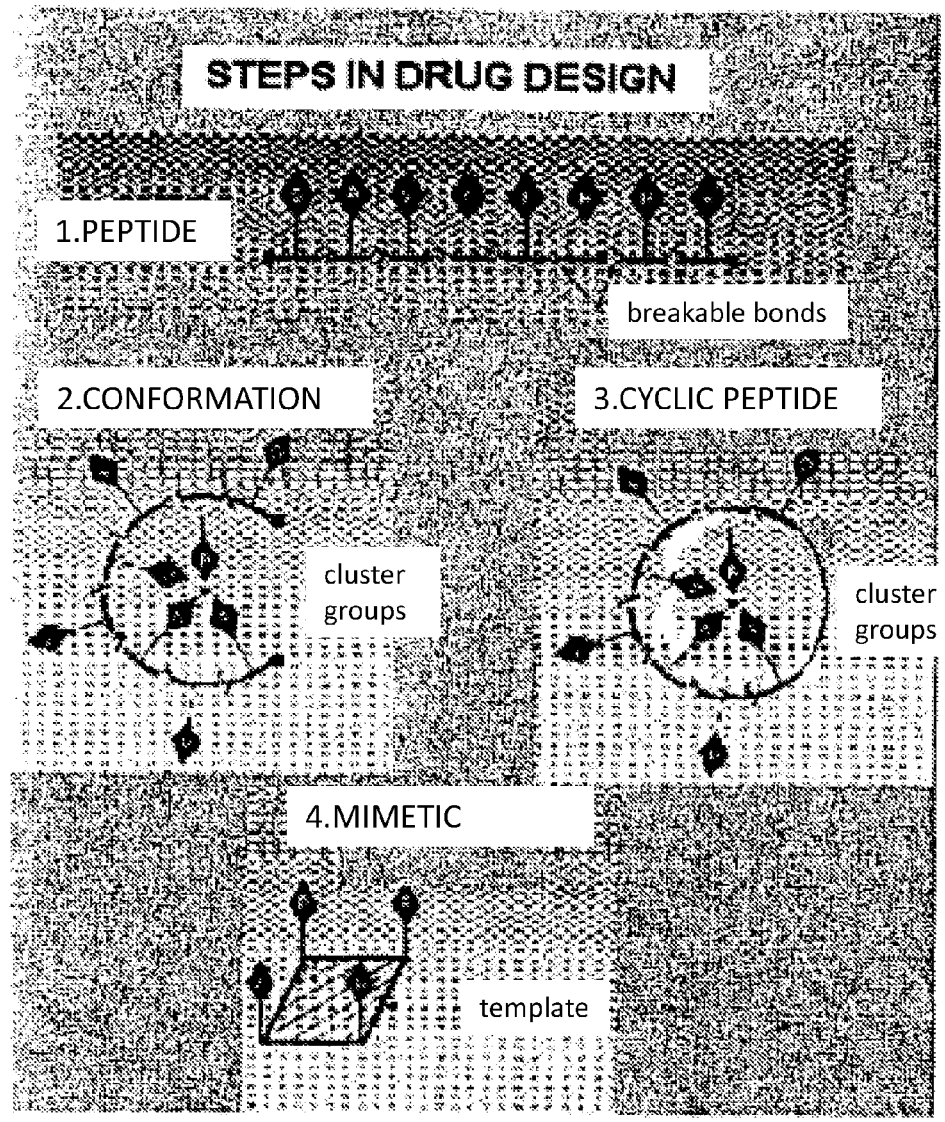

1,(3,)5-SUBSTITUTED IMIDAZOLES, THEIR USE IN THE TREATMENT OF HYPERTENSION AND METHODS FOR THEIR PREPARATION

CROSS REFERENCE TO RELATED APPLICATIONS

This application claims priority to PCT/IB2008/002184, filed May 23, 2008, which application claims priority to GR 20070100312, filed May 24, 2007 and GB 0714603.8, filed Jul. 26, 2007.

The present invention relates to 1,5- and 1,3,5-substituted imidazole derivatives. The compounds are useful as angiotensin II AT1 receptor antagonists and have therapeutic applications in the treatment of hypertension and other cardiovascular disorders. The invention further relates to a synthetic route for preparing the claimed derivatives.

BACKGROUND TO THE INVENTION

The renin-angiotensin system (RAS) plays a key role in regulating cardiovascular homeostasis and electrolyte/fluid balance in normotensive and hypertensive subjects.[1-6] Angiotensin II (AII), an octapeptide that is formed within the RAS from angiotensin I by angiotensin-converting enzyme (ACE), is one of the most powerful vasoconstrictors known. AII was also found to be a growth factor implicated in cardiac, vascular hypertrophy and ventricular remodeling following myocardial infarction. Consequently, the RAS has been a prime target for the therapy of cardiovascular diseases. Reducing the levels of AII by inhibition of ACE is a good approach for treating hypertension, confirmed by the success of ACE inhibitors as antihypertensives. However, due to the fact that ACE inhibitors may increase the levels of bradykinin and cause side effects such as dry cough and angioedema (as do some AII antagonists), drugs that can antagonize AII at its receptor sites have been considered a more specific approach to blockade of the RAS. Although peptide analogues of AII such as sarilesin and sarmesin inhibit the action of AII by competitively binding to the receptor, their application as clinical agents is limited due to their short duration of action, poor bioavailability and partial agonist activity. However, these AII type I and type II30 antagonists have been valuable tools in our hands for identifying pharmacophoric groups and for the design of AII non-peptide mimetics. The discovery by DuPont of the first potent and orally active non-peptide AII antagonist Losartan has stimulated extensive research interest in this area. Several patents and publications have appeared over the past few years describing new AII receptor antagonists including Candesartan, Irbesartan, Valsartan, Telmisartan, Tasosartan and Eprosartan, which have been proven safe and effective in the treatment of hypertension and other cardiovascular disorders.

Our work has been focused in recent years on the study of the conformational analysis of the peptide hormone AII, the competitive antagonist sarmesin as well as other cyclic peptide derivatives. Comparative studies of sarmesin with AT1 receptor antagonists possessing different anti-hypertensive efficacies gave clues about the relation between conformation and bioactivity.

(A) Angiotensin I Receptor Antagonists: the Role of Negative Charges and Alkyl or Ester/Carboxyl Groups at Position 5 of Imidazole Angiotensin II is an octapeptide hormone (Asp-Arg-Val-Tyr-Ile-His-Pro-Phe) which is a powerful arterial vasoconstrictor that exerts its action by interacting with specific receptors present on cell membranes. Blockade of the actions of angiotensin II using angiotensin receptor antagonists is useful for the treatment of hypertension and congestive heart failure and other cardiovascular and related diseases such as diabetic nephropathy. Pioneering work based on modifications of the peptide structure of ANG II led to potent modified peptides (Sarilesin, Saralasin, Sarmesin) that showed potent and selective in vitro ANG II receptor antagonism. However, the action of such agents in vivo was severely diminished by their rapid metabolism to inactive compounds. Thus, the search was on to identify and develop a non-peptide ANG II receptor antagonist that was both resistant to the metabolic deactivation of peptide antagonists and selective for the ANG II receptor.

In 1982, Takeda (Japan) filed a patent application disclosing the discovery of non-peptide ANG II receptor antagonists. The activity of these initial compounds was low but showed good selectivity. In subsequent years, much detailed knowledge was obtained through work on modified peptides, and DuPont engaged in extensive studies to exploit Takeda's early lead. These efforts were rewarded with the development of DuP753 (Losartan), which is now used to treat various hypertensive conditions. The antihypertensive activity of Losartan is largely due to a long-acting metabolite (EXP 3174) which is produced in vivo as a result of the conversion of hydroxymethyl to carboxylate, providing a negative charge required for affinity. Likewise, valsartan (CGP 48933) is a potent angiotensin receptor antagonist containing a carboxylate group analogous to that in EXP 3174. Indeed, a common feature of EXP 3174, CGP 48933 and another angiotensin mimetic SK 108566, is the presence of two acid groups spaced at similar distances on various aromatic templates.

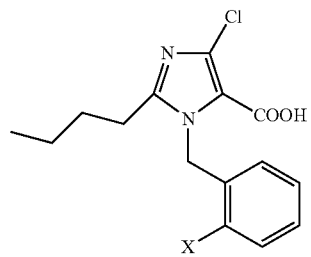

S-8307: X = Cl
S-8308: X = $NO_2$
Takeda

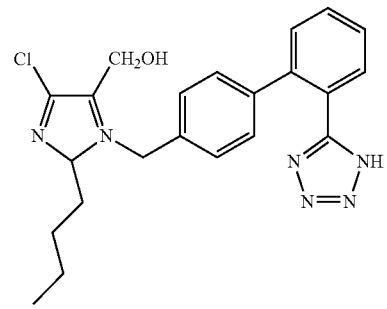

Losartan
(COZAAR, DuP 753, MK-954)

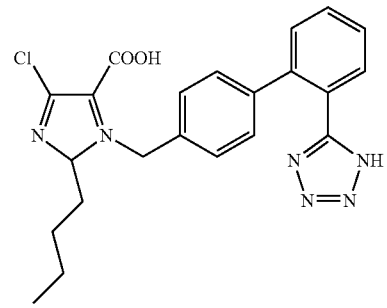

EXP 3174

Many other companies have sought to develop their own angiotensin mimetics in a bid to compete for a share in the huge worldwide market for antihypertensive drugs. From these molecules seven antagonists are in the market. Valsartan is the second molecule after Losartan to reach the market, while Irbersartan, Eprosartan, Candesartan, Telmisartan, Tasosartan and Olmesartan 10 followed the pipeline.

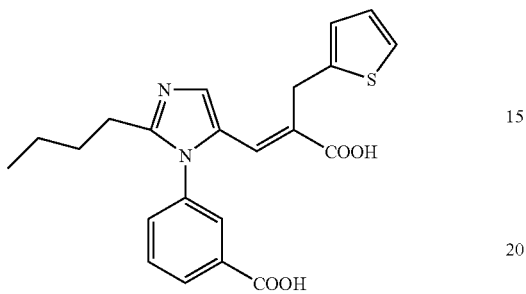

EPROSARTAN
SKB

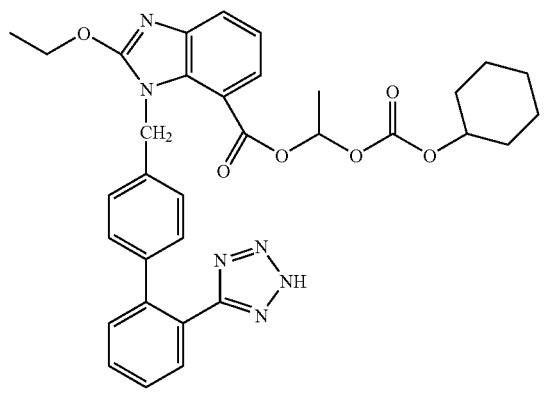

CANDESARTAN
AZ

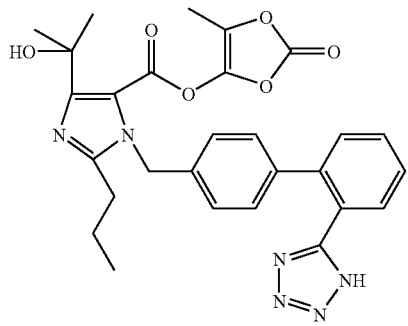

OLMESARTAN
Menarini

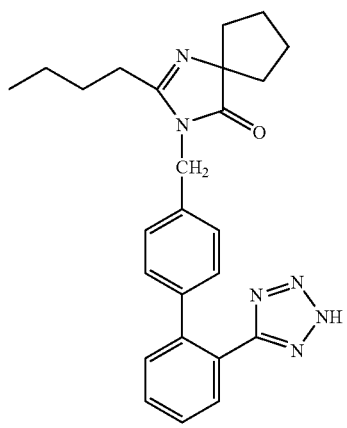

IRBESARTAN
BMS

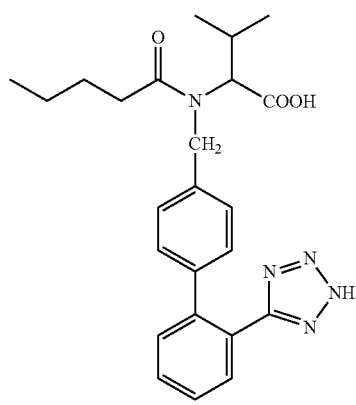

VALSARTAN
Eli Lilly

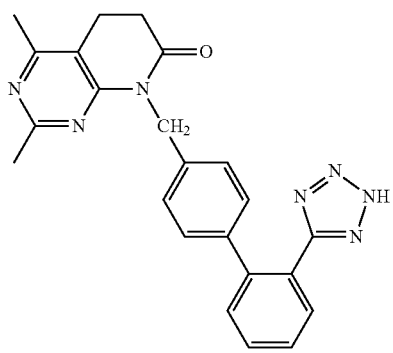

TASOSARTAN
Wyeth, AYIRST

-continued

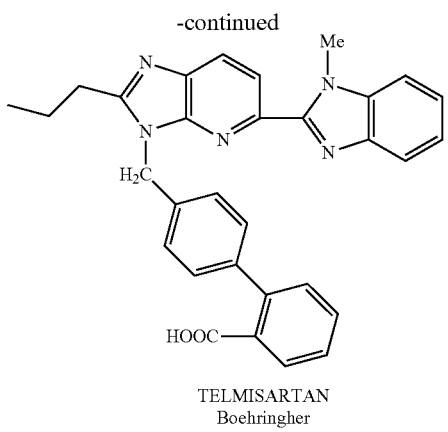

TELMISARTAN
Boehringher

Inhibitors of Angiotensin in the Market

Reorientation of the imidazole ring of Losartan with relocation of butyl (aliphatic) and $CH_2OH$-groups provided novel compounds useful in treating hypertension in anesthetized rats and rabbits. Based on a survey of four of the possible five orientations of the imidazole ring of Losartan, it was observed that compounds in which the biphenyl moiety is attached to an imidazole N atom, rather than one of the C atoms of the heterocyclic ring, have the highest activity. With this knowledge, we developed a series of compounds in an attempt to attain the high biological activities observed for Losartan itself. Transposition of the substituents at 2 and 5-positions of the imidazole ring of Losartan has provided compounds with significant activities in vitro when examined in the rat isolated uterus assay and anesthetized rabbits. Further protection of tetrazole by protecting groups as Trt, Cl-Trt, Benzyl and derivatives increased lipophilicity and furthermore the duration of the activity in anesthetized rats and rabbits. Lipophilic compounds were effective to reduce blood pressure in animal models by transdermal delivery.

With the exception of Eprosartan, the majority of the above non-peptide antagonists are based on modifications to one or more fragments of Losartan. Thus, there are a number of structural similarities between the compounds on the market.
(a) they generally have a biphenyl scaffold;
(b) the first phenyl ("spacer") is connected with a nitrogen heterocycle and the second phenyl ("terminal") with an acidic group such as carboxylic group, tetrazole, sulfonylurea, triflamide or substituted sulfonamide;
(c) most heterocycle rings attached to biphenyl tetrazole (BPT) possess adjacent groups like carboxy groups, basic nitrogen moieties, lactam oxygens that allow hydrogen-bonding to the corresponding acceptor;
(d) all molecules possess an alkyl chain attached to heterocycle; these alkyl chains are believed to fit a lipophilic pocket in the AT1 receptor.

(B) Skin Delivery of Drugs

The most widely used routes for the administration of a drug to patients is either by providing it as a pill by mouth (per os) or by directly delivering it as an intramuscular or intravenous injection. However, lipophilic molecules can be delivered through the skin, as has been the case in various dermatologic remedies. In fact, besides the usual nutritive vessels, such as arteries, capillaries and veins, skin contains an extensive subcutaneous venous plexus, which can hold large quantities of blood. By delivering medications through the skin directly into the veins, one can bypass portal circulation and eliminate first pass metabolism in the liver, therefore eliminating side effects from active metabolites.

In addition to dermatologic preparations, other systemic drugs have been developed as transdermal patches. For example, the first transdermal nitroglycerine patch obtained FDA approval in 1981 and gained wide acceptance for its convenience. More recently, the transdermal formulation of oxybutynin was approved by FDA in 2003. As shown in the following Table, at least 8 different categories of drugs are currently manufactured as transdermal patches and they are used for slow, constant and prolonged release of their respective medication through the skin.

| Medication | Indication |
|---|---|
| Nitroglycerine | Chest pain due to coronary artery disease |
| Clonidine | High blood pressure, opioid withdrawal |
| Estrogens/Progesterone | Contraception |
| Testosterone | Male hypogonadism |
| Nicotine | Smoking Cessation |
| Scopolamine | Vertigo, motion sickness |
| Oxybutinin | Bladder overactivity |
| Fentanyl | Cancer pain |

Transdermal nitroglycerine patches have been used for many years to prevent angina pectoris (exercise-induced chest pain due to coronary artery disease). Those patches either have a polymer matrix or a silicone gel impregnated with nitroglycerine. A semipermeable membrane between the drug reservoir and the skin results in a constant delivery of nitroglycerine. The onset of action is within 30 minutes, and the peak effect is seen in 60-180 minutes, with a duration of action of 8-14 hours.

Catapres-TTS is a multilayered film, 0.2 mm thick, containing clonidine as the active agent. To date, this formulation is the only one providing antihypertensive medication through the skin. In addition, clonidine patches have been used to decrease withdrawal symptoms in patients taking opioids. The amount of drug delivered is directly proportional to the size of the patch used. There are four layers: (a) a backing layer of polyester film, (b) a drug reservoir of clonidine, mineral oil, polyisobutylene and colloid silicon dioxide, (c) a microporous polypropylene membrane that controls the rate of delivery of clonidine and (d) an adhesive formulation. The patch is programmed to release clonidine at constant rate for 7 days. Allergic contact sensitisation is observed in 5% of patients.

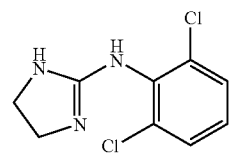

Structure of Clonidine

Ortho Evra developed a transdermal contraceptive patch for providing hormonal contraception. Each patch delivers 20 g of ethinyl estradiol and 150 g of norelgestonin daily. The patch is changed once a week. In randomized studies the contraceptive efficacy of the patch was similar to that of oral contraceptives, but the compliance was significantly better with the patch. Discontinuation of the patch due to reaction at the site of application occurred in 1.9% of the women.

Transdermal delivery of testosterone first became available in 1994, as a scrotal patch. Since then more testosterone patches have been developed for the bare skin. Their major advantage is maintenance of stable serum testosterone concentration in the majority of patients. Testosterone can be also delivered through the skin a hydroalcoholic gel preparation approved by FDA in 2000. The only indication for their use is as replacement therapy in male hypogonadism.

Transdermal nicotine systems can deliver nicotine at several dosages and have been used for smoking cessation. Randomized studies have revealed that nicotine patches at higher dosage range associated with behavioral intervention may double the quitting rates when compared with behavioral intervention alone.

Scopolamine patches have been used to prevent motion sickness, as preoperative medication or to decrease excessive motility of the genitourinary or gastrointestinal tract. Scopolamine patches should be applied behind the ear 2-3 hours before anticipated need. They can deliver up to 1 mg of scopolamine over 3 days.

Oxybutynin relaxes bladder smooth muscles by blocking the muscarinic receptors and has been used in patients with bladder overactivity (urge urinary incontinence, frequency, nocturia). A transdermal formulation of oxybutynin was approved by FDA in 2003. Randomized studies have shown that transdermal oxybutynin was as effective as per os formulations, but direct delivery of the drug into the skin veins was associated with a lower incidence of dry mouth. Local pruritus was seen in 14% of patients using oxybutynin patches versus in 4% with placebo.

Fentanyl is the only opioid prepared for transdermal use in patients with cancer pain. The onset of analgesia is 12-14 hours from patch application and analgesia continues for 16-24 hours after removal of the patch.

Non-Peptide Mimetics of Angiotensin: from Peptides to Cyclic and Non-Peptide Mimetics of Angiotensin The methodology to transfer angiotensin to its non-peptide mimetic antagonist includes the following steps: a) The Peptide (The tool), b) The Peptide Model (The Ligand-Receptor Interaction), c) The Cyclic Peptide (the Drug Lead) and d) the Non-Peptide Mimetic (the Drug).

The methodology to transfer angiotensin to its non-peptide mimetic antagonist is shown graphically in FIG. 1.

a) Peptide (the Tool)

Angiotensin II is consisting of eight aminoacids. Structure-activity studies have revealed the importance of residues $Arg^2$, $Tyr^4$, $His^6$, $Phe^8$ and the C-terminal carboxylate for activity. Peptide antagonists such as Sarilesin and Sarmesin cannot be used as drugs against hypertension due to metabolic degradation. Therefore the peptide hormone angiotensin can be used only as a tool to design non-peptide mimetics as drugs.

b) Peptide Model (the Ligand-Receptor Interaction)

Conformational Model

In 1994 a model was developed of angiotensin II which involves an aromatic ring cluster and consequently a charge relay system formed from the triad of aminoacids $Tyr^4$-$His^6$-$Phe^8$. These three aminoacids are a strict requirement for angiotensin II to exert its agonist activity. Comparative nuclear magnetic resonance studies of the backbone structure between peptide agonists and antagonists have shown that agonists display ring clustering and form a change relay system. Such clustering is also present in the competitive antagonist $Tyr(Me)^4$ ANG II (Sarmesin) which lacks the potential of the charge relay system and the form of the tyrosinate anion which is a strict requirement for agonist activity in the proposed model. In addition, the proposed conformation of ANG II overlays the recently discovered nonpeptide ANG II receptor antagonist EXP-3 174 and its analogs when molecular modeling techniques and superimposition studies are applied. Finally, the ring cluster conformation is supported by the design and synthesis of a novel constrained ANG II cyclic analogue [$Sar^1$, $Lys^3$, $Glu^5$] ANG II, which possesses agonist activity when tested in the rat uterus assay and in anesthesized rabbits. This potent cyclic analog was designed with the integrity of the ring cluster as a major molecular feature. Based on structure activity relationships which demand the presence of Phe, Tyr and His for ANG II to possess biological activity, it can be inferred that the ability to form a ring cluster, and consequently a charge relay system, may be the key stereoelectronic molecular features of ANG II for exerting biological activity.

Theoretical calculations improved further the model and the revised one includes electrostatic interactions between $Asp^1$-$Arg^2$ and $Arg^2$-$Tyr^4$.

$Asp^1$-$Arg^2$-$Val^3$-$Tyr^4$-$Ile^5$-$His^6$-$Pro^7$-$Phe^8$

Angiotensin II

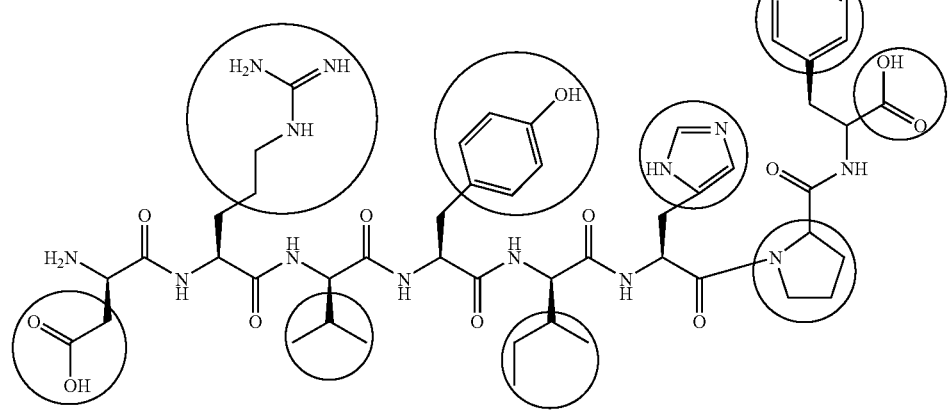

c) Cyclic Peptide (the Drug Lead)

Of all cyclic structures shown, only Cyclo (3-5) [Sar$^1$, Glu$^3$, Lys$^5$] ANG II retains the ring cluster, i.e. the Phe, Tyr, His side chains on the same plane show biological activity. Cyclo (3-5) [Sar$^1$, Glu$^3$, Lys$^5$, Ile$^8$] ANG II, as expected according to the model, shows antagonist activity. All others are inactive as the integrity of cluster is lost.

cyclo(1-8) ANG II cyclo(3-5) [Sar1-Glu3-Lys5-Ile8] ANG II cyclo(1-8) [Acp1] ANG II cyclo(1-8) [Sar1] ANG II Des1,2,3cyclo(4-8) ANG II

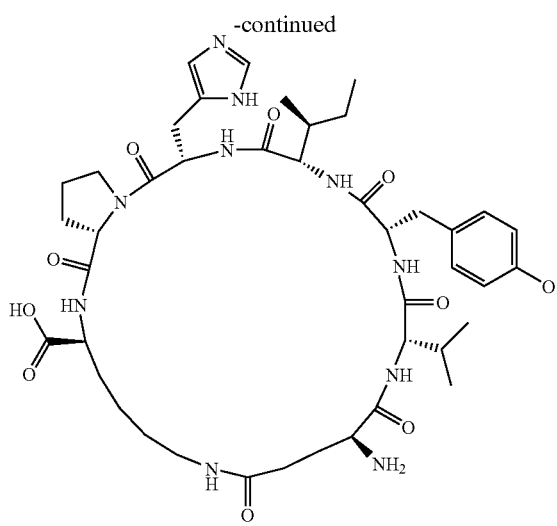

Des1cyclo(2-8) (Glu2, Lys8) ANG II

Angiotensin II Cyclic Peptides d) Non-Peptide Mimetic (the Drug)

Based on computer assisted modeling studies in which the side chains of histidine, tyrosine, and phenylalamine (i.e. imidazole, phenol, phenylalanine) and an acid group like tetrazole or COOH are required for activity, the present invention provides compounds of the following formula:

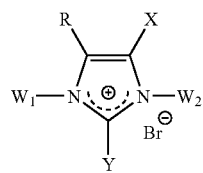

More specifically, the present invention seeks to provide novel 1,5- and 1,3,5-substituted imidazole derivatives that are useful as angiotensin II AT1 receptor antagonists and have therapeutic applications in the treatment of hypertension and other cardiovascular disorders. More specifically, but not exclusively, the present invention seeks to provide lipophilic (monoalkylated and dialkylated) 1,5- and 1,3,5-substituted imidazoles that are suitable for transdermal administration.

STATEMENT OF INVENTION

A first aspect of the invention relates to a compound of formula I,

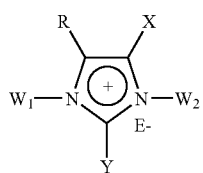

wherein
R is H, halogen;
X is alkyl, alkenyl, —$(CH_2)_v$COOR$^1$ or CH=CH—$(CH_2)_v$ COOR$^1$, where v is 0 to 10; or
R and X are linked so as to form a fused benzimidazole system;
R$^1$ is H, alkyl, aralkyl, trityl, halogen, haloalkyl, cycloalkyl, alkenyl, alkynyl, alkoxyalkyl, haloalkoxyalkyl, alkoxy, aryloxy alkoxyalkoxy, cyano, hydroxy, hydroxyalkyl, nitro, tetrazolyl, oxadiazolyl, triazolyl, OCH(CH$_3$)—OCOO-cyclohexyl, cycloanhydride or methyl-5-methyl-[1,3]-dioxolane;
Y is H, CH$_2$O-alkyl, CH$_2$S-alkyl, CH$_2$-halogen, CH$_2$OH, CH$_2$SH, CHO, COOH or halogen;
W$_1$ and W$_2$ are each independently —$(CH_2)_n$—K—Z—Z$_1$, where n is 1 to 5;
K is biphenyl or monophenyl;
Z is tetrazolyl or COO—;
Z$_1$ is H, trityl, halotrityl, CH$_2$Ph, COOH, COO-alkyl or CH(Ph)$_2$, wherein each Ph group is optionally substituted by one or more halogens; and
E is an anion;
or a pharmaceutically acceptable salt thereof.

A second aspect of the invention relates to a compound of formula II or formula III,

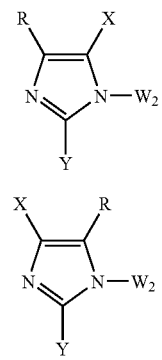

wherein
R is H, halogen;
X is alkenyl, —$(CH_2)_v$COOR$^1$ or CH=CH—$(CH_2)_v$ COOR$^1$, where v is 0 to 10; or
R and X are linked so as to form a fused benzimidazole system; or
X is alkyl, when Z$_1$ is halotrityl, COOH, COO-alkyl, CH$_2$(C$_6$H$_4$-Hal) or CH(Ph)$_2$, wherein each Ph group is optionally substituted by one or more halogens;
R$^1$ is H, alkyl, aralkyl, trityl, halogen, haloalkyl, cycloalkyl, alkenyl, alkynyl, alkoxyalkyl, haloalkoxyalkyl, alkoxy, aryloxy alkoxyalkoxy, cyano, hydroxy, hydroxyalkyl, nitro, tetrazolyl, oxadiazolyl, triazolyl, OCH(CH$_3$)—OCOO-cyclohexyl, cycloanhydride or methyl-5-methyl-[1,3]-dioxolane;
Y is H, CH$_2$O-alkyl, CH$_2$S-alkyl, CH$_2$-halogen, CH$_2$OH, CH$_2$SH, COOH, halogen or CHO;
W$_1$ is —$(CH_2)_n$—K—Z—Z$_1$, where n is 1 to 5;
K is biphenyl or monophenyl;
Z is tetrazolyl or COO—; and
Z$_1$ is H, trityl, halotrityl, CH$_2$Ph, COOH, COO-alkyl, or CH(Ph)$_2$, wherein each Ph group is optionally substituted by one or more halogens;
or a pharmaceutically acceptable salt thereof.

A third aspect of the invention relates to a pharmaceutical composition comprising a compound of the invention admixed with a pharmaceutically acceptable diluent, excipient or carrier.

A fourth aspect of the invention relates to the use of a compound of the invention, or a pharmaceutically acceptable salt thereof, in the preparation of a medicament for treating hypertension or a cardiovascular disorder.

A fifth aspect of the invention relates to a compound as defined above for use in medicine.

A sixth aspect of the invention relates to a method of treating hypertension or a cardiovascular disorder in a subject, said method comprising administering to the subject a therapeutically effective amount of a compound of the invention, or a pharmaceutically acceptable salt thereof.

A seventh aspect of the invention relates to a process for preparing compounds of the invention. Specifically, the invention provides a more efficient process in contrast to prior art methods which involved a multistep, poorly efficient synthetic strategy. In particular, the invention provides optimized synthetic strategies leading to key 1,5-imidazole scaffolds as drug leads. A general and selective alkylation protocol has been developed which facilitates the synthesis of 1,5-disubstituted imidazoles by selective alkylation of N-1 imidazole nitrogen of 4(5)-butylimidazole where the N-3 imidazole nitrogen is temporarily protected by trityl group. Clean and selective alkylation of N-1 position with bromides that bear different pharmacophoric groups at the biphenyl moiety offers a strong SAR tool to optimize structure.

DETAILED DESCRIPTION

As mentioned above, a first aspect of the invention relates to compounds of formula I or formula II or formula III as defined above which have therapeutic applications as angiotensin II receptor antagonists.

In particular, the invention includes the synthesis of angiotensin II receptor antagonists which have one or more of the following:
(1) the alkyl (butyl) group of Losartin is replaced by an ester or carboxyl group to add another negative charge required for higher affinity compared to known non-peptide angiotensin II antagonists;
(2) the —$CH_2OH$ and butyl (or ester/carboxyl replacement thereof) groups are reversed in the imidazole ring compared to Losartan; and/or
(3) the tetrazole group is protected by trityl moieties or benzyl derivatives to increase lipophilicity and length of action.

Specifically, the present invention uses urocanic acid which is the basis for the synthesis of Losartan analogues in which butyl and hydroxymethyl groups are reversed. In urocanic acid based analogues, this reversion is retained while the butyl group is replaced by propanoic acid (or its ester) or propene-oic acid (or its ester) group. Introduction of carboxyl or ester group enhances the affinity of analogue for its receptor and increases inhibitory effect compared to analogues with butyl group. Furthermore, urocanic acid as starting material allows the cost effective synthesis of potent AT1 antagonists through 1,5-disubstituted imidazoles in four high yielding steps. Conversion of hydrophilic compounds to lipophilic compounds by esterification of the carboxyl group and tritylation of tetrazole group allows transdermal delivery.

In one embodiment, the invention relates to a compound of formula I,

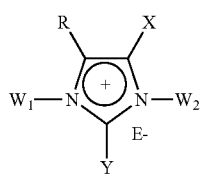

wherein
R is H, halogen;
X is alkyl, alkenyl, —$(CH_2)_v COOR^1$ or $CH=CH—(CH_2)_v COOR^1$, where v is 0 to 10; or
R and X are linked so as to form a fused benzimidazole system;
$R^1$ is H, alkyl, aralkyl, trityl, halogen, haloalkyl, cycloalkyl, alkenyl, alkynyl, alkoxyalkyl, haloalkoxyalkyl, alkoxy, aryloxy alkoxyalkoxy, cyano, hydroxy, hydroxyalkyl, nitro, tetrazolyl, oxadiazolyl, triazolyl, $OCH(CH_3)$— OCOO-cyclohexyl, cycloanhydride or methyl-5-methyl-[1,3]-dioxolane;
Y is H, $CH_2$O-alkyl, $CH_2$S-alkyl, $CH_2$-halogen, $CH_2OH$, $CH_2SH$, CHO, COOH or halogen;
$W_1$ and $W_2$ are each independently —$(CH_2)_n$—K—Z—$Z_1$, where n is 1 to 5;
K is biphenyl or monophenyl;
Z is tetrazolyl or COO—;
$Z_1$ is H, trityl, halotrityl, $CH_2Ph$, COOH, COO-alkyl or $CH(Ph)_2$, wherein each Ph group is optionally substituted by one or more halogens; and
E is an anion;
or a pharmaceutically acceptable salt thereof.

As used herein, the term "alkyl" includes both saturated straight chain and branched alkyl groups. Preferably, the alkyl group is a $C_{1-20}$ alkyl group, more preferably a $C_{1-15}$, more preferably still a $C_{1-12}$ alkyl group, more preferably still, a $C_{1-6}$ alkyl group, more preferably a $C_{1-3}$ alkyl group. Particularly preferred alkyl groups include, for example, methyl, ethyl, propyl, isopropyl, butyl, isobutyl, tert-butyl, pentyl and hexyl.

As used herein, the term "cycloalkyl" refers to a cyclic alkyl group. Preferably, the cycloalkyl group is a $C_{3-12}$ cycloalkyl group.

As used herein, the term "aryl" refers to a substituted (mono- or poly-) or unsubstituted monoaromatic or polyaromatic system, wherein said polyaromatic system may be fused or unfused. Preferably, the term "aryl" is includes groups having from 6 to 10 carbon atoms, e.g. phenyl, naphthyl etc. The term "aryl" is synonymous with the term "aromatic".

The term "aralkyl" is used as a conjunction of the terms alkyl and aryl as given above. Preferred aralkyl groups include $CH_2Ph$ and $CH_2CH_2Ph$ and the like.

One preferred aspect of the invention relates to a compound of formula I or II,

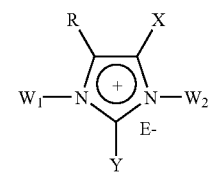

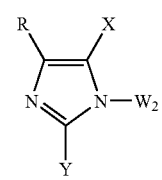

wherein
R is H, halogen;
X is alkyl, alkenyl, —$(CH_2)_v COOR^1$ or $CH=CH—(CH_2)_v COOR^1$, where v is 0 to 10; or
R and X are linked so as to form a fused benzimidazole system;

R[1] is H, alkyl, aralkyl, trityl, halogen, haloalkyl, cycloalkyl, alkenyl, alkynyl, alkoxyalkyl, haloalkoxyalkyl, alkoxy, aryloxy alkoxyalkoxy, cyano, hydroxy, hydroxyalkyl, nitro, tetrazolyl, oxiadiazolyl, triazolyl, OCH(CH$_3$)—OCOO-cyclohexyl or a cycloanhydride;

Y is H, CH$_2$O-alkyl, CH$_2$S-alkyl, CH$_2$OH, CH$_2$SH or CHO;

W$_1$ and W$_2$ are each independently —(CH$_2$)$_n$—K—Z—Z$_1$, where n is 1 to 5;

K is biphenyl or monophenyl;

Z is tetrazolyl or COO—;

Z$_1$ is H, trityl, chlorotrityl, benzyl or CH(Ph)$_2$; and

E is an anion;

or a pharmaceutically acceptable salt thereof.

In one preferred embodiment, the compound is of formula I.

In one preferred embodiment, the anion E$^-$ is a halo ion, more preferably Br$^-$.

In another preferred embodiment, the compound is of formula II.

In another preferred embodiment, the compound is of formula II.

In one preferred embodiment, W$_1$=W$_2$.

In one particularly preferred embodiment, W$_1$ is

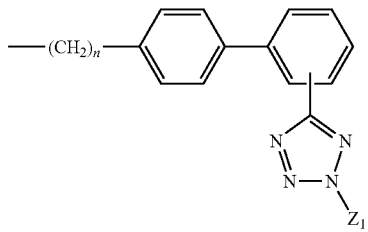

In another particularly preferred embodiment, W$_1$ is

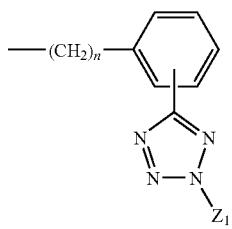

Preferably, n is 1, 2, or 3, more preferably 1 or 2, even more preferably, 1.

In one preferred embodiment, Y is H, CH$_2$OH, CH$_2$OMe, CH$_2$OEt, CH$_2$SH, CH$_2$SMe, halogen or CH$_2$SEt. More preferably, Y is H, CH$_2$OH, CH$_2$OMe, CH$_2$OEt, CH$_2$SH, CH$_2$SMe or CH$_2$SEt. Even more preferably, Y is CH$_2$OH.

Preferably, R is H, F, Br, I or Cl. Even more preferably, R is H or Cl.

In one preferred embodiment, Z$_1$ is H, trityl, halotrityl, benzyl or dibenzyl, more preferably, H, trityl, halotrityl or benzyl.

In another preferred embodiment, Z$_1$ is H, trityl, chlorotrityl or dibenzyl or benzyl, more preferably, H, trityl, chlorotrityl or benzyl.

In one preferred embodiment, X is CH=CH—COOR$^1$, CH$_2$CH$_2$COOR$^1$ or COOR$^1$.

In another preferred embodiment, X is $^t$Bu and Z$_1$ is halotrityl, benzyl or CHPh$_2$.

In one preferred embodiment, R$^1$ is H or alkyl. More preferably, R$^1$ is H, Me or Et.

In one highly preferred embodiment, the compound is of formula M,

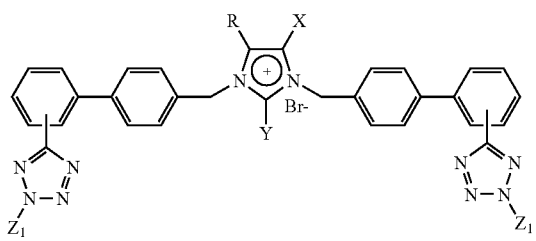

Formula M wherein:
X is CH=CH—COOMe;
R is H or halogen;
Z$_1$ is H, trityl, 2-chlorotrityl or benzyl; and
Y is as defined above.

In another highly preferred embodiment, the compound is of formula N,

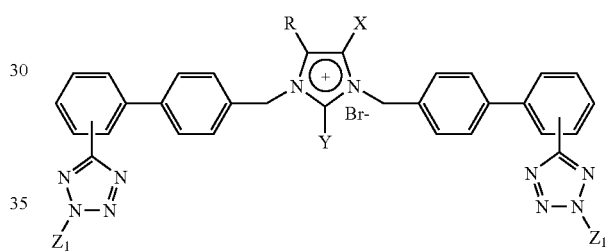

Formula N wherein:
X is CH$_2$CH$_2$COOMe;
R is H or halogen;
Z$_1$ is H, trityl, 2-chlorotrityl or benzyl; and
Y is as defined above.

In another highly preferred embodiment, the compound is of formula O,

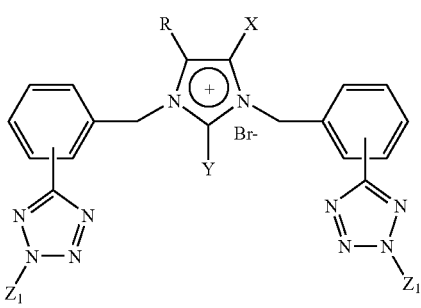

Formula O wherein:
X is CH=CHCOOMe;
R is H or halogen;
Z$_1$ is H, trityl, 2-chlorotrityl or benzyl; and
Y is as defined above.

In another highly preferred embodiment, the compound is of formula P,

Formula P

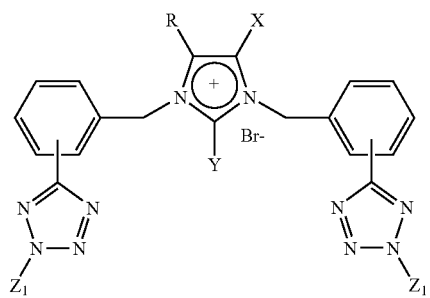

wherein:
X is CH$_2$CH$_2$COOMe;
R is H or halogen;
Z$_1$ is H, trityl, 2-chlorotrityl or benzyl; and
Y is as defined above.

In another highly preferred embodiment, the compound is of formula Q,

Formula Q

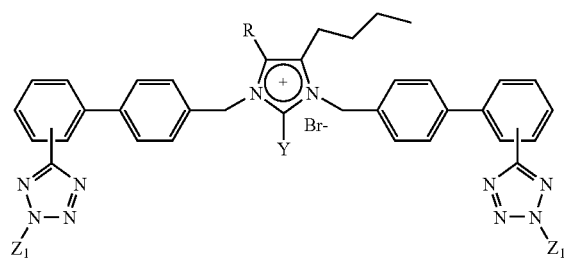

wherein:
R is H or halogen;
Z$_1$ is H, trityl, 2-chlorotrityl or benzyl; and
Y is as defined above.

In another highly preferred embodiment, the compound is of formula R,

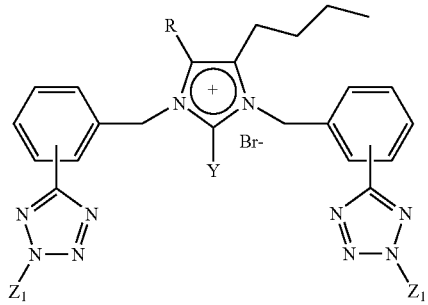

wherein:
R is H or halogen;
Z$_1$ is H, trityl, 2-chlorotrityl or benzyl; and
Y is as defined above.

In another embodiment, the invention relates to a class of novel 1,3-bis-(biphenyl)-imidazole-5-carboxylic esters and 1,3-bis-(phenyl)-imidazole-5-carboxylic esters of urocanic acid, as represented by formulae M', N', O' and P'.

Formulae M', N', O', P'

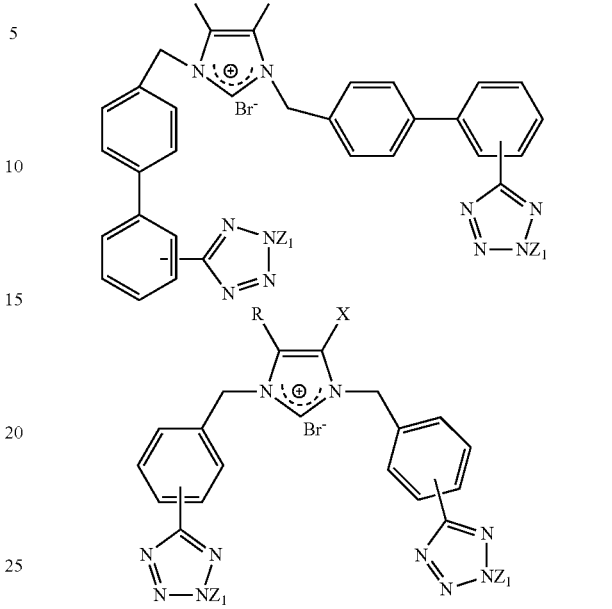

wherein:
R=H, halogen;
X=—CH=CH—COOR$^1$ (Formulae M', O')—CH$_2$—CH$_2$—COOR$^1$ (Formulae N', P');
Z$_1$=H, trityl, chlorotrityl, benzyl, CH(Ph)$_2$, 2-chlorotrityl;
R$^1$=H, CH$_3$, —CH$_2$CH$_3$, —CH$_2$CH$_2$CH$_3$, CH$_2$CH$_2$CH$_2$CH$_3$, -Bz, —CH$_2$Bz.

In another embodiment, the invention relates to a class of novel 1,3-bis-(biphenyl)-5-butylimidazole and 1,3-bis-(phenyl)-5-butylimidazole, as represented by formulae Q', R'.

Formulae Q', R'

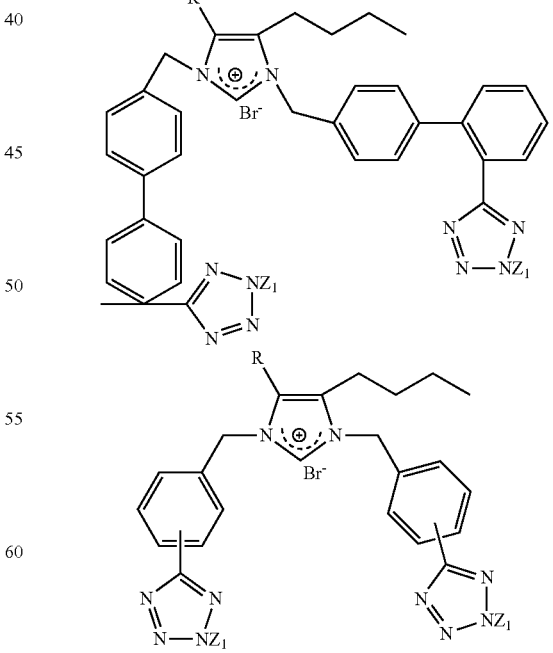

wherein:
R=H, halogen;
Z$_1$=H, trityl, chlorotrityl, benzyl, CH(Ph)$_2$, 2-chlorotrityl.

In another embodiment, this invention concerns a method of selective alkylation for nitrogen-1 with bromomethylenbiphenyl (or monophenyl, trityl, tetrazolyl) by protecting nitrogen-3 with a trityl group.

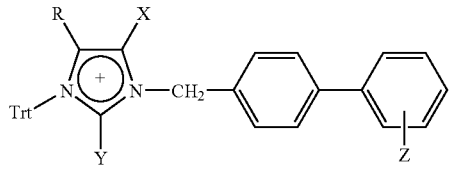

wherein:
Y=H, HOCH$_2$—, CH$_3$OCH$_2$—, C$_2$H$_5$OCH$_2$—, HSCH$_2$—, CH$_3$SCH$_2$—, C$_2$H$_5$SCH$_2$—
R=H, halogen (Cl, Br, I, F) (C$_1$-C$_6$)alkyl;
X=—CH=CH—COOR$^1$, —CH$_2$—CH$_2$—COOR$^1$, —COOR$^1$;
Z=COOH, COOR$^1$
tetrazolyl
tetrazolyl-Z$_1$
Z$_1$=H, trityl, chlorotrityl, benzyl, CH(Ph)$_2$;
R$^1$=H, CH$_3$, —CH$_2$CH$_3$, —CH$_2$CH$_2$CH$_3$, CH$_2$CH$_2$CH$_2$CH$_3$, -Bz, —CH$_2$Bz (C$_2$-C$_5$)alkenyl, (C$_2$-C$_5$)alkynyl.

Another aspect of the invention relates to a compound of formula II or formula III,

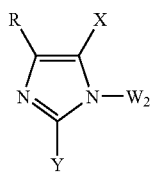

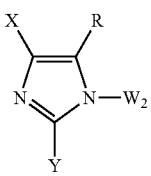

wherein
R is H, halogen;
X is alkenyl, —(CH$_2$)$_v$COOR$^1$ or CH=CH—(CH$_2$)$_v$COOR$^1$, where v is 0 to 10; or
R and X are linked so as to form a fused benzimidazole system; or
X is alkyl, when Z$_1$ is halotrityl, COOH, COO-alkyl, CH$_2$(C$_6$H$_4$-Hal) or CH(Ph)$_2$, wherein each Ph group is optionally substituted by one or more halogens;
R$^1$ is H, alkyl, aralkyl, trityl, halogen, haloalkyl, cycloalkyl, alkenyl, alkynyl, alkoxyalkyl, haloalkoxyalkyl, alkoxy, aryloxy alkoxyalkoxy, cyano, hydroxy, hydroxyalkyl, nitro, tetrazolyl, oxadiazolyl, triazolyl, OCH(CH$_3$)—OCOO-cyclohexyl, cycloanhydride or methyl-5-methyl-[1,3]-dioxolane;
Y is H, CH$_2$O-alkyl, CH$_2$S-alkyl, CH$_2$-halogen, CH$_2$OH, CH$_2$SH, COOH, halogen or CHO;
W$_2$ is —(CH$_2$)$_n$—K—Z—Z$_1$, where n is 1 to 5;
K is biphenyl or monophenyl;
Z is tetrazolyl or COO—; and
Z$_1$ is H, trityl, halotrityl, CH$_2$Ph, COOH, COO-alkyl, or CH(Ph)$_2$, wherein each Ph group is optionally substituted by one or more halogens;
or a pharmaceutically acceptable salt thereof.

In one preferred embodiment, W$_2$ is

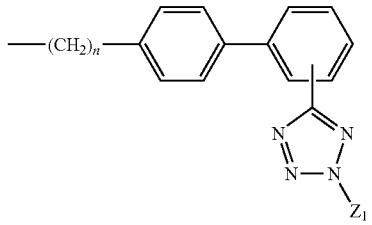

In another preferred embodiment, W$_2$ is

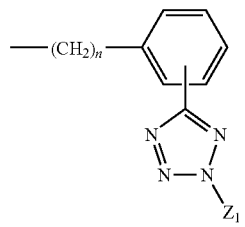

Preferably, n is 1, 2 or 3, more preferably 1 or 2, even more preferably, 1.

In one preferred embodiment, Y is H, CH$_2$OH, CH$_2$OMe, CH$_2$OEt, CH$_2$SH, CH$_2$SMe, COOH or halogen or CH$_2$SEt. More preferably, Y is H, CH$_2$OH, CH$_2$OMe, CH$_2$OEt, CH$_2$SH, CH$_2$SMe or CH$_2$SEt. Even more preferably, Y is CH$_2$OH.

In one preferred embodiment, R is H, Br, F, I or Cl. Even more preferably, R is H or Cl.

In one preferred embodiment, Z$_1$ is H, trityl, halotrityl, dibenzyl or benzyl, more preferably, H, trityl, halotrityl or benzyl.

In another preferred embodiment, Z$_1$ is H, trityl, chlorotrityl, dibenzyl or benzyl, more preferably, Z$_1$ is H, trityl, chlorotrityl or benzyl.

In one preferred embodiment, X is CH=CH—COOR$^1$, CH$_2$CH$_2$COOR$^1$ or COOR$^1$.

In one preferred embodiment, X is alkyl, and Z$_1$ is halotrityl, COOH, COO-alkyl, or CH(Ph)$_2$, wherein each Ph group is optionally substituted by one or more halogens. Preferably, for this embodiment, X is $^t$Bu.

In one preferred embodiment, R$^1$ is H or alkyl. In one preferred embodiment, R$^1$ is H, Me or Et.

In one preferred embodiment, said compound is of formula A,

Formula A

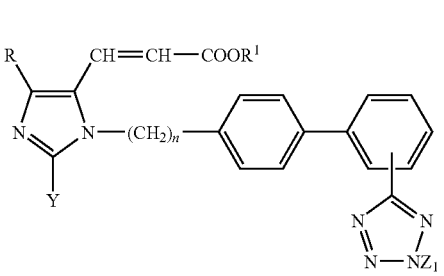

wherein:
R=H or halogen;
R$^1$=H, CH$_3$, or —CH$_2$CH$_3$;
Z$_1$=H, chlorotrityl, benzyl or trityl;
Y is as defined above.

In one preferred embodiment, said compound is of formula B,

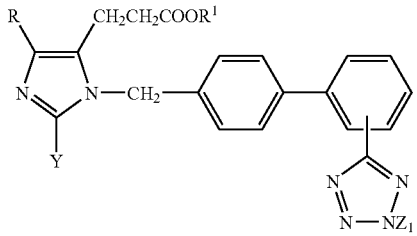
Formula B wherein:
R=H or halogen;
$R^1$=H, $CH_3$, or —$CH_2CH_3$;
$Z_1$=H or trityl;
Y is as defined above.

In one preferred embodiment, said compound is of formula C,

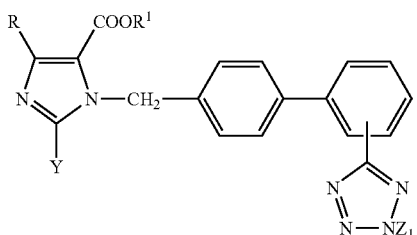
Formula C wherein:
R=H or halogen;
$R^1$=H, $CH_3$, or —$CH_2CH_3$;
$Z_1$=H, chlorotrityl, benzyl or trityl;
Y is as defined above.

In one preferred embodiment, said compound is of formula D,

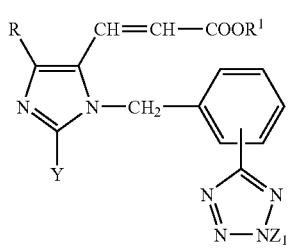
Formula D wherein:
R=H or halogen;
$R^1$=H, $CH_3$, or —$CH_2CH_3$;
$Z_1$=H or trityl;
Y is as defined above.

In one preferred embodiment, said compound is of formula E,

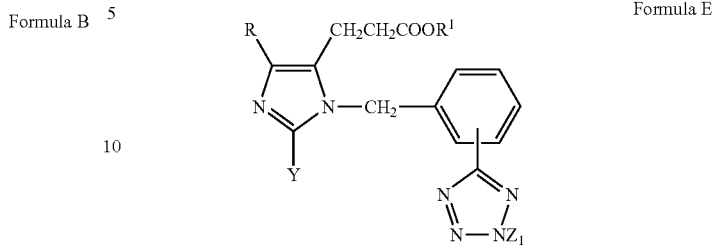
Formula E wherein:
R=H or halogen;
$R^1$=H, $CH_3$, or —$CH_2CH_3$;
$Z_1$=H or trityl;
Y is as defined above.

In one preferred embodiment, said compound is of formula F,

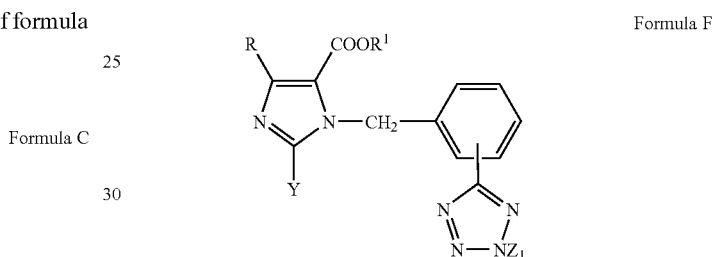
Formula F wherein:
R=H or halogen
$R^1$=H, $CH_3$, or —$CH_2CH_3$;
$Z_1$=H or trityl;
Y is as defined above.

For compounds of formula A-F above, preferably Y=H, $HOCH_2$—, $CH_3OCH_2$—, $C_2H_5OCH_2$—, $HSCH_2$—, $CH_3SCH_2$—, $C_2H_5SCH_2$—.

In another embodiment, the invention relates to a class of novel 1-biphenyl-5-imidazole esters, represented by formulae A', B', C'.

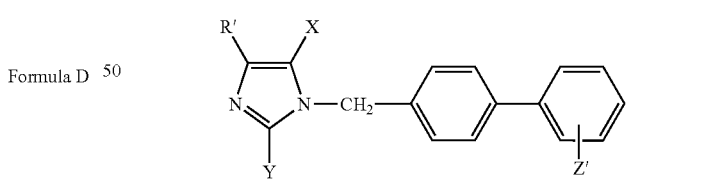
Formula A', B', C' wherein:
Y=H, $HOCH_2$—, $CH_3OCH_2$—, $C_2H_5OCH_2$—, $HSCH_2$—, $CH_3SCH_2$—, $C_2H_5SCH_2$—;
R'=H, halogen (Cl, Br, I, F) or ($C_1$-$C_6$)alkyl;
X=—CH=CH—$COOR^1$ (Formula A'), —$CH_2$—$CH_2$—$COOR^1$ (Formula B'), —$COOR^1$ (Formula C');
Z'=—$COOR^1$,
tetrazolyl
tetrazolyl-$Z'_1$;
$R^1$=H, $CH_3$, —$CH_2CH_3$, —$CH_2CH_2CH_3$, $CH_2CH_2CH_2CH_3$, -Bz, —$CH_2Bz$ ($C_2$-$C_5$)alkenyl, ($C_2$-$C_5$)alkynyl;
$Z'_1$=H, trityl, cloro trityl, benzyl, $CH(Ph)_2$.

In another embodiment, the invention relates to a class of novel 1-monophenyl-5-imidazole esters as represented by formulae D', E', F'.

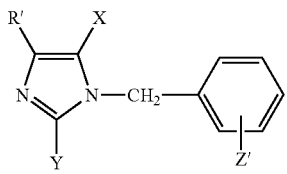

Formula D', E', F' wherein:
Y=H, HOCH$_2$—, CH$_3$OCH$_2$—, C$_2$H$_5$OCH$_2$—, HSCH$_2$—, CH$_3$SCH$_2$—, C$_2$H$_5$SCH$_2$—;
R'=H, Halogen (Cl, Br, I, F), (C$_1$-C$_6$)alkyl;
Z'=—COOR$^1$,
   tetrazolyl
   tetrazolyl-Z'$_1$
Z'$_1$=H, trityl, chlorotrityl, benzyl, CH(Ph)$_2$;
X=—CH=CH—COOR$^1$ (Formula D'), —CH$_2$—CH$_2$—COOR$^1$ (Formula E'), —COOR$^1$ (Formula F');
R$^1$=H, CH$_3$, —CH$_2$CH$_3$, —CH$_2$CH$_2$CH$_3$, CH$_2$CH$_2$CH$_2$CH$_3$, -Bz, —CH$_2$Bz (C$_2$-C$_5$)alkenyl, (C$_2$-C$_5$)alkynyl.

In another embodiment, the invention concerns a method of treating hypertension in a rabbit anesthetized animal model comprising orally administrating a compound of this invention.

In another embodiment, this invention concerns a method of treating hypertension through transdermal administration.

In one highly preferred embodiment of the invention, the compound is of formula A, B, C, D, E, F, M, N, O, P Q or R as set forth below.

Detailed Description of Formulae

A Compound of Formula A with CH=CHCOOR$_1$ at position 5 and biphenyl at position 1

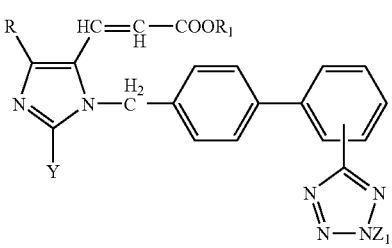

Formula A

| Compound No. | Y | R | R$_1$ | Z$_1$ |
|---|---|---|---|---|
| 1 | H | H | H | H |
| 2 | H | H | H | Trt |
| 3 | H | H | Me | H |
| 4 | H | H | Me | Trt |
| 5 | H | H | Et | H |
| 6 | H | H | Et | Trt |
| 7 | H | Cl | H | H |
| 8 | H | Cl | H | Trt |
| 9 | H | Cl | Me | H |
| 10 | H | Cl | Me | Trt |
| 11 | H | Cl | Et | H |
| 12 | H | Cl | Et | Trt |
| 13 | HOCH$_2$ | H | H | H |

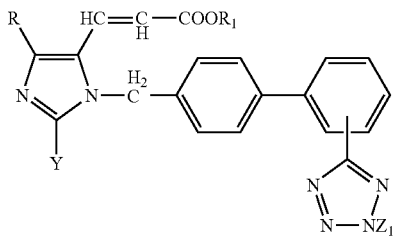

Formula A

| Compound No. | Y | R | R$_1$ | Z$_1$ |
|---|---|---|---|---|
| 14 | HOCH$_2$ | H | H | Trt |
| 15 | HOCH$_2$ | H | Me | H |
| 16 | HOCH$_2$ | H | Me | Trt |
| 17 | HOCH$_2$ | H | Et | H |
| 18 | HOCH$_2$ | H | Et | Trt |
| 19 | HOCH$_2$ | Cl | H | H |
| 20 | HOCH$_2$ | Cl | H | Trt |
| 21 | HOCH$_2$ | Cl | Me | H |
| 22 | HOCH$_2$ | Cl | Me | Trt |
| 23 | HOCH$_2$ | Cl | Et | H |
| 23 | HOCH$_2$ | Cl | Et | Trt |
| 24 | MeOCH$_2$ | H | H | H |
| 25 | MeOCH$_2$ | H | H | Trt |
| 26 | MeOCH$_2$ | H | Me | H |
| 27 | MeOCH$_2$ | H | Me | Trt |
| 28 | MeOCH$_2$ | H | Et | H |
| 29 | MeOCH$_2$ | H | Et | Trt |
| 30 | MeOCH$_2$ | Cl | H | H |
| 31 | MeOCH$_2$ | Cl | H | Trt |
| 32 | MeOCH$_2$ | Cl | Me | H |
| 33 | MeOCH$_2$ | Cl | Me | Trt |
| 34 | MeOCH$_2$ | Cl | Et | H |
| 35 | MeOCH$_2$ | Cl | Et | Trt |
| 36 | EtOCH$_2$ | H | H | H |
| 37 | EtOCH$_2$ | H | H | Trt |
| 38 | EtOCH$_2$ | H | Me | H |
| 39 | EtOCH$_2$ | H | Me | Trt |
| 40 | EtOCH$_2$ | H | Et | H |
| 41 | EtOCH$_2$ | H | Et | Trt |
| 42 | EtOCH$_2$ | Cl | H | H |
| 43 | EtOCH$_2$ | Cl | H | Trt |
| 44 | EtOCH$_2$ | Cl | Me | H |
| 45 | EtOCH$_2$ | Cl | Me | Trt |
| 46 | EtOCH$_2$ | Cl | Et | H |
| 47 | EtOCH$_2$ | Cl | Et | Trt |
| 48 | HSCH$_2$ | H | H | H |
| 49 | HSCH$_2$ | H | H | Trt |
| 50 | HSCH$_2$ | H | Me | H |
| 51 | HSCH$_2$ | H | Me | Trt |
| 52 | HSCH$_2$ | H | Et | H |
| 53 | HSCH$_2$ | H | Et | Trt |
| 54 | MeSCH$_2$ | Cl | H | H |
| 55 | MeSCH$_2$ | Cl | H | Trt |
| 56 | MeSCH$_2$ | Cl | Me | H |
| 57 | MeSCH$_2$ | Cl | Me | Trt |
| 58 | MeSCH$_2$ | Cl | Et | H |
| 59 | MeSCH$_2$ | Cl | Et | Trt |
| 60 | EtSCH$_2$ | Cl | H | H |
| 61 | EtSCH$_2$ | Cl | H | Trt |
| 62 | EtSCH$_2$ | Cl | Me | H |
| 63 | EtSCH$_2$ | Cl | Me | Trt |
| 64 | EtSCH$_2$ | Cl | Et | H |
| 65 | EtSCH$_2$ | Cl | Et | Trt |

A Compound of Formula B with CH₂CH₂COOR₁ at position 5 and biphenyl at position 1

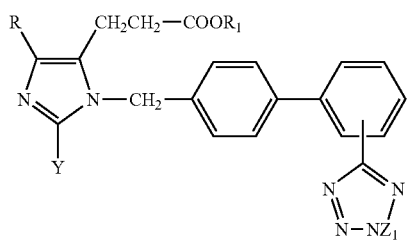

Formula B

| Compound No. | Y | R | R₁ | Z₁ |
|---|---|---|---|---|
| 66 | H | H | H | H |
| 67 | H | H | H | Trt |
| 68 | H | H | Me | H |
| 69 | H | H | Me | Trt |
| 70 | H | H | Et | H |
| 71 | H | H | Et | Trt |
| 72 | H | Cl | H | H |
| 73 | H | Cl | H | Trt |
| 74 | H | Cl | Me | H |
| 75 | H | Cl | Me | Trt |
| 76 | H | Cl | Et | H |
| 77 | H | Cl | Et | Trt |
| 78 | HOCH₂ | H | H | H |
| 79 | HOCH₂ | H | H | Trt |
| 80 | HOCH₂ | H | Me | H |
| 81 | HOCH₂ | H | Me | Trt |
| 82 | HOCH₂ | H | Et | H |
| 83 | HOCH₂ | H | Et | Trt |
| 84 | HOCH₂ | Cl | H | H |
| 85 | HOCH₂ | Cl | H | Trt |
| 86 | HOCH₂ | Cl | Me | H |
| 87 | HOCH₂ | Cl | Me | Trt |
| 88 | HOCH₂ | Cl | Et | H |
| 89 | HOCH₂ | Cl | Et | Trt |
| 90 | MeOCH₂ | H | H | H |
| 91 | MeOCH₂ | H | H | Trt |
| 92 | MeOCH₂ | H | Me | H |
| 93 | MeOCH₂ | H | Me | Trt |
| 94 | MeOCH₂ | H | Et | H |
| 95 | MeOCH₂ | H | Et | Trt |
| 96 | MeOCH₂ | Cl | H | H |
| 97 | MeOCH₂ | Cl | H | Trt |
| 98 | MeOCH₂ | Cl | Me | H |
| 99 | MeOCH₂ | Cl | Me | Trt |
| 100 | MeOCH₂ | Cl | Et | H |
| 101 | MeOCH₂ | Cl | Et | Trt |
| 102 | EtOCH₂ | H | H | H |
| 103 | EtOCH₂ | H | H | Trt |
| 104 | EtOCH₂ | H | Me | H |
| 105 | EtOCH₂ | H | Me | Trt |
| 106 | EtOCH₂ | H | Et | H |
| 107 | EtOCH₂ | H | Et | Trt |
| 108 | EtOCH₂ | Cl | H | H |
| 109 | EtOCH₂ | Cl | H | Trt |
| 110 | EtOCH₂ | Cl | Me | H |
| 111 | EtOCH₂ | Cl | Me | Trt |
| 112 | EtOCH₂ | Cl | Et | H |
| 113 | EtOCH₂ | Cl | Et | Trt |
| 114 | HSCH₂ | H | H | H |
| 115 | HSCH₂ | H | H | Trt |
| 116 | HSCH₂ | H | Me | H |
| 117 | HSCH₂ | H | Me | Trt |
| 118 | HSCH₂ | H | Et | H |
| 119 | HSCH₂ | H | Et | Trt |
| 120 | MeSCH₂ | Cl | H | H |
| 121 | MeSCH₂ | Cl | H | Trt |
| 122 | MeSCH₂ | Cl | Me | H |
| 123 | MeSCH₂ | Cl | Me | Trt |
| 124 | MeSCH₂ | Cl | Et | H |
| 125 | MeSCH₂ | Cl | Et | Trt |
| 126 | EtSCH₂ | Cl | H | H |
| 127 | EtSCH₂ | Cl | H | Trt |
| 128 | EtSCH₂ | Cl | Me | H |
| 129 | EtSCH₂ | Cl | Me | Trt |
| 130 | EtSCH₂ | Cl | Et | H |
| 131 | EtSCH₂ | Cl | Et | Trt |

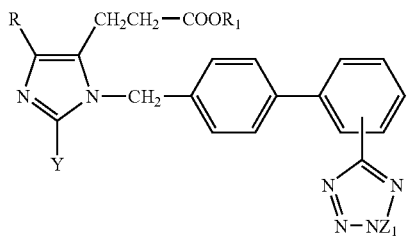

A Compound of Formula C with COOR₁ at position 5 and biphenyl at position 1

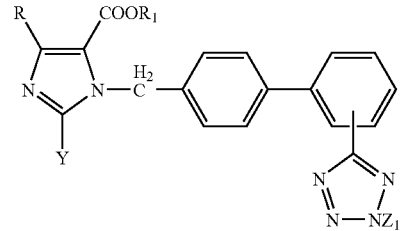

Formula C

| Compound No. | Y | R | R₁ | Z₁ |
|---|---|---|---|---|
| 132 | H | H | H | H |
| 133 | H | H | H | Trt |
| 134 | H | H | Me | H |
| 135 | H | H | Me | Trt |
| 136 | H | H | Et | H |
| 137 | H | H | Et | Trt |
| 138 | H | Cl | H | H |
| 139 | H | Cl | H | Trt |
| 140 | H | Cl | Me | H |
| 141 | H | Cl | Me | Trt |
| 142 | H | Cl | Et | H |
| 143 | H | Cl | Et | Trt |
| 144 | HOCH₂ | H | H | H |
| 145 | HOCH₂ | H | H | Trt |
| 146 | HOCH₂ | H | Me | H |
| 147 | HOCH₂ | H | Me | Trt |
| 148 | HOCH₂ | H | Et | H |
| 149 | HOCH₂ | H | Et | Trt |
| 150 | HOCH₂ | Cl | H | H |
| 151 | HOCH₂ | Cl | H | Trt |
| 152 | HOCH₂ | Cl | Me | H |
| 153 | HOCH₂ | Cl | Me | Trt |
| 154 | HOCH₂ | Cl | Et | H |

Formula C with Compound No., Y, R, R₁, Z₁ columns:

| Compound No. | Y | R | R₁ | Z₁ |
|---|---|---|---|---|
| 155 | HOCH₂ | Cl | Et | Trt |
| 156 | MeOCH₂ | H | H | H |
| 157 | MeOCH₂ | H | H | Trt |
| 158 | MeOCH₂ | H | Me | H |
| 159 | MeOCH₂ | H | Me | Trt |
| 160 | MeOCH₂ | H | Et | H |
| 161 | MeOCH₂ | H | Et | Trt |
| 162 | MeOCH₂ | Cl | H | H |
| 163 | MeOCH₂ | Cl | H | Trt |
| 164 | MeOCH₂ | Cl | Me | H |
| 165 | MeOCH₂ | Cl | Me | Trt |
| 166 | MeOCH₂ | Cl | Et | H |
| 167 | MeOCH₂ | Cl | Et | Trt |
| 168 | EtOCH₂ | H | H | H |
| 169 | EtOCH₂ | H | H | Trt |
| 170 | EtOCH₂ | H | Me | H |
| 171 | EtOCH₂ | H | Me | Trt |
| 172 | EtOCH₂ | H | Et | H |
| 173 | EtOCH₂ | H | Et | Trt |
| 174 | EtOCH₂ | Cl | H | H |
| 175 | EtOCH₂ | Cl | H | Trt |
| 176 | EtOCH₂ | Cl | Me | H |
| 177 | EtOCH₂ | Cl | Me | Trt |
| 178 | EtOCH₂ | Cl | Et | H |
| 179 | EtOCH₂ | Cl | Et | Trt |
| 180 | HSCH₂ | H | H | H |
| 181 | HSCH₂ | H | H | Trt |
| 182 | HSCH₂ | H | Me | H |
| 183 | HSCH₂ | H | Me | Trt |
| 184 | HSCH₂ | H | Et | H |
| 185 | HSCH₂ | H | Et | Trt |
| 186 | MeSCH₂ | Cl | H | H |
| 187 | MeSCH₂ | Cl | H | Trt |
| 188 | MeSCH₂ | Cl | Me | H |
| 189 | MeSCH₂ | Cl | Me | Trt |
| 190 | MeSCH₂ | Cl | Et | H |
| 191 | MeSCH₂ | Cl | Et | Trt |
| 192 | EtSCH₂ | Cl | H | H |
| 193 | EtSCH₂ | Cl | H | Trt |
| 194 | EtSCH₂ | Cl | Me | H |
| 195 | EtSCH₂ | Cl | Me | Trt |
| 196 | EtSCH₂ | Cl | Et | H |
| 197 | EtSCH₂ | Cl | Et | Trt |

A Compound of Formula D with CH=CHCOOR₁ at Position 5 and monophenyl at position 1

Formula D

| Compound No. | Y | R | R₁ | Z₁ |
|---|---|---|---|---|
| 198 | H | H | H | H |
| 199 | H | H | H | Trt |
| 200 | H | H | Me | H |
| 201 | H | H | Me | Trt |
| 202 | H | H | Et | H |
| 203 | H | H | Et | Trt |
| 204 | H | Cl | H | H |
| 205 | H | Cl | H | Trt |
| 206 | H | Cl | Me | H |
| 207 | H | Cl | Me | Trt |
| 208 | H | Cl | Et | H |
| 209 | H | Cl | Et | Trt |
| 210 | HOCH₂ | H | H | H |
| 211 | HOCH₂ | H | H | Trt |
| 212 | HOCH₂ | H | Me | H |
| 213 | HOCH₂ | H | Me | Trt |
| 214 | HOCH₂ | H | Et | H |
| 215 | HOCH₂ | H | Et | Trt |
| 216 | HOCH₂ | Cl | H | H |
| 217 | HOCH₂ | Cl | H | Trt |
| 218 | HOCH₂ | Cl | Me | H |
| 219 | HOCH₂ | Cl | Me | Trt |
| 220 | HOCH₂ | Cl | Et | H |
| 221 | HOCH₂ | Cl | Et | Trt |
| 222 | MeOCH₂ | H | H | H |
| 223 | MeOCH₂ | H | H | Trt |
| 224 | MeOCH₂ | H | Me | H |
| 225 | MeOCH₂ | H | Me | Trt |
| 226 | MeOCH₂ | H | Et | H |
| 227 | MeOCH₂ | H | Et | Trt |
| 228 | MeOCH₂ | Cl | H | H |
| 229 | MeOCH₂ | Cl | H | Trt |
| 230 | MeOCH₂ | Cl | Me | H |
| 231 | MeOCH₂ | Cl | Me | Trt |
| 232 | MeOCH₂ | Cl | Et | H |
| 233 | MeOCH₂ | Cl | Et | Trt |
| 234 | EtOCH₂ | H | H | H |
| 235 | EtOCH₂ | H | H | Trt |
| 236 | EtOCH₂ | H | Me | H |
| 237 | EtOCH₂ | H | Me | Trt |
| 238 | EtOCH₂ | H | Et | H |
| 239 | EtOCH₂ | H | Et | Trt |
| 240 | EtOCH₂ | Cl | H | H |
| 241 | EtOCH₂ | Cl | H | Trt |
| 242 | EtOCH₂ | Cl | Me | H |
| 243 | EtOCH₂ | Cl | Me | Trt |
| 244 | EtOCH₂ | Cl | Et | H |
| 245 | EtOCH₂ | Cl | Et | Trt |
| 246 | HSCH₂ | H | H | H |
| 247 | HSCH₂ | H | H | Trt |
| 248 | HSCH₂ | H | Me | H |
| 249 | HSCH₂ | H | Me | Trt |
| 250 | HSCH₂ | H | Et | H |
| 251 | HSCH₂ | H | Et | Trt |
| 252 | MeSCH₂ | Cl | H | H |
| 253 | MeSCH₂ | Cl | H | Trt |
| 254 | MeSCH₂ | Cl | Me | H |

-continued

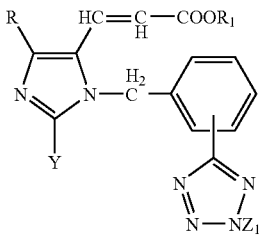

Formula D

| Compound No. | Y | R | R₁ | Z₁ |
|---|---|---|---|---|
| 255 | MeSCH₂ | Cl | Me | Trt |
| 256 | MeSCH₂ | Cl | Et | H |
| 257 | MeSCH₂ | Cl | Et | Trt |
| 258 | EtSCH₂ | Cl | H | H |
| 259 | EtSCH₂ | Cl | H | Trt |
| 260 | EtSCH₂ | Cl | Me | H |
| 261 | EtSCH₂ | Cl | Me | Trt |
| 262 | EtSCH₂ | Cl | Et | H |
| 263 | EtSCH₂ | Cl | Et | Trt |

A Compound of Formula E with CH₂CH₂COOR₁ at position 5 and monophenyl at position 1

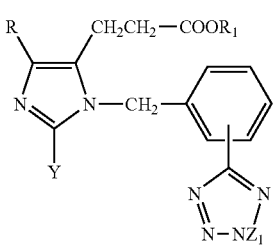

Formula E

| Compound No | Y | R | R₁ | Z₁ |
|---|---|---|---|---|
| 264 | H | H | H | H |
| 265 | H | H | H | Trt |
| 266 | H | H | Me | H |
| 267 | H | H | Me | Trt |
| 268 | H | H | Et | H |
| 269 | H | H | Et | Trt |
| 270 | H | Cl | H | H |
| 271 | H | Cl | H | Trt |
| 272 | H | Cl | Me | H |
| 273 | H | Cl | Me | Trt |
| 274 | H | Cl | Et | H |
| 275 | H | Cl | Et | Trt |
| 276 | HOCH₂ | H | H | H |
| 277 | HOCH₂ | H | H | Trt |
| 278 | HOCH₂ | H | Me | H |
| 279 | HOCH₂ | H | Me | Trt |
| 280 | HOCH₂ | H | Et | H |
| 281 | HOCH₂ | H | Et | Trt |
| 282 | HOCH₂ | Cl | H | H |
| 283 | HOCH₂ | Cl | H | Trt |
| 284 | HOCH₂ | Cl | Me | H |
| 285 | HOCH₂ | Cl | Me | Trt |
| 286 | HOCH₂ | Cl | Et | H |
| 287 | HOCH₂ | Cl | Et | Trt |
| 288 | MeOCH₂ | H | H | H |
| 289 | MeOCH₂ | H | H | Trt |

-continued

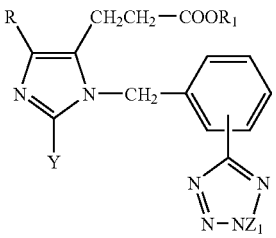

Formula E

| Compound No | Y | R | R₁ | Z₁ |
|---|---|---|---|---|
| 290 | MeOCH₂ | H | Me | H |
| 291 | MeOCH₂ | H | Me | Trt |
| 292 | MeOCH₂ | H | Et | H |
| 293 | MeOCH₂ | H | Et | Trt |
| 294 | MeOCH₂ | Cl | H | H |
| 295 | MeOCH₂ | Cl | H | Trt |
| 296 | MeOCH₂ | Cl | Me | H |
| 297 | MeOCH₂ | Cl | Me | Trt |
| 298 | MeOCH₂ | Cl | Et | H |
| 299 | MeOCH₂ | Cl | Et | Trt |
| 300 | EtOCH₂ | H | H | H |
| 301 | EtOCH₂ | H | H | Trt |
| 302 | EtOCH₂ | H | Me | H |
| 303 | EtOCH₂ | H | Me | Trt |
| 304 | EtOCH₂ | H | Et | H |
| 305 | EtOCH₂ | H | Et | Trt |
| 306 | EtOCH₂ | Cl | H | H |
| 307 | EtOCH₂ | Cl | H | Trt |
| 308 | EtOCH₂ | Cl | Me | H |
| 309 | EtOCH₂ | Cl | Me | Trt |
| 310 | EtOCH₂ | Cl | Et | H |
| 311 | EtOCH₂ | Cl | Et | Trt |
| 312 | HSCH₂ | H | H | H |
| 313 | HSCH₂ | H | H | Trt |
| 314 | HSCH₂ | H | Me | H |
| 315 | HSCH₂ | H | Me | Trt |
| 316 | HSCH₂ | H | Et | H |
| 317 | HSCH₂ | H | Et | Trt |
| 318 | MeSCH₂ | Cl | H | H |
| 319 | MeSCH₂ | Cl | H | Trt |
| 320 | MeSCH₂ | Cl | Me | H |
| 321 | MeSCH₂ | Cl | Me | Trt |
| 322 | MeSCH₂ | Cl | Et | H |
| 323 | MeSCH₂ | Cl | Et | Trt |
| 324 | EtSCH₂ | Cl | H | H |
| 325 | EtSCH₂ | Cl | H | Trt |
| 326 | EtSCH₂ | Cl | Me | H |
| 327 | EtSCH₂ | Cl | Me | Trt |
| 328 | EtSCH₂ | Cl | Et | H |
| 329 | EtSCH₂ | Cl | Et | Trt |

A Compound of Formula F with COOR$_1$ at position 5 and monophenyl at position 1

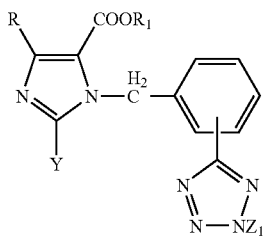

Formula F

| Compound No. | Y | R | R$_1$ | Z$_1$ |
|---|---|---|---|---|
| 330 | H | H | H | H |
| 331 | H | H | H | Trt |
| 332 | H | H | Me | H |
| 333 | H | H | Me | Trt |
| 334 | H | H | Et | H |
| 335 | H | H | Et | Trt |
| 336 | H | Cl | H | H |
| 337 | H | Cl | H | Trt |
| 338 | H | Cl | Me | H |
| 339 | H | Cl | Me | Trt |
| 340 | H | Cl | Et | H |
| 341 | H | Cl | Et | Trt |
| 342 | HOCH$_2$ | H | H | H |
| 343 | HOCH$_2$ | H | H | Trt |
| 344 | HOCH$_2$ | H | Me | H |
| 345 | HOCH$_2$ | H | Me | Trt |
| 346 | HOCH$_2$ | H | Et | H |
| 347 | HOCH$_2$ | H | Et | Trt |
| 348 | HOCH$_2$ | Cl | H | H |
| 349 | HOCH$_2$ | Cl | H | Trt |
| 350 | HOCH$_2$ | Cl | Me | H |
| 351 | HOCH$_2$ | Cl | Me | Trt |
| 352 | HOCH$_2$ | Cl | Et | H |
| 353 | HOCH$_2$ | Cl | Et | Trt |
| 354 | MeOCH$_2$ | H | H | H |
| 355 | MeOCH$_2$ | H | H | Trt |
| 356 | MeOCH$_2$ | H | Me | H |
| 357 | MeOCH$_2$ | H | Me | Trt |
| 358 | MeOCH$_2$ | H | Et | H |
| 359 | MeOCH$_2$ | H | Et | Trt |
| 360 | MeOCH$_2$ | Cl | H | H |
| 361 | MeOCH$_2$ | Cl | H | Trt |
| 362 | MeOCH$_2$ | Cl | Me | H |
| 363 | MeOCH$_2$ | Cl | Me | Trt |
| 364 | MeOCH$_2$ | Cl | Et | H |
| 365 | MeOCH$_2$ | Cl | Et | Trt |
| 366 | EtOCH$_2$ | H | H | H |
| 367 | EtOCH$_2$ | H | H | Trt |
| 368 | EtOCH$_2$ | H | Me | H |
| 369 | EtOCH$_2$ | H | Me | Trt |
| 370 | EtOCH$_2$ | H | Et | H |
| 371 | EtOCH$_2$ | H | Et | Trt |
| 372 | EtOCH$_2$ | Cl | H | H |
| 373 | EtOCH$_2$ | Cl | H | Trt |
| 374 | EtOCH$_2$ | Cl | Me | H |
| 375 | EtOCH$_2$ | Cl | Me | Trt |
| 376 | EtOCH$_2$ | Cl | Et | H |
| 377 | EtOCH$_2$ | Cl | Et | Trt |
| 378 | HSCH$_2$ | H | H | H |
| 379 | HSCH$_2$ | H | H | Trt |
| 380 | HSCH$_2$ | H | Me | H |
| 381 | HSCH$_2$ | H | Me | Trt |
| 382 | HSCH$_2$ | H | Et | H |
| 383 | HSCH$_2$ | H | Et | Trt |
| 384 | MeSCH$_2$ | Cl | H | H |
| 385 | MeSCH$_2$ | Cl | H | Trt |
| 386 | MeSCH$_2$ | Cl | Me | H |

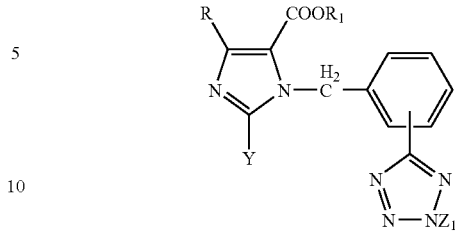

Formula F

| Compound No. | Y | R | R$_1$ | Z$_1$ |
|---|---|---|---|---|
| 387 | MeSCH$_2$ | Cl | Me | Trt |
| 388 | MeSCH$_2$ | Cl | Et | H |
| 389 | MeSCH$_2$ | Cl | Et | Trt |
| 390 | EtSCH$_2$ | Cl | H | H |
| 391 | EtSCH$_2$ | Cl | H | Trt |
| 392 | EtSCH$_2$ | Cl | Me | H |
| 393 | EtSCH$_2$ | Cl | Me | Trt |
| 394 | EtSCH$_2$ | Cl | Et | H |
| 395 | EtSCH$_2$ | Cl | Et | Trt |

Activity

Novel 1,5-disubstituted imidazole based angiotensin II (AII) receptor AT1 antagonists related to Losartan with reversion of butyl and hydroxymethylene groups at positions 1,4 of imidazole were synthesized and evaluated for their receptor affinity and antagonist activity in anaesthetized rabbits. Design of our AII receptor AT1 antagonists was based on models of Angiotensin II and Sarmesin in which the major conformational feature was defined as the ring cluster between the phenol of Tyr$^4$, imidazole of His$^6$, phenyl and carboxylate of Phe$^8$ (J. Med. Chem. 1999, 42, 1714).

Compounds with a 5-butyl substituent showed higher antihypertensive activity compared to those with 5-methyl or a fused ring. The most promising candidates were further evaluated using in vitro binding studies to AT1 and AT2 receptors in order to test their specificity and the correlation with in vivo studies. In particular, compounds 5-butyl-2-hydroxymethyl-1-[[2'-[[N-(2-chloro-triphenylmethyl)]tetrazol-5yl]biphenyl-4-yl]methyl]imidazole 20 and especially 5-butyl-1-hydroxymethyl-1-[[2'-(1H-tetrazol-5-yl]biphenyl-4-yl]methyl]imidazole 22 were highly potent in experimental models. Compound 22, with an unprotected tetrazole group, shows a similar affinity for AT1 receptor as Losartan, while compound 20, with the tetrazole group trityl protected, shows lower affinity. Results indicate that reorientation of the butyl and the hydroxymethyl groups on the imidazole template of Losartan retains high binding to the AT1 receptor, and that the spacing of the substituents at positions 1,4 is of primary importance.

Dialkylation of these compounds, as well as intermediates thereof, leads to higher affinity for receptor activity and increased antagonist activity. Thus, 1,3-dialkylated 4(5)-substituted imidazoles obtained by extensive alkylation of compounds 20 and 22, as well as intermediates thereof, provide an increased negative charge which is required for better affinity to the angiotensin II receptor, as well as higher lipophilicity which is required for transdermal administration.

Therapeutic Use

The compounds of the present invention have been found to inhibit angiotensin II activity and are therefore believed to be of use in the treatment of hypertension and other cardiac disorders.

As used herein the phrase "preparation of a medicament" includes the use of a compound of the invention directly as the medicament in addition to its use in a screening programme for further therapeutic agents or in any stage of the manufacture of such a medicament.

In one preferred embodiment, the medicament is in a form suitable for topical or transdermal administration. More preferably, the medicament is in the form of a transdermal patch.

In another preferred embodiment, the medicament is in a form suitable for oral, intravenous or subcutaneous administration Another aspect of the invention relates to a method of treating hypertension or a cardiovascular disorder in a subject, said method comprising administering to the subject a therapeutically effective amount of a compound of formula I or II or III as defined above, or a pharmaceutically acceptable salt thereof.

Preferably, the compound is administered transdermally, more preferably by means of a transdermal patch.

Preferably, the subject is a human.

Another aspect of the invention relates to a compound of formula I or II or III as defined above for use in medicine.

Another aspect of the invention relates to a compound of formula I or II or III as defined above for treating hypertension or a cardiovascular disorder.

Pharmaceutical Compositions

Another aspect of the invention relates to a pharmaceutical composition comprising a compound of the invention admixed with a pharmaceutically acceptable diluent, excipient or carrier, or a mixture thereof. Even though the compounds of the present invention (including their pharmaceutically acceptable salts, esters and pharmaceutically acceptable solvates) can be administered alone, they will generally be administered in admixture with a pharmaceutical carrier, excipient or diluent, particularly for human therapy. The pharmaceutical compositions may be for human or animal usage in human and veterinary medicine.

Examples of such suitable excipients for the various different forms of pharmaceutical compositions described herein may be found in the "Handbook of Pharmaceutical Excipients, $2^{nd}$ Edition, (1994), Edited by A Wade and P J Weller.

Acceptable carriers or diluents for therapeutic use are well known in the pharmaceutical art, and are described, for example, in Remington's Pharmaceutical Sciences, Mack Publishing Co. (A. R. Gennaro edit. 1985).

Examples of suitable carriers include lactose, starch, glucose, methyl cellulose, magnesium stearate, mannitol, sorbitol and the like. Examples of suitable diluents include ethanol, glycerol and water.

The choice of pharmaceutical carrier, excipient or diluent can be selected with regard to the intended route of administration and standard pharmaceutical practice. The pharmaceutical compositions may comprise as, or in addition to, the carrier, excipient or diluent any suitable binder(s), lubricant(s), suspending agent(s), coating agent(s), solubilising agent(s).

Examples of suitable binders include starch, gelatin, natural sugars such as glucose, anhydrous lactose, free-flow lactose, beta-lactose, corn sweeteners, natural and synthetic gums, such as acacia, tragacanth or sodium alginate, carboxymethyl cellulose and polyethylene glycol.

Examples of suitable lubricants include sodium oleate, sodium stearate, magnesium stearate, sodium benzoate, sodium acetate, sodium chloride and the like.

Preservatives, stabilizers, dyes and even flavoring agents may be provided in the pharmaceutical composition. Examples of preservatives include sodium benzoate, sorbic acid and esters of p-hydroxybenzoic acid. Antioxidants and suspending agents may be also used.

Salts/Esters

The compounds of the present invention can be present as salts or esters, in particular pharmaceutically acceptable salts or esters.

Pharmaceutically acceptable salts of the compounds of the invention include suitable acid addition or base salts thereof. A review of suitable pharmaceutical salts may be found in Berge et al, J Pharm Sci, 66, 1-19 (1977). Salts are formed, for example with strong inorganic acids such as mineral acids, e.g. sulphuric acid, phosphoric acid or hydrohalic acids; with strong organic carboxylic acids, such as alkanecarboxylic acids of 1 to 4 carbon atoms which are unsubstituted or substituted (e.g., by halogen), such as acetic acid; with saturated or unsaturated dicarboxylic acids, for example oxalic, malonic, succinic, maleic, fumaric, phthalic or tetraphthalic; with hydroxycarboxylic acids, for example ascorbic, glycolic, lactic, malic, tartaric or citric acid; with aminoacids, for example aspartic or glutamic acid; with benzoic acid; or with organic sulfonic acids, such as ($C_1$-$C_4$)-alkyl- or aryl-sulfonic acids which are unsubstituted or substituted (for example, by a halogen) such as methane- or p-toluene sulfonic acid. Esters are formed either using organic acids or alcohols/hydroxides, depending on the functional group being esterified. Organic acids include carboxylic acids, such as alkanecarboxylic acids of 1 to 12 carbon atoms which are unsubstituted or substituted (e.g., by halogen), such as acetic acid; with saturated or unsaturated dicarboxylic acid, for example oxalic, malonic, succinic, maleic, fumaric, phthalic or tetraphthalic; with hydroxycarboxylic acids, for example ascorbic, glycolic, lactic, malic, tartaric or citric acid; with aminoacids, for example aspartic or glutamic acid; with benzoic acid; or with organic sulfonic acids, such as ($C_1$-$C_4$)-alkyl- or aryl-sulfonic acids which are unsubstituted or substituted (for example, by a halogen) such as methane- or p-toluene sulfonic acid. Suitable hydroxides include inorganic hydroxides, such as sodium hydroxide, potassium hydroxide, calcium hydroxide, aluminium hydroxide. Alcohols include alkanealcohols of 1-12 carbon atoms which may be unsubstituted or substituted, e.g. by a halogen).

Enantiomers/Tautomers

In all aspects of the present invention previously discussed, the invention includes, where appropriate all enantiomers and tautomers of the compounds of the invention. The man skilled in the art will recognise compounds that possess an optical properties (one or more chiral carbon atoms) or tautomeric characteristics. The corresponding enantiomers and/or tautomers may be isolated/prepared by methods known in the art.

Stereo and Geometric Isomers

Some of the compounds of the invention may exist as stereoisomers and/or geometric isomers—e.g. they may possess one or more asymmetric and/or geometric centres and so may exist in two or more stereoisomeric and/or geometric forms. The present invention contemplates the use of all the individual stereoisomers and geometric isomers of those inhibitor agents, and mixtures thereof. The terms used in the claims encompass these forms, provided said forms retain the appropriate functional activity (though not necessarily to the same degree).

The present invention also includes all suitable isotopic variations of the agent or a pharmaceutically acceptable salt thereof. An isotopic variation of an agent of the present invention or a pharmaceutically acceptable salt thereof is defined as one in which at least one atom is replaced by an atom having the same atomic number but an atomic mass different from the atomic mass usually found in nature. Examples of isotopes that can be incorporated into the agent and pharmaceutically acceptable salts thereof include isotopes of hydrogen, carbon, nitrogen, oxygen, phosphorus, sulphur, fluorine and chlorine such as $^2$H, $^3$H, $^{13}$C, $^{15}$N, $^{17}$O, $^{18}$O, $^{31}$P, $^{32}$P, $^{35}$S, $^{18}$F and $^{36}$Cl, respectively. Certain isotopic variations of the agent and pharmaceutically acceptable salts thereof, for example, those in which a radioactive isotope such as $^3$H or $^{14}$C is incorporated, are useful in drug and/or substrate tissue distribution studies. Tritiated, i.e., $^3$H, and carbon-14, i.e., $^{14}$C, isotopes are particularly preferred for their ease of preparation and detectability. Further, substitution with isotopes such as deuterium, i.e., $^2$H, may afford certain therapeutic advantages resulting from greater metabolic stability, for example, increased in vivo half-life or reduced dosage requirements and hence may be preferred in some circumstances. Isotopic variations of the agent of the present invention and pharmaceutically acceptable salts thereof of this invention can generally be prepared by conventional procedures using appropriate isotopic variations of suitable reagents.

Solvates

The present invention also includes solvate forms of the compounds of the present invention. The terms used in the claims encompass these forms.

Polymorphs

The invention furthermore relates to compounds of the present invention in their various crystalline forms, polymorphic forms and (an)hydrous forms. It is well established within the pharmaceutical industry that chemical compounds may be isolated in any of such forms by slightly varying the method of purification and or isolation form the solvents used in the synthetic preparation of such compounds.

Prodrugs

The invention further includes compounds of the present invention in prodrug form. Such prodrugs are generally compounds of the invention wherein one or more appropriate groups have been modified such that the modification may be reversed upon administration to a human or mammalian subject. Such reversion is usually performed by an enzyme naturally present in such subject, though it is possible for a second agent to be administered together with such a prodrug in order to perform the reversion in vivo. Examples of such modifications include ester (for example, any of those described above), wherein the reversion may be carried out be an esterase etc. Other such systems will be well known to those skilled in the art.

Administration

The pharmaceutical compositions of the present invention may be adapted for oral, rectal, vaginal, parenteral, intramuscular, intraperitoneal, intraarterial, intrathecal, intrabronchial, subcutaneous, intradermal, transdermal, intravenous, nasal, buccal or sublingual routes of administration.

For oral administration, particular use is made of compressed tablets, pills, tablets, gellules, drops, and capsules. Preferably, these compositions contain from 1 to 250 mg and more preferably from 10-100 mg, of active ingredient per dose.

Other forms of administration comprise solutions or emulsions which may be injected intravenously, intraarterially, intrathecally, subcutaneously, intradermally, intraperitoneally or intramuscularly, and which are prepared from sterile or sterilisable solutions. The pharmaceutical compositions of the present invention may also be in form of suppositories, pessaries, suspensions, emulsions, lotions, ointments, creams, gels, sprays, solutions or dusting powders.

An alternative means of transdermal administration is by use of a skin patch. For example, the active ingredient can be incorporated into a cream consisting of an aqueous emulsion of polyethylene glycols or liquid paraffin. The active ingredient can also be incorporated, at a concentration of between 1 and 10% by weight, into an ointment consisting of a white wax or white soft paraffin base together with such stabilisers and preservatives as may be required.

Injectable forms may contain between 10-1000 mg, preferably between 10-250 mg, of active ingredient per dose.

Compositions may be formulated in unit dosage form, i.e., in the form of discrete portions containing a unit dose, or a multiple or sub-unit of a unit dose.

Dosage

A person of ordinary skill in the art can easily determine an appropriate dose of one of the instant compositions to administer to a subject without undue experimentation. Typically, a physician will determine the actual dosage which will be most suitable for an individual patient and it will depend on a variety of factors including the activity of the specific compound employed, the metabolic stability and length of action of that compound, the age, body weight, general health, sex, diet, mode and time of administration, rate of excretion, drug combination, the severity of the particular condition, and the individual undergoing therapy. The dosages disclosed herein are exemplary of the average case. There can of course be individual instances where higher or lower dosage ranges are merited, and such are within the scope of this invention.

Depending upon the need, the agent may be administered at a dose of from 0.01 to 30 mg/kg body weight, such as from 0.1 to 10 mg/kg, more preferably from 0.1 to 1 mg/kg body weight.

Transdermal Use of Angiotensin Receptor Blockers

In Western Societies, only about one-half of hypertensive patients are being treated and only a third of those treated have their blood pressure well controlled. A major reason for this shortfall is lack of patient compliance with therapy. Very few ways to improve the goals of health care have been noted in the literature. Among them, fewer doses are considered of paramount significance to improve patient adherence. Transdermal formulations are particularly advantageous since they can deliver antihypertensive medications for prolonged periods of time (up to one week).

Besides clonidine patches, no other formulations containing antihypertensive medications are currently in use. The newer antihypertensive medications such as angiotensin II receptor blockers are as effective as the other categories of antihypertensive drugs and are extremely well tolerated (incidence of side effects similar to placebo). In addition, relative indications for their use are heart failure, diabetes mellitus, proteinuric chronic kidney disease and left ventricular hypertrophy. Patients that cannot tolerate ACE inhibitors due to dry cough (7% of men and 15% of women) or angioedema benefit from angiotensin II receptor blockers.

The angiotensin II receptor blockers of the present invention have proven as effective as Losartan in controlling angiotensin II-induced hypertension in rabbits. Moreover, the applicant has further shown that these hydrophilic compounds may be transformed to extremely lipophilic molecules by incorporating highly lipophilic groups such as trityl or chlorotrityl into the tetrazole pharmacophore group. Esterification of the carboxyl group at position 5 of the imidazole or position 3 of the indole also increases lipophilicity. Dialkylation of 4(5)-substituted imidazoles further increases affinity and lipophilicity.

Both formulations, hydrophilic and lipophilic, have been shown to have a similar antihypertensive potency when given intravenously in rabbits with angiotensin II-induced hypertension.

Thus, the present invention further relates to the transformation of angiotensin II receptor blockers to lipophilic molecules by the protection of the tetrazole group with a trityl moiety, and esterification of the carboxyl group at the 5-position of the imidazole, and the use of these molecules for the transdermal delivery of the angiotensin II blocker. Preliminary experiments have shown that blood pressure can be lowered by 20 mmHg for two hours in conscious rabbits made hypertensive by angiotensin II infusion when a mixture of 15 mg of a lipophilic angiotensin II receptor blocker in accordance with the invention is applied to bare skin with Vaseline.

Process

A further aspect of the invention relates to a process for preparing compounds of the invention.

To date, lengthy procedures have been required in order to obtain the final product. Typically, low yields and the formation of stereoisomers increase the overall cost of the synthesis. One such example is the synthesis of the potent Losartan analogues described by Wahhab et al (Drug Research, 43, 11, 1993). However, recent studies by the applicant have greatly improved the activity of these lead structures in established bioassays, as well as improving the synthetic procedure to provide short, regioselective, high yielding processes suitable for large scale production. Furthermore, dialkylation by novel methods, together with conversion of hydrophilic compounds to lipophilic compounds, increases antagonist activity and enables transdermal delivery.

One aspect of the present invention therefore relates to a four step, high yielding synthesis of 1,5-imidazole based AT1 receptor antagonists. Tritylation of the tetrazole by trityl (or a derivative thereof) transforms the compounds to their lipophilic prodrug forms for transdermal delivery.

In particular, the use of the Barlos method (Barlos and Gatos et al, 1999), allows exclusive protection of N1 imidazole in 1,5-alkyl imidazoles upon tritylation with trityl chloride. Subsequent alkylation by Br-Bip-Tet-Tr introduces the pharmacophoric Biphenyl tetrazole group in the desired N3 position of the imidazole ring in a previously unreported simple and convenient manner. This strategy dramatically reduces the steps required for the synthesis of potent 1,5-imidazole based AT1 receptor antagonists starting from commercially available 1,5-butyl imidazole or 1,5-alkyl ester imidazole.

The six step sequence (tritylation, alkylation, didetritylation, tetrazole tritylation, hydroxymethylation, detritylation) is a highly regioselective, high yielding method for preparing the desired potent Losartan analogue 22 from 1,5-butyl imidazole. This method is markedly improved from the low yielding, twelve step prior art method which led to the production of multiple isomers. The invention further provides a general method for the design and synthesis of other potent AT1 receptor antagonists with dual activity to a second receptor, by appropriate modification of the butyl group at position 5.

The invention also provides a convenient one-pot synthesis for the synthesis of lipophilic AT1 Receptor antagonists through 1,5-imidazole scaffolds. In particular, the one-pot synthesis contains four distinct steps: (i) tritylation; (ii) alkylation; (iii) detritylation of two trityl groups; and (iv) selective tritylation of tetrazole. Additionally, the alkyl chain at position 5 is replaced by a carboxyl group. Esterification of the carboxyl group and tritylation of the tetrazole converts hydrophilic compounds to lipophilic compounds which are suitable for transdermal delivery. The invention also describes 4(5)-imidazole dialkylated derivatives with the biphenyl tetrazole trityl moiety attached to both nitrogen positions 1 and 3 of the imidazole ring.

The four distinct steps: tritylation, alkylation, detritylation of two trityl groups and selective chlorotritylation of tetrazole, can be carried out in a one-pot synthesis as follows:

Organic phase (DCM) containing N-1 tritylated imidazole derivative 14, 15, 27 was washed with 5% $NaHCO_3$, $H_2O$ and dried with anhydrous sodium sulfate. Addition of bromo derivative 10 or 11 in the dried organic phase containing N-1 trityl imidazole resulted in alkylation at N-3 position (14a, 15a, 14b, 27a). Detritylation in same pot was carried out using 50% TFA in DCM. Evaporation of solvent and TFA afforded an oily material (16, 17, 24, 28). Products 16 and 17 were dissolved in DCM followed by addition of DIPEA and chlorotrityl chloride for selective chlorotritylation of tetrazole moiety. The mixture was washed with 5% NaHCO3 and H2O. Final imidazole alkylated products 18, 19 were obtained by purification with flash column chromatography.

The critical key intermediate substance 18 resulting after selective alkylation of imidazole N1 (for short, high synthesis of compound 20) can indeed be achieved from material 4(5) butyl or alkyl imidazole. While the primary target requires at least 6 steps, this key intermediate 18 can be achieved in a one-pot synthesis, which includes four steps, followed by hydroxymethylation and routine detritylation to get the primary compound. An example is the one pot synthesis of lipophylic 20 through the critical key intermediate substance 18.

One aspect of the invention relates to a process for preparing a compound of formula I as defined above, said process comprising the steps of:

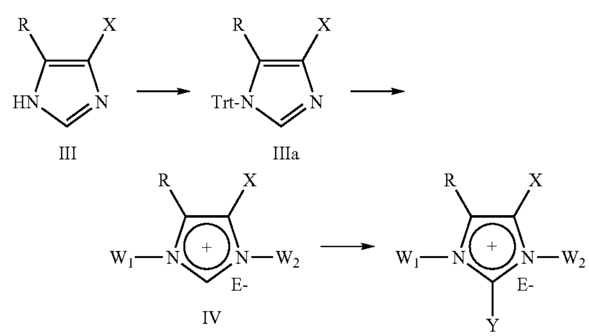

III IIIa IV I (i) reacting a compound of formula III with trityl chloride to form a compound of formula IIIa;

(ii) reacting said compound of formula IIIa with Br—$(CH_2)_n$—K—Z—$Z_1$ to form a compound of formula IV;

(iii) converting said compound of formula IV to a compound of formula I.

Preferably, step (ii) comprises reacting said compound of formula IIIa with Br—$(CH_2)_n$—K—Z'—$Z'_1$, wherein Z' is tetrazoyl and is trityl, chlorotrityl, benzyl or $CH(Ph)_2$, to form a compound of formula IVa, IVa

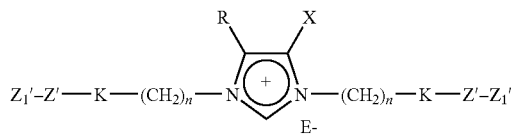

and converting said compound of formula IVa to a compound of formula I.

In one preferred embodiment, $Z'_1$ is trityl.

In another preferred embodiment, $Z'_1$ is benzyl.

In one preferred embodiment, step (ii) is carried out in the presence of potassium carbonate, and the ratio of Br—$(CH_2)_n$—K—Z'—$Z'_1$ to compound IIIa is at least 3:1.

More preferably, step (iii) comprises the steps of:

IVb

IVc

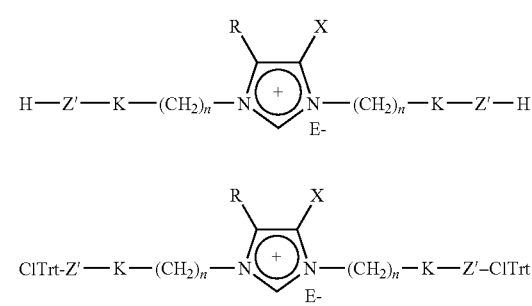

(iii)(a) converting said compound of formula IVa to a compound of formula IVb;
(iii)(b) treating said compound of formula IVb with 2-chlorotrityl chloride to form a compound of formula IVc;
(iii)(c) converting said compound of formula IVc to a compound of formula I.

Preferably, step (iii)(c) comprises treating said compound of formula IVc with formaldehyde to form a compound of formula I, wherein Y is $CH_2OH$.

Preferably, steps (ii) and (iii) are carried out in a one-pot procedure.

Another aspect of the invention relates to a process for preparing a compound of formula II as defined above, said process comprising the steps of:

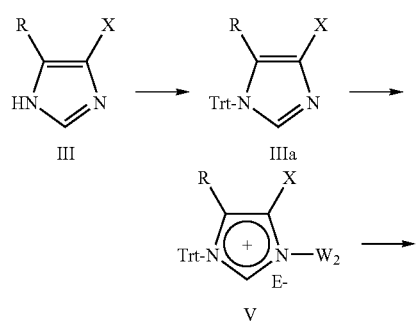

VI

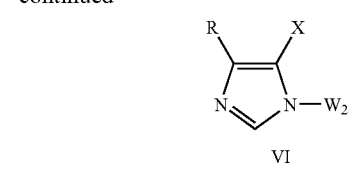

II

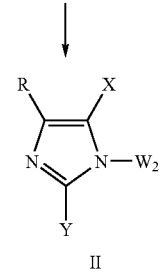

(i) reacting a compound of formula III with trityl chloride to form a compound of formula IIIc:
(ii) reacting said compound of formula IIIc with Br—$(CH_2)_n$—K—Z—$Z_1$ to form a compound of formula V;
(iii) converting said compound of formula V to a compound of formula VI;
(iv) converting said compound of formula VI to a compound of formula II.

Preferably, for this embodiment, step (ii) comprises reacting said compound of formula IIIa with Br—$(CH_2)_n$—K—Z'—$Z'_1$, wherein Z' is tetrazoyl and $Z'_1$ is trityl, chlorotrityl, benzyl or $CH(Ph)_2$, to form a compound of formula Va, Va VIa

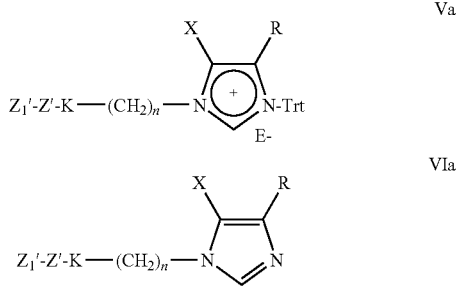

and converting said compound of formula Va to a compound of formula VIa, and converting said compound of formula VI to a compound of formula II.

In one preferred embodiment, $Z'_1$ is trityl.

In another preferred embodiment, $Z'_1$ is benzyl.

Preferably, for this embodiment, step (ii) is carried out in the presence of potassium carbonate, and the ratio of Br—$(CH_2)_n$—K—Z'—$Z'_1$ to compound IIIa is about 1:1.

Preferably, step (iv) comprises the steps of:

VIb

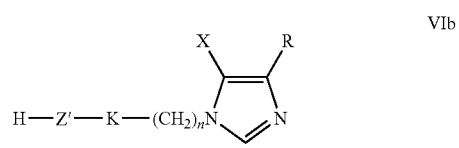

-continued

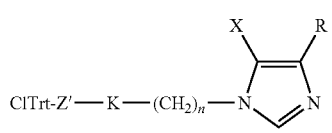
VIc (iv)(a) converting said compound of formula VIa to a compound of formula VIb;
(iv)(b) treating said compound of formula VIb with 2-chlorotrityl chloride to form a compound of formula VIc;
(iv)(c) converting said compound of formula VIc to a compound of formula II.

Preferably, step (iv)(c) comprises treating said compound of formula VIc with formaldehyde to form a compound of formula I, wherein Y is $CH_2OH$.

Compounds of formula III may be produced by an analagous method.

Advantages of Cltr Compared to Trt

The Cltr is less stable as protecting group in nitrogen bearing groups (primary and secondary amines, imidazole, tetrazoles, etc) compared to the trityl group (Barlos and Gatos et al 1999). Introducing a chlorine atom into the phenyl ring of trityl group produces more stable carbonations through hyperconjugation after deprotection, compared to trityl carbonations. This group is therefore more acid labile compared to the trityl group and more easily removed in the in vivo environment to afford active substance 22. Thus, the high difference in activity between 20 and 22 in favor of trityl free 22 is expected for the in vitro experiments. Lipophilic tetrazole trityl compound 20 cannot bind to AT1 receptors to the same extend as 22 does, as the pharmacophoric tetrazole group is protected with the chlorotrityl moiety.

The smallest difference in activity between 20, 22 (again in favor of 22) in the in vivo experiment can be explained through the slow deprotection of highly acid sensitive Cltr 25 moiety in 20, resulting in free tetrazole compound 22, which is the active component.

The invention provides the synthesis of analogues that differ in the substitution pattern around the imidazole ring when compared with Losartan. Thus, the alkyl chain and hydroxymethyl group possess a different topographical position in an attempt to optimize the mimicry of lipophilic superimposition of the butyl chain with the isopropyl group of $Ile^5$ in AII and to probe the significance of the position of the hydroxymethyl group conversion to carboxylate in the active metabolite. Also, introducing an additional biphenyl (monophenyl) tetrazole moiety, as in the dialkylated derivatives, increases the negative charge, thereby improving the affinity for the Angiotensin II receptor. Alkylation is achieved selectively in the N-1 position of the 4(5)-alkyl imidazole ring or to both the N-1 and N-3 nitrogen atoms of the ring using bromobiphenyl intermediates. An established procedure is employed in the preparation of biphenyl intermediates 5, 10 and 11 (Scheme 1). Other bromobiphenyl intermediates are used in this invention to alkylate 4(5) imidazole. Examples of alkylations are provided below.

Selective introduction of a trityl group to the N-1 position of the 4(5)-butylimidazole ring using Barlos's methods is a major step in facilitating the subsequent selective alkylation of the imidazole ring at position N-1. The synthesis of potent AII non-peptide mimetics 22 and 23 is depicted in Scheme 2. Firstly, compounds 14 and 15 are prepared by tritylation of 4(5)-butylimidazole with trityl chloride. This reaction selectively introduces a trityl group at position N-1 of the imidazole ring. Protection of the N-3 position of the imidazole by the trityl moiety allows the next step of selective alkylation of the ring at position N-1. Alkylation reagents can be varied according to designed targets, allowing the introduction of other desired pharmacophoric groups at the N-3 position. In this work, the alkylation reagent used was the brominated biphenyltetrazole derivative 10 depicted in Scheme 1. Alkylation of 14 and 15 with bromide 10, carried out at room temperature for several hours, followed by simultaneous deprotection of both trityl groups, provided compounds 16 and 17 as TFA salts. These salts were neutralized with DIPEA, prior to selective chlorotritylation of the tetrazole moiety to yield 18 and 19 respectively. Protection of tetrazole by 2-chlorotrityl group was a necessary step before hydroxymethylation. Selective hydroxymethylation of 1,5-disubstituted imidazole derivatives 18 and 19 at position 2 afforded compounds 20 and 21 with yields of 37% and 47% respectively. Detritylation was readily achieved by treatment of compounds 20 and 21 with 50% TFA to afford 22 and 23 respectively. A more efficient synthesis of compound 22 was achieved, utilizing bromomethyltetrazole derivative 11, through debenzylation of 25 via the shorter route depicted in Scheme 2. Benzimidazole 26 was also employed to illustrate this general alkylation protocol (Scheme 3). Tritylation of 26 with trityl chloride led to compound 27. Compound 27 was subsequently alkylated, detritylated and hydroxymethylated to yield 29. In the case of hydroxymethylation of benzyl-protected biphenyltetrazolyl imidazoles, yields were generally good (50-70%). By employing benzyl protection on the tetrazole, higher temperatures (140° C.) could be applied in the hydroxymethylation reaction. The benzyl group is far more thermally stable compared to the 2-chlorotrityl protecting group. The latter began to cleave at temperatures above 105° C. at which an equilibrium of optimum hydroxymethylatation/minimum detritylation was achieved. The benzyl group was removed cleanly with hydrogenolysis using 10% palladium in carbon to yield final compound 30.

In particular, the present invention provides the efficient synthesis of Angiotensin II receptor antagonists in which: (a) the hydroxymethyl group and butyl groups attached to imidazole ring have different topographical positions in comparison with Losartan. According to our superimposition model, such a topographical change would bring the butyl chain into closer spatial vicinity with the isopropyl group of $Ile^5$, (b) the tetrazole group is protected by trityl moieties or benzyl derivatives which increase lipophilicity, bioavailability and duration; (c) the butyl group is substituted by methyl, fused benzo and alkylester groups to 4,5-positions of imidazole to further confirm the role of the butyl or ester group in activity, (d) the imidazole ring of 4(5)-alkyl imidazole is dialkylated to increase the negative charge required for better affinity.

Structure activity relationships with bioactivity: Several classes of imidazole based AII antagonists were examined. Examples of these include those possessing butyl or methyl alkyl chains at position 5 and fused phenyl groups at positions 4, 5 of the imidazole ring. The biological activities shown in the synthetic compounds can be explained by the superimposition models applied to their design. Butyl derivatives 18, 20, 22, 25 are more potent compared to methyl derivatives 21, 23, indicating that this chain is probably an optimum to mimic the isopropyl group of the Ile$^5$ in Sarmesin. Simulation studies based on our receptor model conformation suggest an overlapping of the butyl group with the Ile side chain in AII. The butyl group is also a better electron donor through inductive effects compared to the methyl group, which may be another factor for maximum affinity. Benzimidazole derivatives 28, 29, 30 in which the alkyl group of imidazole is replaced by a fused benzo group to the imidazole, are even less potent, indicating the importance of an electron donor alkyl group for maximum activity. Resonance effects of the benzo group reduce the electron density of imidazole ring, which is a prerequisite for higher activity.

Among the butyl imidazole derivatives, those with a hydroxymethyl group at position 2 (22, 20, 25) are more potent compared to 18, which lacks this moiety. In Losartan, this group is converted to carboxylate affording active metabolite EXP 3174. Our superimposition studies show that the imidazole carboxylate mimics the phenolate of tyrosine, an important pharmacophore for activity, as it provides a negative charge for receptor affinity. Furthermore, compounds 22, 20, 25 exhibited similar activities in our assays, with 22 slightly superior in activity. Possible deprotection of 20 and 25 analogues bearing chlorotrityl and benzyl tetrazole protection respectively, indicate that they may act as prodrugs of 20. Their in vivo potency in the order 20>2 5 indicates a different deprotection rate to the free tetrazole in the in vivo environment, which accounts for the observed different potency. The chlorotrityl group is an acid sensitive group easily removed in acid environment (Barlos et al.$^{34-37}$), while the benzyl group is a more stable protecting group which can also be cleaved, albeit with more difficulty, to the free tetrazole in the chemical and enzymic environment of the in vivo assay.

In vitro binding studies showed that 22 has a similar magnitude of affinity as the prototype Losartan, while 20 has lower affinity, indicating that a free tetrazole group is necessary for binding with the AT1 receptor. Overall these findings suggest that the use of the acid sensitive chlorotrityl group as the tetrazole protecting group results in slow deprotection in the in vitro experiment and faster deprotection in the in vivo experiment, which may account for the difference in binding affinity and similar in vivo activity for compounds 22 and 20. The above SAR findings also suggest that the interchange of topographical positions of the hydroxymethyl group with the butyl chain has no significant impact on the activity of the molecule.

The present invention is further described with reference to the following non-limiting examples.

EXAMPLES

1. Experimental Methods

Abbreviations

Abbreviations used are in accordance with the rules of the IUPAC-IUB Commission on Biochemical Nomenclature (*Eur. J. Biochem.* 1984, 138, 9; *J. Biol. Chem.* 1989, 264, 663). Abbreviations: AcN, acetonitrile; DCM, methylene chloride; AcOH, acetic acid; Et2O, diethyl ether; EtOAc, ethyl acetate; THF, tetrahydrofuran; TFA, trifluoroacetic acid; TEA, triethylamine; DMSO, dimethyl sulfoxide; DIPEA, N,N'-isopropylethylamine; NBS, N-bromosuccinimide.

Analytical Methods MP/NMR/HPLC

Melting points were determined with an Electrothermal 9100 melting point apparatus and are uncorrected. Infrared spectra were recorded on a Perkin-Elmer 1 6PC spectrophotometer. 1H (400 MHz) NMR spectra were obtained in CDCl3 or DMSO-d6 on a Bruker Avarice DPX-400 spectrometer. Chemical shifts are given in values (ppm) using tetramethylsilane as the internal standard, and coupling constants (J) are given in hertz (Hz). Liquid chromatography was performed with a forced flow (flash chromatography) of the indicated solvent system on silica gel (230-400 mesh, Merck). All the intermediate and final products were checked for purity on a Waters HPLC system equipped with a 600E system controller and a 996 Photodiode Array Detector. Analytical runs were performed on a reversed-phase column (Lichrosorb C18, 250×4 mm) using a linear gradient of acetonitrile (AcN) in water, 0.1% aqueous preparative trifluoroacetic acid (TFA) at a flow rate 1 mL/min. Microanalyses were performed on a Carlo Erba EA 1108 CHNS elemental analyzer.

Preparative Methods

The final products (22) and (33) were purified on the same HPLC system. A Lichrosorb RP-18 reversed-phase preparative column (250×10 mm) with 7 m packing material was used. The crude products were dissolved in MeOH, clarified by centrifugation and the solutions were injected through a Rheodyne 7125 injector with a 500 L sample loop. Separations were achieved with a stepped linear gradient of acetonitrile (AcN), (0.1% TFAaq) in water (0.1% TFAaq) over 60 min at a flow rate of 3 mL/min. The fluent was monitored at 230 and 254 nm and the elution time of the major products was typically in the region of 25-30 min. Fractions containing the major product peak were pooled and acetonitrile was removed using a rotary evaporator. After lyophilization, the products were stored at −20° C. Starting materials were purchased from Aldrich and were used as received.

NMR Spectroscopy—Experimental Methods for Selected Compounds

Compound 22 was dissolved in DMSO solvent (5 mg in 0.4 mL) with TMS used as the chemical shift reference and 1D 1H NMR and 2D experiments (DQF-COSY, ROESY) were performed using Bruker AC 300 instrument at 298 K. All data were collected using pulse sequences and phase-cycling routines provided in the Bruker software.

Molecular Modeling. Computer calculations were performed on a Silicon Graphics using QUANTA software purchased from Molecular Simulation Incorporated (MSI). 22 was first minimized to reach an energy minimum and then subjected to Molecular Dynamics. The dielectric constant ( ) set in minimization and Molecular Dynamics was 45. A time step of 1 fs was employed for the MD simulation. The simulation protocol consisted of two minimization cycles (steepest descent and conjugate gradients), first with the solute fixed and then with all the atoms allowed to move freely. The NMR derived distance restraints with a force constant of 10 Kcal mol-1 Å-1 were applied during the complete simulation. A Monte Carlo conformational search without constraints aided Molecular Dynamics experiment under constraints in an attempt to expand the conformational space and increase the probability to generate lower energy conformers, which agree with the ROE data.

Further details of the synthesis are presented in the following reaction schemes.

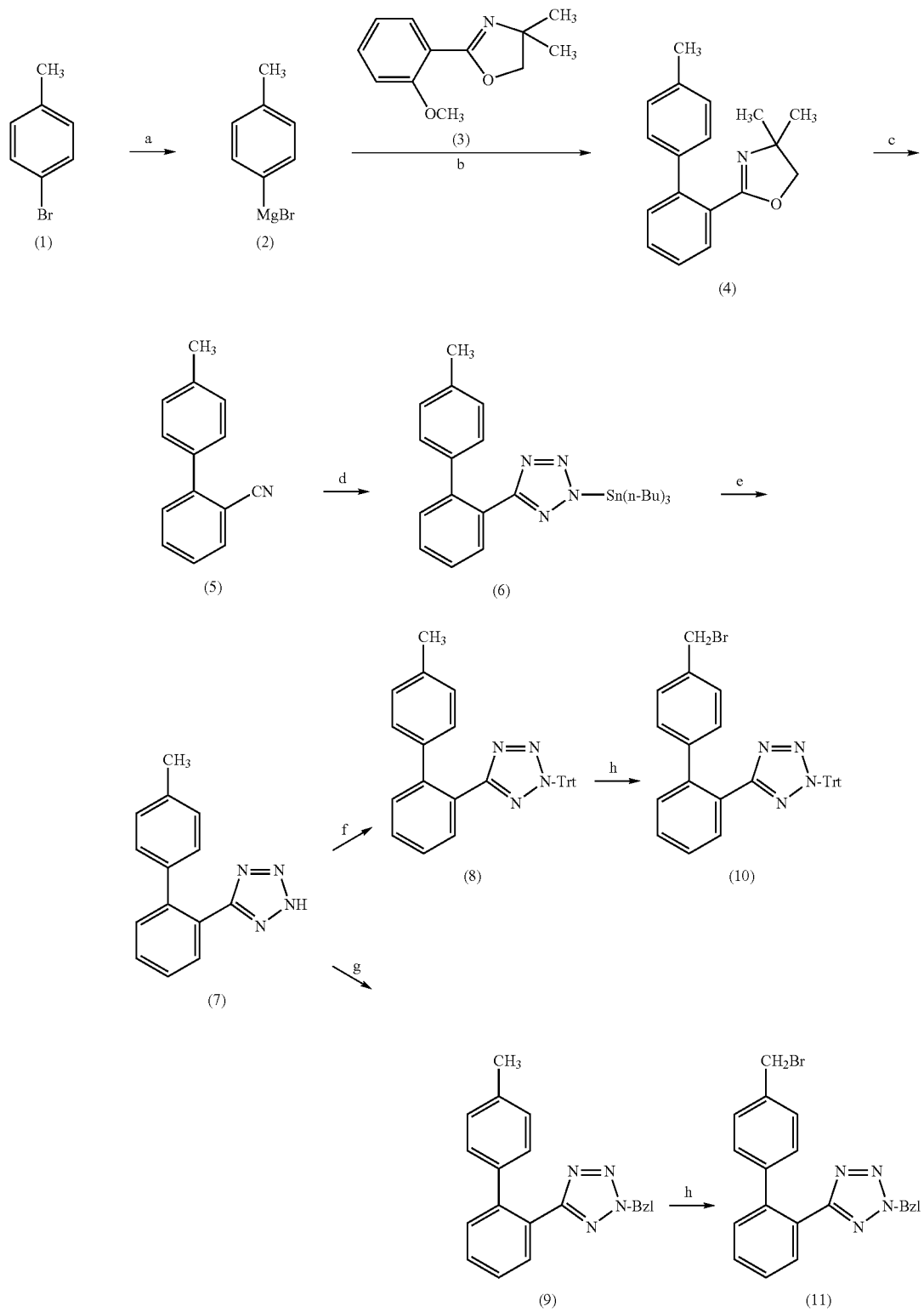
Scheme 1: Reagents And Conditions: (a) Mg, THF, Room Temperature, 2 h; (b) 4,4-Dimethyl-2-(2-Methoxyphenyl) Oxazoline (3), THF, Room Temperature, 3 h; (c) Py/POCl3, 10 0 c To 100 0 c, 3 h; (d) NaN3, (N-Bu)3SnCl, Tol, 110 0 c, 96 h; (e) 2 n HCl in H2O:THF 1:3, Room Temperature, 16 h; (f) Trt-Cl, DIPEA, DCM, Room Temperature, 1 h; (g) Bzl-Br, DIPEA, DCM, Room Temperature, 1 h; (h) NBS, DBP, CCl4, Reflux, 6 h.

Scheme 2
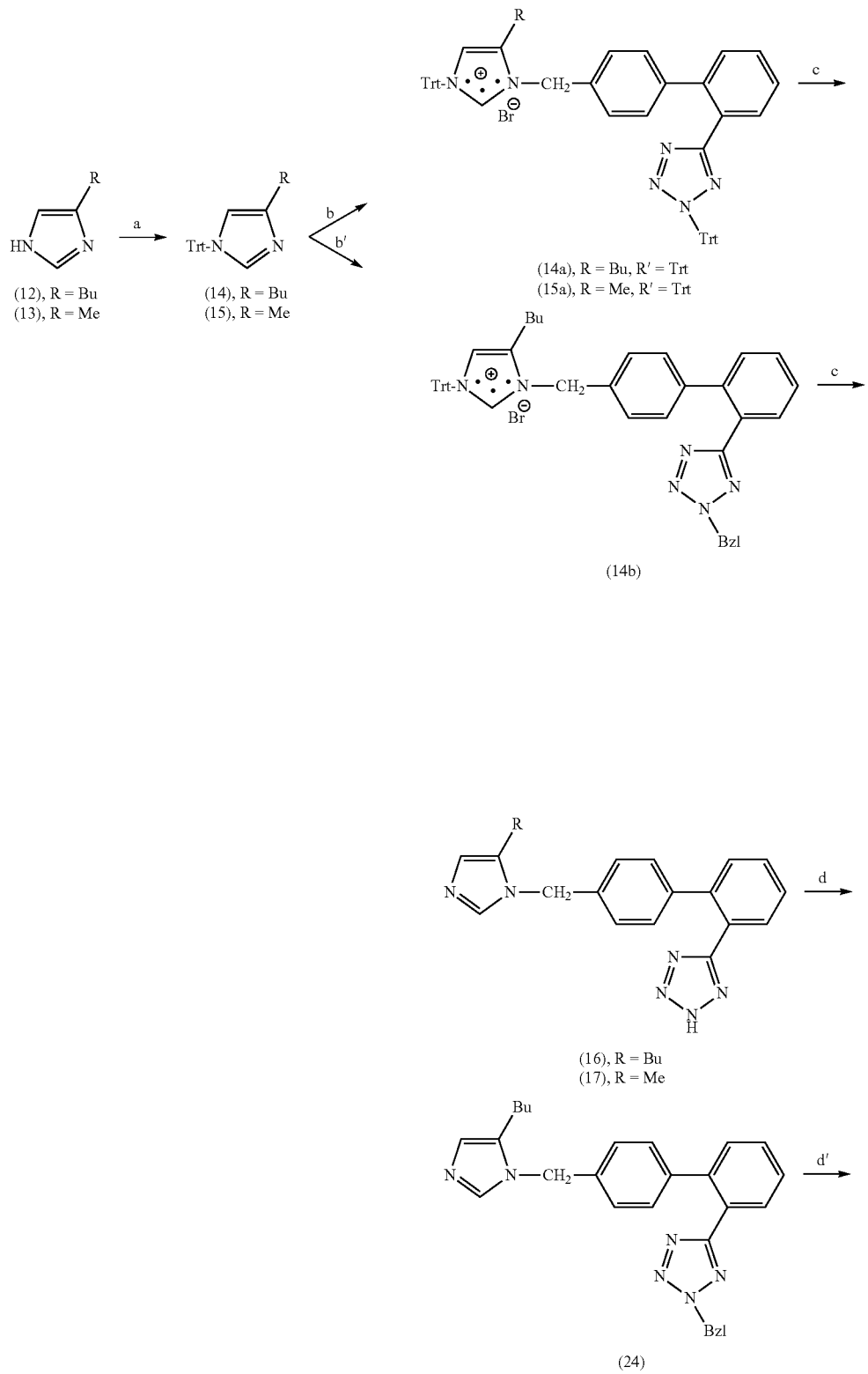

-continued

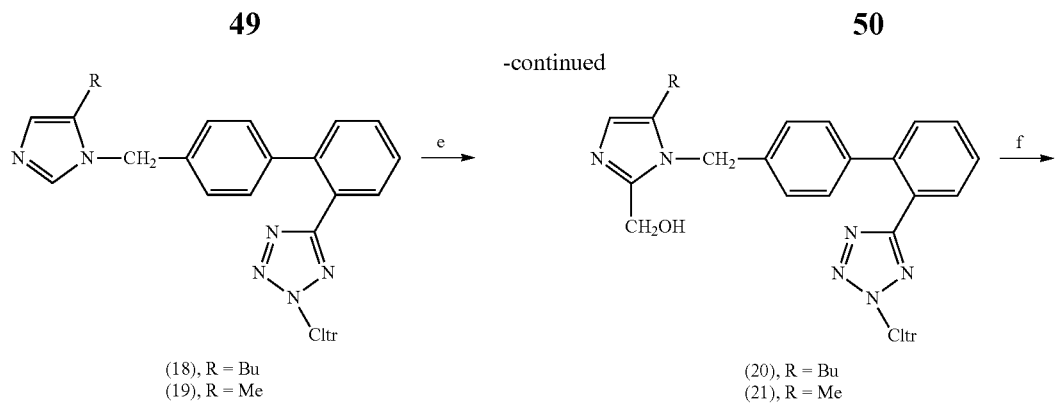

(18), R = Bu
(19), R = Me (20), R = Bu
(21), R = Me

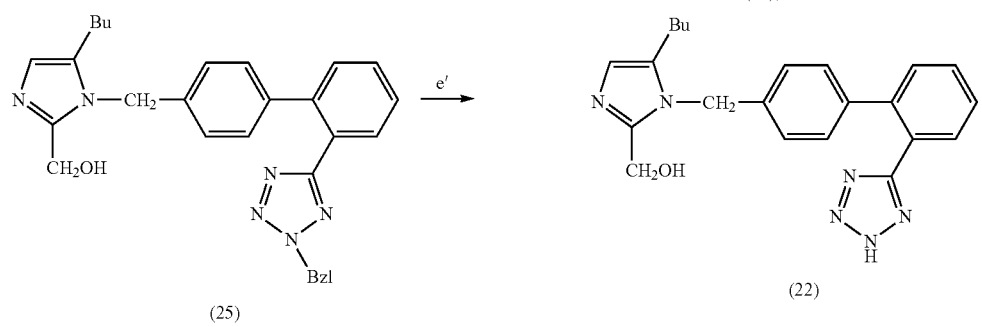

(25)

(22)

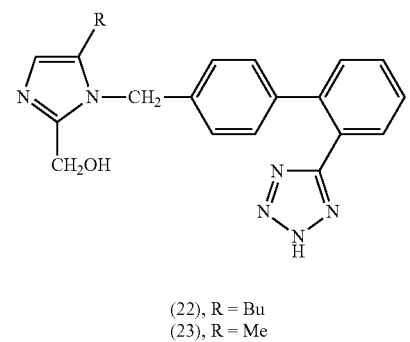

(22), R = Bu
(23), R = Me

Scheme 2: Reagents And Conditions: (a) Trt-Cl, TEA, DCM, Room Temperature, 1 h; (b) Biphenyltetrazole (10), DCM; (b') Biphenyltetrazole (11); (c) 1.50% TFA in DCM, Et3SiH, Room Temperature, 1 h; 2. DIPEA, DCM, Room Temperature, ½ h; (d) Cltr-Cl, DIPEA, DCM, Room Temperature, 1 h; (d') HCHO 37%, 140 0 C, 8 h; (e) HCHO 37%, DIPEA, 105 0 C, 16 h; (e') 10% Pd/C, AcOH, H2, Room Temperature, 24 h; (f) 50% TFA in DCM, Et3 SiH, Room Temperature, 1 h.

Scheme 3

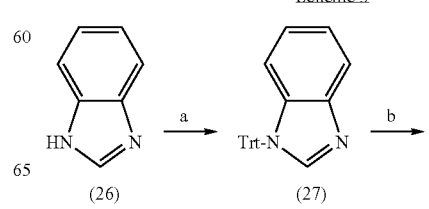

(26) (27)

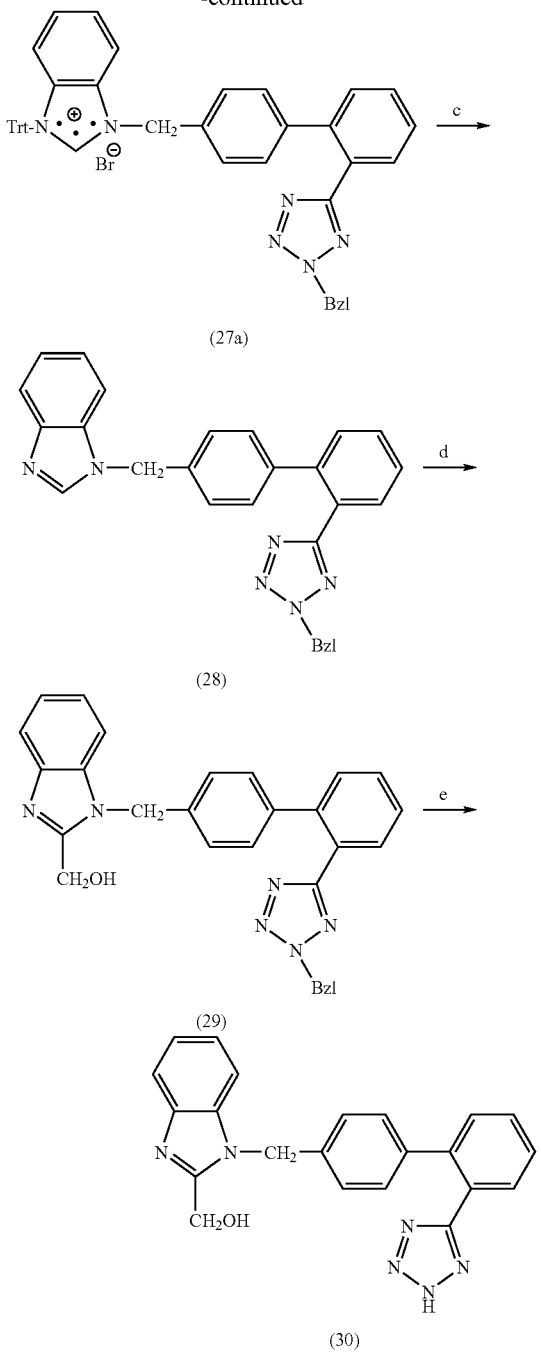

(27a)

(28)

(29)

(30)

Scheme 3: Reagents And Conditions: (a) Trt-Cl, TEA, DCM, room Temperature, 1 h; (b) Biphenyltetrazole (11), DCM; (c) 1.50% TFA in DCM, Et3SiH, room Temperature, 1 h; 2. DIPEA, DCM, Room Temperature, ½ h; (d) HCHO 37%, 140 0 c, 8 h; (f) 10% Pd/C, AcOH, H2, room Temperature, 24 h.

Synthetic Procedures

General Procedure for the protection of N-3 of imidazole ring with the triphenylmethyl-group. To a solution of the desired imidazole derivative (12), (13) or (26) (80.5 mmol) in anhydrous DCM (240 mL) was added slowly TEA (27.9 mL, 201.25 mmol) and triphenylmethyl chloride (25.2 g, 88.5 mmol). The mixture was allowed to stir at room temperature for 1 h. The solvent was removed under vacuum, water was added and the contents were extracted with EtOAc. The organic layer was washed with 5% NaHCO$_3$ (×3) and water (×2), dried over anhydrous sodium sulfate, filtered and the solvent was removed to afford the compounds (14), (15), (27) which were further purified by crystallization from diisopropyl ether.

3-(Triphenylmethyl)-5-butylimidazole (14): yield 88%; mp 97-100 0 C; 1H NMR (CDCl3) 7.35-7.14 (m, 16H), 6.52 (s, 1H), 2.55 (t, J=7.8 Hz, 2H), 1.62 (p, J=7.6 Hz, 2H), 1.36 (h, J=7.6 Hz, 2H), 0.92 (t, J=7.4 Hz, 3H). 3-(Triphenylmethyl)-5-methylimidazole (15): yield 89%; mp 220-222 0 C; 1H NMR (CDCl3) 7.35-7.16 (m, 16H), 6.54 (s, 1H), 2.22 (s, 3H). 1-(Triphenylmethyl)-benzimidazole (27): yield 85%; mp 170-172 0 C; 1H NMR (CDCl3) 7.79-7.15 (m, 19H), 7.89 (s, 1H).

General Procedure for the alkylation at N-1 of N-3 tritylated imidazole derivatives with the brominated biphenyltetrazole derivatives and the removal of trityl-groups. To a solution of the desired tritylated imidazole derivative (14), (15) or (27) (27.2 mmol) in anhydrous DCM (80 mL) was added the appropriate brominated biphenyltetrazole protected derivative (10) (16.6 g, 30 mmol) or (11) (12.2 g, 30 mmol). The mixture was allowed to stir at room temperature for 96 h. The solvent was removed under vacuum and was added a solution of 50% TFA in DCM (70 mL) and triethylsilane (8.8 mL, 54.4 mmol). After 1 h stirring at room temperature the reaction mixture was concentrated under vacuum. Trituration of the crude products with Et$_2$O afforded (16) and (17). The workup for the other two products continued as described below: The crude products were dissolved in DCM (60 mL) and DIPEA (9.35 mL, 55 mmol) was slowly added. The resulting mixtures were stirred for 0.5 h at room temperature. The solvent was removed under vacuum, EtOAc was added and the organic phase was washed with 5% citric acid (×3) and water (×2), dried over anhydrous sodium sulfate, filtered and the solvent was removed to afford the compounds (24) and (28), which were further purified by trituration with Et2O.

Trifluoroacetic salt of 5-butyl-1-[[2'-(1H-tetrazol-5-yl)biphenyl-4-yl]methyl]imidazole (16): yield 53%; mp 68-70 0 C; 1H NMR (CDCl3) 8.12-7.08 (m, 10 H), 5.08 (s, 2 H), 2.75 (t, J=7.6 Hz, 2 H), 1.75 (p, J=7.6 Hz, 2 H), 1.51 (h, J=7.2 Hz, 2H), 1. 02 (t, J=7.2 Hz, 3 H).

Trifluoroacetic salt of 5-methyl-1-[[2'-(1H-tetrazol-5-yl) biphenyl 4-yl]methyl]imidazole (17): yield 60%; mp 107-109 0 C; 1H NMR (CDCl3) 8.38-7.12 (m, 10 H), 5.12 (s, 2 H), 2.41 (s, 3H).

1-[[2'-[(N-benzyl)tetrazol-5-yl]biphenyl-4-yl]methyl]-5-butylimidazole (24): yield 61%; mp 69-71 0 C; 1H NMR (CDCl3) 7.65-6.78 (m, 13 H), 5.04 (s, 2 H), 4.84 (s, 2 H), 2.37 (t, J=7.6 Hz, 2 H), 1.54 (p, J=7.6 Hz, 2 H), 1.35 (h, J=7.6 Hz, 2 H), 0.89 (t, J=7.6 Hz, 3 H).

1-[[2'-[(N-benzyl)tetrazol-5-yl]biphenyl-4-yl]methyl] benzimidazole (28): yield 55%; mp 62-64 0 C; 1H NMR (CDCl3) 7.98-6.74 (m, 18H), 5.35 (s, 2 H), 4.81 (s, 2 H).

General Procedure for the protection of tetrazole with the 2-chloro-triphenylmethyl-group. To a solution of the desired trifluoroacetic salt (16) or (17) (8.1 mmol) in anhydrous DCM (25 mL) was added slowly DIPEA (5.6 ml, 32.4 mmol) and 2-chloro-triphenylmethyl chloride (2.8 g, 8.9 mmol). The mixture was allowed to stir at room temperature for 1 h. The solvent was removed under vacuum, water was added and the contents were extracted with EtOAc. The organic layer was washed with 5% citric acid (×3) and water (×2), dried over anhydrous sodium sulfate, filtered and concentrated under vacuum to provide the crude product which purified with column chromatography on silica gel (elution for product (18): 3% MeOH/CHCl3, elution for product (19): 6% MeOH/CHCl3).

5-Butyl-1-[[2'-[[N-(2-chloro-triphenylmethyl)]tetrazol-5-yl]biphenyl-4-yl]methyl]imidazole (18): yield 62%; mp 87-88 0 C; 1H NMR (CDCl3) 8.33-6.71 (m, 10 H), 5.03 (s, 2 H), 2.44 (t, J=7.6 Hz, 2 H), 1.54 (p, J=7.6 Hz, 2H), 1.34 (h, J=7.4 Hz, 2H), 0.89 (t, J=7.4 Hz, 3 H).

5-Methyl-1-[[2'-[[N-(2-chloro-triphenylmethyl)]tetrazol-5-yl]biphenyl-4-yl]methyl]imidazole (19): yield 72%; mp 100-102 0 C; 1H NMR (CDCl3) 7.53-6.72 (m, 24 H), 5.03 (s, 2 H), 1.98 (s, 3 H).

General Procedure for hydroxymethylation of the imidazole ring of compounds (18), (19). A mixture of the desired compound (18), or (19) (0.94 mmol), formaldehyde solution 37% (0.25 mL, 3.3 mmol) and DIPEA (0.4 mL, 2.35 mmol) was heated in a Curtius tube for 16 h at 105 0 C. After cooling the reaction was partitioned between water and EtOAc. The organic phase was washed with 5% citric acid (×3) and water (×2), dried over anhydrous sodium sulfate, filtered and concentrated under vacuum to provide the crude product, which purified with column chromatography on silica gel (elution: 3.5% MeOH/CHCl3).

5-Butyl-2-hydroxymethyl-1-[[2'-[[N-(2-chloro-triphenyl-methyl)]tetrazol-5yl]biphenyl-4-yl]methyl]imidazole (20): yield 37%; mp 191-193 0 C; 1H NMR (CDCl3) 7.95-6.70 (m, 23 H), 5.04 (s, 2 H), 4.45 (s. 2 H), 2.30 (t, J=7.6 Hz, 2H), 1.50 (p, J=7.6 Hz, 2 H), 1.27 (h, J=7.4 Hz, 2 H), 0.85 (t, J=7.4 Hz, 3 H).

5-Methyl-2-hydroxymethyl-1-[[2'-[[N-(2-chloro-triphenylmethyl)]tetrazol-5-yl]biphenyl-4-yl]methyl]imidazole (21): yield 47%; mp 156-158 0 C; 1H NMR (CDCl3) 7.96-6.72 (m, 23 H), 5.08 (s, 2 H), 4.59 (s, 2 H), 1.99 (s, 3 H).

General Procedure for hydroxymethylation of the imidazole ring of compounds (24), (28). A mixture of the desired compound (24), or (28) (0.33 mmol) and formaldehyde solution 37% (0.1 mL, 1.17 mmol) was heated in a Curtius tube for 8 h at 140 0 C. After cooling the reaction was partitioned between water and ethyl acetate. The organic extracts were dried over anhydrous sodium sulfate, filtered and the solvent removed under vacuum leaving a yellow oil. The crude product (25) was purified on a HPLC system. A linear gradient from 35 to 70% B over 65 min was used. The product (29) was purified with column chromatography on silica gel (elution: 3.5% MeOH/CHCl3).

1-[[2'-[(N-benzyl)tetrazol-5-yl]biphenyl-4-yl]methyl]-5-butyl-2hydroxymethyl imidazole (25): yield 70%; 1H NMR (CDCl3) 7.66-6.82 (m, 14 H), 5.24 (s, 2 H), 4.96 (s. 2 H), 4.81 (s. 2 H), 2.47 (t, J=7.6 Hz, 2 H), 1.57 (p, J=7.2 Hz, 2 H), 1.38 (h, J=7.2 Hz, 2 H), 0.92 (t, J=7.2 Hz, 3 H).

1-[[2'-[(N-benzyl)tetrazol-5-yl]biphenyl-4-yl]methyl]-2-hydroxymethyl benzimidazole (29): yield 50%; mp 62-63 0 C; 1H NMR (CDCl3) 7.82-6.75 (m, 17 H), 5.46 (s, 2 H), 4.96 (s, 2 H), 4.82 (s, 2 H).

General procedure for the removal of 2-chloro-triphenylmethyl-group. In a quantity of the desired hydroxymethylated imidazole derivative (20) or (21) (0.3 mmol) was added a solution of 50% TFA in DCM (0.8 mL) and triethylsilane (0.05 mL, 0.3 mmol). After 1 h stirring at room temperature the reaction mixture was concentrated under vacuum and the residue was crystallized from Et2O to afford (22) and (23).

Trifluoroacetic salt of 5-butyl-2-hydroxymethyl-1-[[2'-(1H-tetrazol-5-yl)biphenyl-4-yl]methyl]imidazole (22): yield 80%; mp 109-111 0 C; 1H NMR (CDCl3) 7.84-6.93 (m, 9 H), 5.32 (s, 2 H), 4.75 (br, s, 2 H), 2.59 (t, J=7.4 Hz, 2 H), 1.64 (p, J=7.2 Hz, 2 H), 1.41 (h, J=7.2 Hz, 2H), 0.92 (t, J=7.4 Hz, 3 H). Trifluoroacetic salt of 5-methyl-2-hydroxymethyl-1-[[2'-(1H-tetrazol-5-yl)biphenyl-4-yl]methyl]imidazole (23): yield 82%; mp 76-78 0 C; 1H NMR (CDCl3) 7.84-6.94 (m, 9 H), 5.33 (s, 2 H), 4.77 (s, 2 H), 2.31 (s, 3 H).

General procedure for the removal of benzyl-group. To a solution of the desired compound (25) or (29) (0.42 mmol) in AcOH (3 mL) was added 10% palladium on carbon (0.06 g) as catalyst and hydrogen is bubbled through the solution. After 24 h stirring at room temperature the reaction mixture was filtered to remove the catalyst and the filtration was concentrated under vacuum. The residues were purified on a HPLC system. For product (22) was used a linear gradient from 20 to 80% B over 60 min. For product (30) was used a linear gradient from 20 to 50% B over 60 min.

Trifluoroacetic salt of 5-butyl-2-hydroxymethyl-1-[[2'-(1H-tetrazol-5-yl)biphenyl-4-yl]methyl]imidazole (22): yield 75%; mp 109-111 0 C; 1H NMR (CDCl3) 7.84-6.93 (m, 9 H), 5.32 (s, 2 H), 4.75 (br, s, 2 H), 2.59 (t, J=7.4 Hz, 2 H), 1.64 (p, J=7.2 Hz, 2 H), 1.41 (h, J=7.2 Hz, 2H), 0.92 (t, J=7.4 Hz, 3 H).

Trifluoroacetic salt of 2-hydroxymethyl-1-[[2'-(1H-tetrazol-5-yl)biphenyl-4-yl]methyl]benzimidazole (30): yield 72%; 1H NMR (DMSO-d6) 7.66-7.01 (m, 12 H), 5.59 (s, 2 H), 4.89 (s, 2 H).

One Pot Synthesis of 1,5-disubstituted imidazoles

Four distinct steps: Tritylation, alkylation, detritylation of two trityl groups and selective chlorotritylation of tetrazole, could be carried out in a one-pot synthesis as follows: Organic phase (DCM) containing N-1 tritylated imidazole derivative 14, 15, 27 was washed with 5% NaHCO3, H2O and dried with anhydrous sodium sulfate. Addition of bromo derivative 10 or 11 in the dried organic phase containing N-1 trityl imidazole resulted in alkylation at N-3 position (14a, 15a, 14b, 27a). Detritylation in same pot was carried out using 50% TFA in DCM. Evaporation of solvent and TFA afforded an oily material (16, 17, 24, 28). Products 16 and 17 were dissolved in DCM followed by addition of DIPEA and chlorotrityl chloride for selective chlorotritylation of tetrazole moiety. The mixture was washed with 5% NaHCO3 and H2O. Final imidazole alkylated products 18, 19 were obtained by purification with flash column chromatography.

1. Synthesis of Lipophilic Tetrazole Trityl Chloride Derivative 6

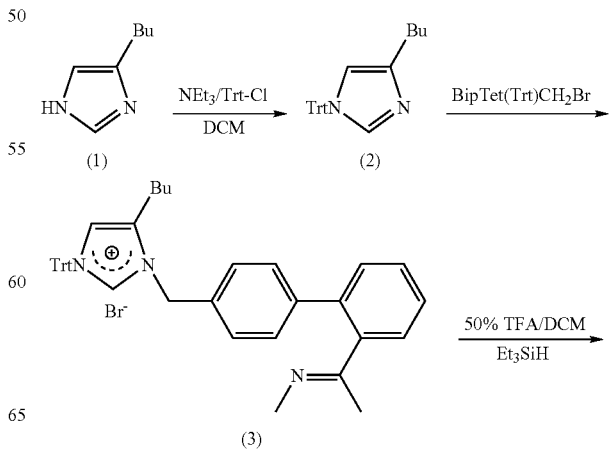

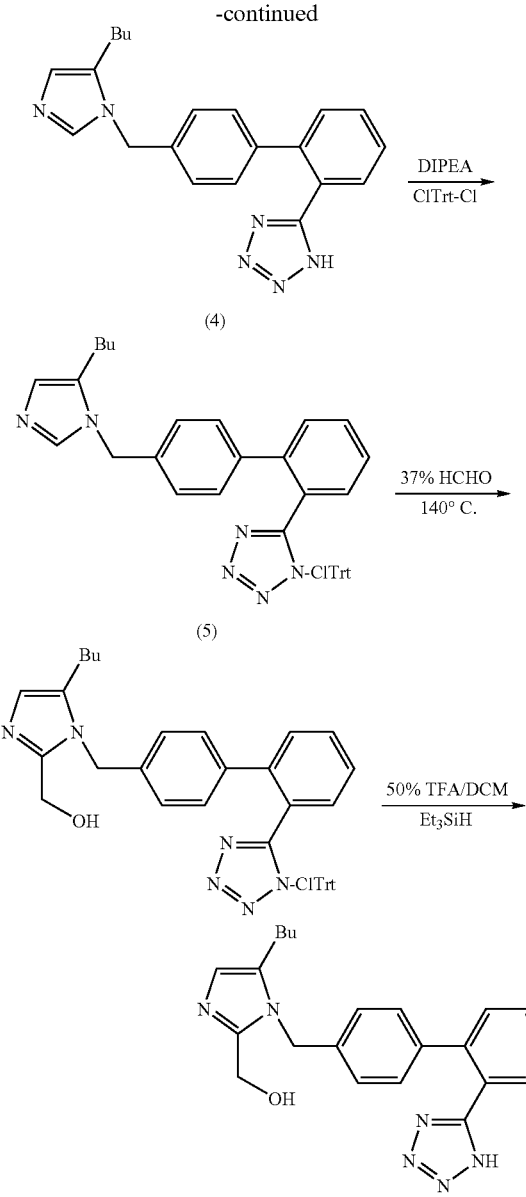

Synthesis of 2: 4(5) butylimidazole (1) (10 g, 80.5 mmol), triethylamine (27.9 ml, 201.25 mmol), triphenylmethyl chloride (25.2 g, 88.5 mmol) and anhydrous dichloromethane (200 ml) were mixed and stirred at room temperature for 1 h. The reaction mixture was washed with 5% NaHCO3 and water, dried over anhydrous sodium sulfate, filtered, concentrated under vacuum and the residue was crystallized from diethyl ether to yield 26.5 g (90%) of a white solid.

Synthesis of 3: A solution of (2) (10 g, 27.2 mmol) and N-(Triphenylmethyl)-5-[4'-(bromomethyl)biphenyl-2-yl] tetrazole (16.6 g, 30 mmol) in dichloromethane (80 ml) was stirred at room temperature for 72 h. The mixture was concentrated under vacuum. Trituration of the crude product with isopropyl ether gave 25 g of (3) as an off-white solid.

Synthesis of 4: To a solution of 50% trifluoroacetic acid in dichlomethane (50 ml) were added the compound (3) (25 g, 29.5 mmol) and triethylsilane (9.4 ml, 59 mmol). The resulting mixture was stirred at room temperature for 1 h concentrated under vacuum. Trituration of the crude product with diethyl ether gave 8 g of (4) (75%) as an off-white solid. The purification of the products of alkylation can take place by the use of preparative RP-HPLC.

Synthesis of 5: To a solution of (4) (8 g, 22.3 mmol) in dichlomethane (60 ml) were added N,N' diisopropylethylamine (9.5 ml, 55.8 mmol) and 2-chloro triphenylmethyl chloride (7.7 g, 24.5 mmol). The mixture was stirred at room temperature for 1 h and then washed with 5% citric acid and water, dried over anhydrous sodium sulfate, filtered and concentrated under vacuum. Column chromatography (elution: 97.5:2.5 chloroform/methanol) provided 9.6 g (68%) of (5) as an off-white solid.

Synthesis 6: A mixture of (5) (0.6 g, 0.94 mmol), N,N' diisopropylethylamine (0.4 ml, 2.35 mmol) and formaldehyde solution (37%, 0.25 ml, 3.3 mmol) was heated in a Curtious tube at 95° C. for 16 h. After cooling the reaction was partitioned between water and chloroform and the aqueous phase extracted with chloroform. The organic extracts were washed with 5% citric acid and water, dried over anhydrous sodium sulphate, filtered, and the solvent removed in vacuo leaving a yellow oil. Column chromatography (elution: 96.5: 3.5 chloroform/methanol) provided 250 mg (40%) of (6) as an off-white solid.

Synthesis of 7: To a solution of 50% trifluoroacetic acid in dichlomethane (1 ml) were added the compound (6) (250 mg, 0.37 mmol) and triethylsilane (0.06 ml, 0.37 mmol). The resulting mixture was stirred at room temperature for 1 h and concentrated under vacuum leaving a yellow oil which was crystallized from diethyl ether to yield 115 mg (80%) of (7) as an off-white solid.

2. Synthesis of the Dialkylated Derivative 4

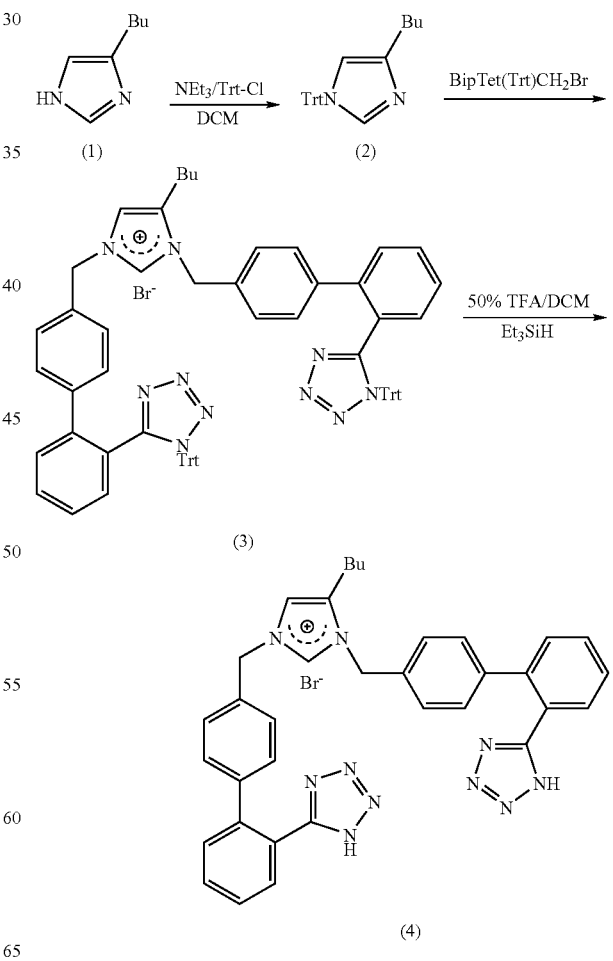

Synthesis of 2: 4(5) butylimidazole (1) (10 g, 80.5 mmol), triethylamine (27.9 ml, 201.25 mmol), triphenylmethyl chloride (25.2 g, 88.5 mmol) and anhydrous dichlomethane (200 ml) were mixed and stirred at room temperature for 1 h. The reaction mixture was washed with 5% NaHCO3 and water, dried over anhydrous sodium sulfate, filtered, concentrated under vacuum and the residue was crystallized from diethyl ether to yield 26.5 g (90%) of a white solid.

Synthesis of 3: A solution of (2) (10 g, 27.2 mmol) and N-(Triphenylmethyl)-5-[4'-(bromomethyl)biphenyl-2-yl] tetrazole (33.2 g, 60 mmol) in dichloromethane (120 ml) was stirred at room temperature. After 72 h it can be observed the formation of the dialkylated product (3). The monoalkylated product turns into the dialkylated product during the reaction of alkylation. The mixture was concentrated under vacuum. Trituration of the crude product with isopropyl ether gave 25 g of (3) as an off-white solid.

Synthesis of 4: To a solution of 50% trifluoroacetic acid in dichlomethane (60 ml) were added the compound (3) (25 g, 23.2 mmol) and triethylsilane (10 ml, 61 mmol). The resulting mixture was stirred at room temperature for 1 h concentrated under vacuum. Trituration of the crude product with diethyl ether gave 10.2 g (74%) of the deprotected dialkylated product (4) as an off-white solid. The purification of the products of alkylation can take place by the use of preparative RP-HPLC.

3. Synthesis of Urocanic Acid Based AT1 Receptor Antagonists

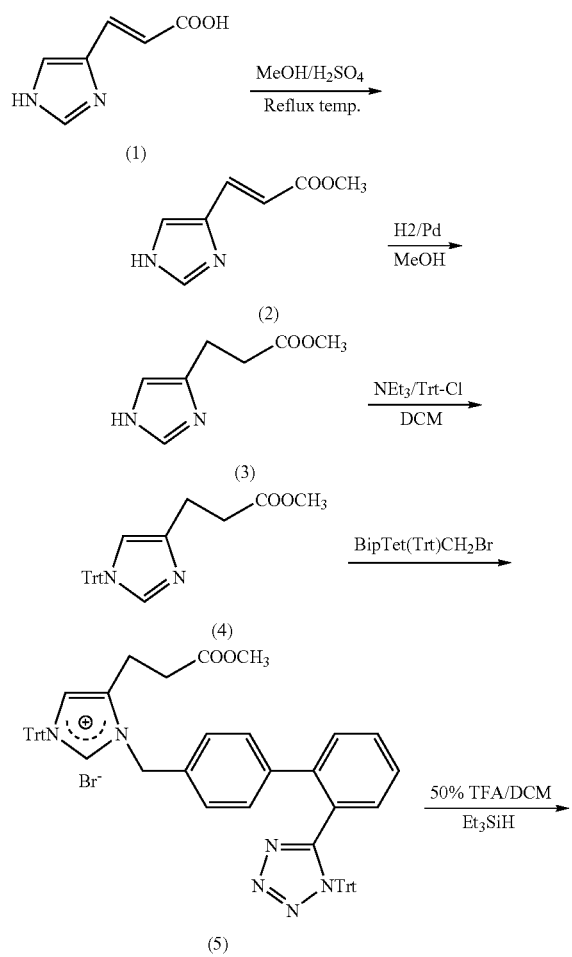

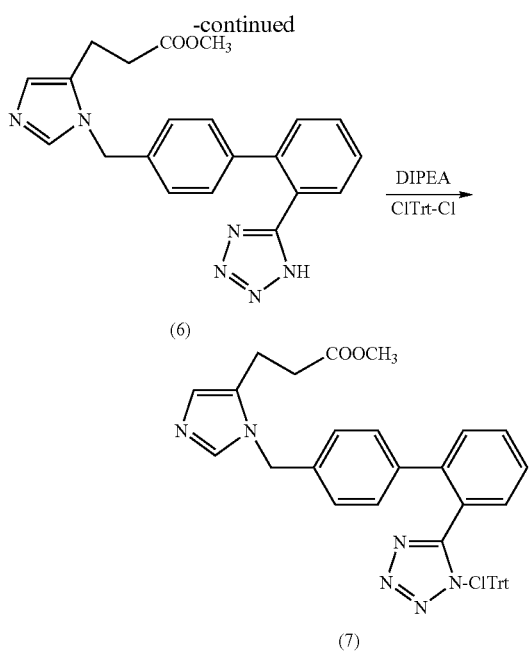

Synthesis of URO-1: Urocanic acid (1) (10 g, 72.4 mmol), Methanol (50 ml, 1.24 mol) and concentrated Sulphuric acid (2 ml, 36.7 mmol) were mixed and stirred at reflux temperature for 24 h. The reaction mixture was dissolved in Ethyl Acetate and washed with 5% NaHCO3 and water, dried over anhydrous sodium sulfate, filtered, concentrated under vacuum and the residue was crystallized from Petroleum ether to yield 9.6 g (92%) of a white solid.

Synthesis of URO-2: A solution of (2) (5 g, 32.9 mmol) was dissolved in methanol and 1.2 g of the catalyst Pd on carbon were added. The mixture was placed in the hydrogenation device for 24 h in order the reduction to take place. The mixture was filtered and concentrated under vacuum and 4.8 g (95%) of a yellow oil were provided.

Synthesis of URO-3: Oil (3) (3.9 g, 25.8 mmol), triethylamine (10.6 ml, 75.6 mmol), triphenylmethyl chloride (7.1 g, 25.8 mmol) were dissolved in dichloromethane (50 ml) and stirred at room temperature for 1 h. The reaction mixture was dissolved in Ethyl Acetate and washed with 5% NaHCO3 and water, dried over anhydrous sodium sulfate, filtered, concentrated under vacuum and the residue was crystallized from diisopropyl ether to yield 9.2 g (90%) of a white creamy solid (4).

Synthesis of URO-4: A solution of (4) (5 g, 12.6 mmol) and N-(Triphenylmethyl)-5-[4'-(bromomethyl)biphenyl-2-yl] tetrazole (7.03 g, 12.6 mmol) in dichloromethane (20 ml) was stirred at room temperature for 72 h under nitrogen. The mixture was concentrated under vacuum. Trituration of the crude product with diisopropyl ether gave 7.5 g (59%) of the trifluoroacetic salt (5) as an off-white solid. Column chromatography (elution: 97.5:2.5 chloroform/methanol) provided 5.6 g (50%) of (5)

Synthesis of URO-5: To a solution of 50% trifluoroacetic acid in dichloromethane (30 ml) were added the compound (5) (3 g, 3.5 mmol) and triethylsilane (3 ml, 19.6 mmol). The resulting mixture was stirred at room temperature for 1 h and concentrated under vacuum. Trituration of the crude product with diethyl ether gave 0.88 g of (6) (65%) as a yellow oil. Column chromatography (elution: 96.5:3.5 chloroform/methanol) provided 650 mg (47%) of (6) as a yellow oil were added N,N' diisopropylethylamine (1.5 ml, 9 mmol) and 2-chloro triphenylmethyl chloride (0.5 g, 1.8 mmol). The mixture was stirred at room temperature for 1 h and then washed with 5% citric acid and water, dried over anhydrous sodium sulfate, filtered and concentrated under vacuum. Column chromatography (elution 97.5:2.5 chloroform/methanol) provided 0.82 g (68%) of (7) as an off-white solid.

4. Synthesis of the Dialkylated Derivative of URO-5

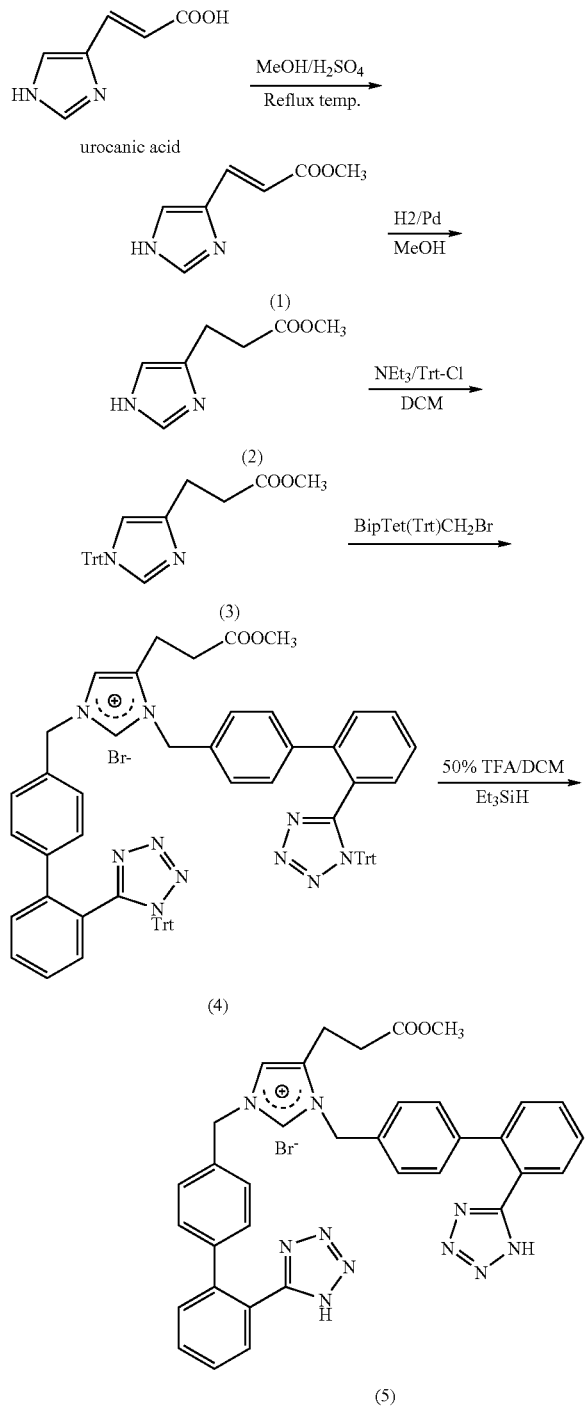

Synthesis of URO-1: Urocanic acid (10 g, 72.4 mmol), Methanol (50 ml, 1.24 mol) and concentrated Sulphuric acid (2 ml, 36.7 mmol) were mixed and stirred at reflux temperature for 24 h. The reaction mixture was dissolved in Ethyl Acetate and washed with 5% NaHCO3 and water, dried over anhydrous sodium sulfate, filtered, concentrated under vacuum and the residue was crystallized from Petroleum ether to yield 9.6 g (92%) of a white solid.

Synthesis of URO-2: A solution of (2) (5 g, 32.9 mmol) was dissolved in methanol and 1.2 g of the catalyst Pd on carbon were added. The mixture was placed in the hydrogenation device for 24 h in order the reduction to take place. The mixture was filtered and concentrated under vacuum and 4.8 g (95%) of a yellow oil were provided. Synthesis of URO-3: Oil (3) (3.9 g, 25.8 mmol), triethylamine (10.6 ml, 75.6 mmol), triphenylmethyl chloride (7.1 g, 25.8 mmol) were dissolved in dichloromethane (50 ml) and stirred at room temperature for 1 h. The reaction mixture was dissolved in Ethyl Acetate and washed with 5% NaHCO3 and water, dried over anhydrous sodium sulfate, filtered, concentrated under vacuum and the residue was crystallized from diisopropyl ether to yield 9.2 g (90%) of a white creamy solid (4).

Synthesis of the Dialkylated derivative of DURO-4: A solution of (4) (5 g, 12.6 mmol) and N-(Triphenylmethyl)-5-[4'-(bromomethyl)biphenyl-2-yl]tetrazole (14.06 g, 25.2 mmol) in dichloromethane (35 ml) was stirred at room temperature. After 72 h it can be observed the formation of the dialkylated product (5). The monoalkylated product turns into the dialkylated product during the reaction of alkylation. The mixture was concentrated under vacuum. Trituration of the crude product with diisopropyl ether gave 7.8 g (56%) of (5) as an yellow solid. Column chromatography (elution: 97.5:2.5 chloroform/methanol) provided 6.9 g (50%) of (5)

Synthesis of the Dialkylated derivative of DURO-5: To a solution of 50% trifluoroacetic acid in dichloromethane (45 ml) were added the compound (5) (4 g, 3.6 mmol) and triethylsilane (4 ml, 26 mmol). The resulting mixture was stirred at room temperature for 1 h and concentrated under vacuum. Trituration of the crude product with diethyl ether gave 1.7 g of (6) (75%) as an off-yellow solid. The purification of the products of alkylation can take place by the use of preparative RP-HPLC.

Novel Synthetic Methods for Starting Materials

1. Synthesis of 4(5)-Butyl imidazole (3): The method initially chosen for the synthesis of 4(5)-butyl imidazole is summarized in Scheme 6. Hexanal (1) is a-brominated using polymer-supported bromide and the bromoaldehyde (2) obtained used without further purification.

This brominating reagent is moderately expensive but does avoid the often messy work-up associated with the use of bromine. Bromoaldehyde (2) is stable and easy to purify upon distillation. The use of purified bromoaldehyde (2) in the cyclocondensation reaction with formamidine acetate in liquid ammonia in an autoclive provides the required imidazole (3). As it stands, these two initial steps provide an acceptable route on any significant scale.

Scheme 6

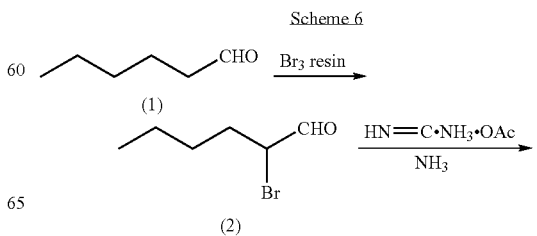

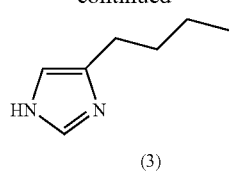

(3)

Other Imidazole Derivatives

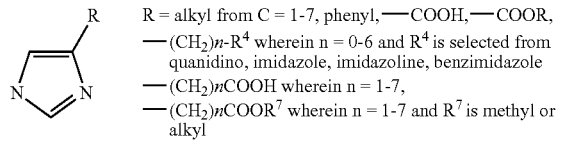

R = alkyl from C = 1-7, phenyl, —COOH, —COOR,
—(CH$_2$)$_n$-R$^4$ wherein n = 0-6 and R$^4$ is selected from quanidino, imidazole, imidazoline, benzimidazole
—(CH$_2$)$_n$COOH wherein n = 1-7,
—(CH$_2$)$_n$COOR$^7$ wherein n = 1-7 and R$^7$ is methyl or alkyl An alternative method for the preparation of 4(5)-Butyl imidazole, utilizes commercially available 4(5)-formyl imidazole as starting material. The butyl group can be introduced into the 5-position by a simple witting/hydrogenation protocol. The 4(5) formyl imidazole can be obtained by mild MnO$_2$ oxidation of 4(5)-hydroxylmethyl imidazole easily synthesized using fructose as starting material (Scheme 7).

Scheme 7

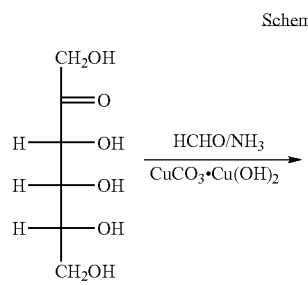

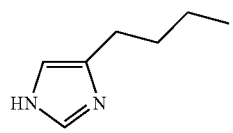

3. Synthesis of N-Tetrazolylbiphenyl substituent (7): The requisite benzyl halide can be prepared by two methods. Treatment of nitrile (4) with trimethyltin azide yields the stannyl tetrazole derivative (5). This is routinely converted to the trityl derivative (6), which is brominated with N-bromosuccinimide yielding halide (7) (Scheme 8).

Scheme 8

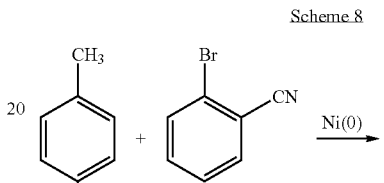

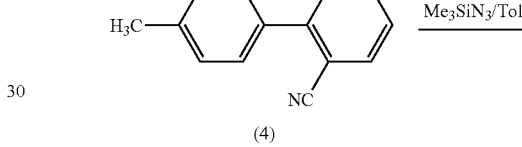

(4)

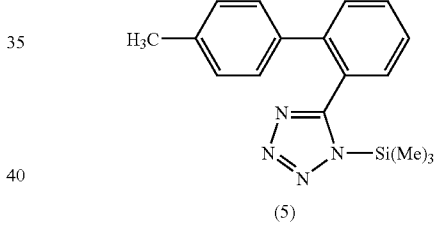

(5)

(6)

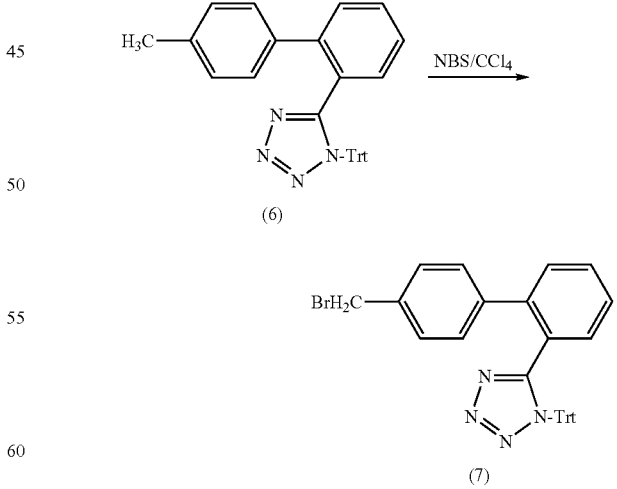

(7)

Alternatively, p-toluol chloride (8) is converted to amide (9) and treated with TMSN3/PPh3/DEAD to yield the protected tetrazole (10). Conversion of (10) to (7) is as previously described (Scheme 9).

Scheme 9
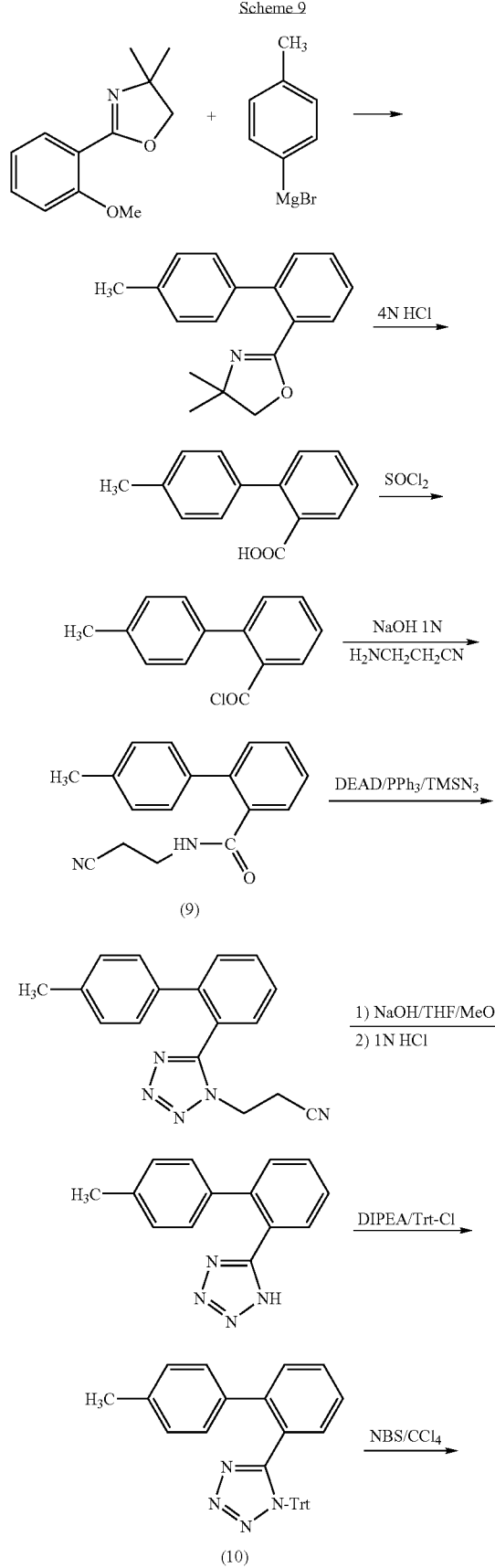
(9)
(10)
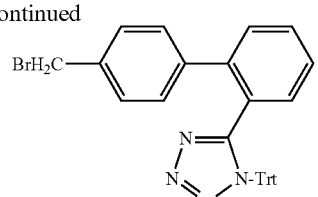
(7)
Other N-Tetrazoyl biphenyl derivatives
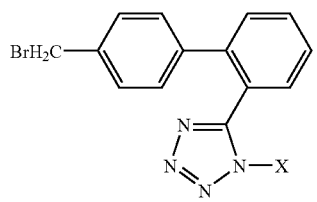
X = Trt, Cltr, Trt derivatives, Bzl, —CH(Ph)$_2$, —CCl(Ph)$_2$
(4)
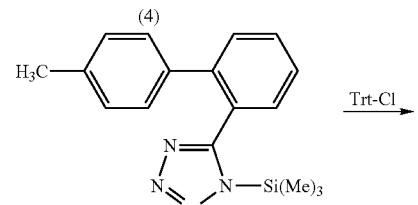
(5)
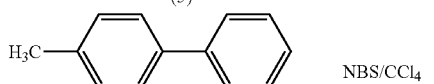
(6)
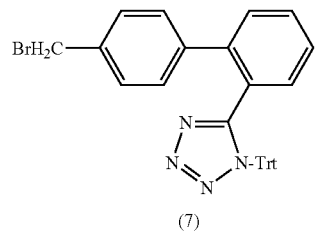
(7)
In Vivo and Vitro Testing
The applicant has also established an in vivo assay using anesthetized rabbits in [Onassis 30 Cardiac Institute] which allows us to estimate relative potencies. This allows the most active substances to be selected for further evaluation.

The assay is a routine assay and constitutes a convenient method to measure activities of AII antagonists. Thus, we have an estimation of in vivo activity which allows us to further evaluate in other assays (e.g in vitro assays) the most active and suitable compounds for further evaluation. In vitro assays were carried out for the most potent in vivo compounds (all bearing a hydroxymethyl group, which is known to optimize affinity and activity). Compounds without the —$CH_2OH$ group were less active in vivo and were not tested for in vitro activity.

Material and Methods for Bioassays

In vivo experiments: Adult normotensive male New Zealand White rabbits weighing between 2.5 and 3.3 kg were used in the study following previously described methods.[46,47] In brief, animals were anesthetized by pentobarbitone (30 mg/kg), intubated and mechanically ventilated with 100% oxygen using a respirator for small animals (MD Industries, Mobile, Ala., USA). The tidal volume was 15 ml and the rate was adjusted to keep blood gases within normal rage. Two polyethylene catheters were inserted, one in the carotid artery for continuous blood pressure monitoring via a transducer attached to a multichannel recorder (Nihon-Kohden, Model 6000, Japan) and the other one in the jugular vein for the administrations of solution made by diluting Angiotensin II (AII) (Hypertensin, CIBA) in 5% dextrose at final concentration of 5 g/ml. Based on previous testing with this rabbit preparation submaximal angiotensin II-dependent hypertension was induced by infusing Angiotensin via a syringe pump (Harvard Apparatus Pump 22, Harvard Apparatus, Natick. Mass., USA) at a constant rate of 0.2 ml/min (1 g/min). Each compound including Losartan was initially dissolved with 0.05 ml of DMSO and then diluted in Dextrose 5% at a final concentration of 2 mg/mL. Five minutes after the establishment of hypertension, two cumulative IV boluses of each compound (2 and 3.5 mol) were given via an ear vein 20 minutes apart. The blood pressure was monitored for 20 minutes after the second bolus and then angiotensin infusion was halted and blood pressure was recorded for an additional period of 20 minutes until the end of the experiment. Boluses of the same dose of Losartan, as positive control, were used in the same experimental model.

In vitro binding experiments: The binding buffer solution comprised 20 nM Tris-HCl, 100 mM NaCl, 5 mM $MgCl2$ and was adjusted to pH=7.4. For the binding studies in the buffer was added 0.1% BSA. The buffers were stored at 4° C. between experiments. Five drug concentrations for the experiments ranged between $10^{-5}$-$10^{-9}$ in ascending power of ten were used and run at triplicates. All drugs were DMSO soluble and when diluted the DMSO concentration did not exceed 1% v/v. The radioligand used for the experiments was [125I] Sar[1], Ile[8]-Angiotensin II, a non specific peptide appropriate for both AT1 and AT2 receptors. A constant concentration of radioligand of 0.1 nM (40000 cpm) was maintained throughout. The total binding is defined as the binding in the absence of competitive compounds. Non-specific binding, in the presence of $10^{-5}$ M Losartan was about 300 cpm. Two kinds of membranes were used for the binding experiments. Membranes containing human AT1 purchased from PerkinElmer Life Sciences, Inc., Boston, Mass., USA and membranes containing either AT1 or AT2 receptor kindly provided by Prof. A. Balmforth, Biomedical Sciences, University of Leeds 23.5 μg of membrane protein was used in each binding assay. Binding assay comprised: 25 L radioligand, 25 L test compound or buffer and 50 L membrane sample. Incubations were carried out at room temperature for at least 1.5 hr. The samples were harvested using a Brandel Cell Harvester on GF/B filters pre-soaked in 1% v/v polyethylimine and washed with chilled binding. The radioactivity retained on the filters was determined on a Packard Rias Star 5405 gamma counter. Binding assays with intact cells were carried out in a similar manner to that given above except that the buffer used was made isotonic by incubation of 150 mM NaCl. 105 cells in 50 l buffer replaced the use of membranes. Washing of filters was also carried out using isotonic buffer.

2. Biological Methods

In Vivo Studies.

The antihypertensive effect and the degree of potency of these compounds were tested in a preparation of anesthetized rabbits made hypertensive by AII infusion. All compounds possessed a dose-dependent AII antagonistic effect at the doses of 2 and 3.5 mol. in a potency order 22, 20, 15, 18, 23, 21, 30, 29.

Compounds are grouped for their in vivo potency as follows: Compounds 22 (free tetrazole), 20 (tetrazole trityl protection), 25 (tetrazole benzyl protection) with hydroxymethylene group at position 4 are the most potent antihypertensive agents in this assay. Their in vivo potency in the order 20>25 indicates a possible deprotection order to the free tetrazole in the in vivo environment which accounts for the observed difference in potency. The chlorotrityl group is an acid sensitive group easily removed in acid environment (Barlos et al[34-37]), while benzyl group is a more stable protecting group which also can be cleaved, albeit with more difficulty, to the free tetrazole in the chemical and enzymic environment of the in vivo assay. Compound 18 (tetrazole chlorotrityl protection without the hydroxymethyl group at position 4) is less potent compared to 20 and 25 due to the lack of the hydroxymethyl group, which in Losartan is metabolized to carboxylate, contributing to higher potency. Compounds 23 (methyl group instead of butyl, free tetrazole) and 21 (methyl group, tetrazole chlorotrityl protection) with hydroxymethyl at position 2 are less potent, indicating that the length of the alkyl group (butyl vs methyl) plays an important role for maximizing activity. Compounds 30 (fused benzimidazole, free tetrazole) and 21 (fused benzimidazole, tetrazole chlorotrityl protection) with hydroxymethyl group are the least active, indicating that a rich electron imidazole ring through the electron donating butyl group and its inductive effect, rather than a fused benzimidazole moiety, is required for higher affinity and activity.

In Vitro Binding Studies.

From the in vivo studies, it appeared that analogues 22 and 20 are the most promising for further studies. The only difference between the two molecules is that 22 lacks the protective Cltr group in its structure. Binding experiments using two different sources of membrane preparations containing the AT1 receptor, one membrane preparation containing AT2 receptors and cell cultures were performed in order to check the specificity of the molecules under investigation and compare their binding effects with their activity observed in vivo. The experiments in membranes containing AT1 receptors and cell cultures were repeated on three occasions and using triplicate determinations showed identical results. Compound 22 was found to have high affinity for the AT1 receptor having only ~3-fold lower affinity than that of Losartan ($IC_{50}$ values of 53.8±6.4 nM and 16.4±1.6 nM respectively). Compound 20 showed a much reduced affinity for the AT1 receptor ($I_{C50}$ value of ~10 M). This may be attributed to the lipophilic character of 20 due to the bulky chlorotrityl moiety. The experiments were performed in DMSO solution, and thus 20 may not distribute extensively in the barrier of the aqueous environments before it enters the membrane. In order to confirm that these molecules (like Losartan) have no binding affinity to the AT2 receptor, experiments were performed in membrane bilayers containing only this receptor. Preliminary experiments indicate that none of the new derivatives have any competition for [$^{125}$I]Sar$^1$, Ile$^8$-Angiotensin II binding at AT2 receptors. Therefore, these molecules apparently have similar binding and biological properties as the prototype Losartan.

Transdermal Administration

Conscious rabbits were made hypertensive by angiotensin II infusion. A mixture of 1 5 mgr of our lipophilic angiotensin II receptor blocker compound 20 (or its dialkylated counterpart) with vaseline was applied on bare skin. Blood pressure was lowered by 20 mmHg for two hours.

NMR and Computational Analysis Methods
Description for Selected Compounds

Assignment and conformational properties of 22. The peak assignment of 1H NMR spectra of the most active synthetic analog synthesized in our studies 22 was achieved by combining 1D 1H NMR integral results along with those obtained using 2D DQF-COSY and ROESY experiments. The ROEs, which govern the conformational properties of 22, can be summarized to: H7-H1 1, H6-H1 1 and H7-H13/17. Lack of the ROE between H8-H10 with the aromatic rings of the biphenyl system implies that the butyl chain of 22 is not in a spatial vicinity with the ring of the biphenyl system as has been observed with Losartan. Random conformers for 22 were generated using Monte Carlo and Dynamics experiments under constraints. From the several clusters generated only two conformers were consistent with NOE data. The two conformers differ only in the relationship between the imidazole-tetrazole orientation. In the first conformer with the lower energy the two aromatic rings have an anti relationship, while in the second conformer they are syn.

Superimposition of 22 onto C-terminal segment of Sarmesin. The two conformers were superimposed with the C-terminal segment of Sarmesin using the following matching groups: (i) imidazole ring of 22 with the corresponding imidazole of His$^6$; (ii) n-butyl chain of 22 with Sarmesin's Ile$^5$ carbon chain; (iii) tetrazole of 22 with Sarmesin's isosteric carboxylate of Phe$^8$; (iv) hydroxymethyl group of 22 with phenolic hydroxyl group of Sarmesin's Tyr$^4$ and (v) 22 spacer phenyl ring with sarmesin's pyrrolidine group of Pro$^7$. Interestingly, 22 mimics the -turn formed around Pro$^7$ in Sarmesin like Losartan.$^{29}$ Conformer I showed a better superimposition with RMS of the matching groups being 1.8. This superimposition ability of 22 with Losartan may explain its high biological activity. This model has enabled us to further explore the spatial characteristics of Angiotensin II pharmacophoric groups and to design and synthesize non-peptide Losartan analogues. An important feature for activity is the presence of at least a negative charge provided by a carboxylate group. Indeed, the antihypertensive activity of Losartan is largely due to a long-acting metabolite (EXP 3174), which is produced in vivo as a result of the conversion of the hydroxymethyl to carboxylate, a molecular feature also met in AT1 antagonists of eprosartan and valsartan. Thus, the rationale of the design of the new derivatives was based on the optimization of the mimicry of the butyl chain with the isopropyl group of Ile$^5$ in sarmesin through superimposition studies reported in a previous publication, on the substitution of Butyl at position 4 with alkyl ester or alkyl carboxyl and on dialkylation of the imidazole ring to increase the negative charge. In order to achieve this, the substitution in the imidazole ring was modified and the alkyl chain was positioned in a different topography in relation to the corresponding substituents of the imidazole ring of Losartan.

Conclusion

In conclusion, the present invention provides a new, novel and general method for the synthesis of key 1,5-disubstituted imidazole intermediates, which could be used for the synthesis of imidazole based AII receptor antagonists. Reversal of the butyl and hydroxymethyl substituents in Losartan leads to analogues of high activity. Synthesis is regioselective, facile and high yielding, rendering it a cost effective process. This convenient method allows the ready introduction of alkylating reagents bearing desired pharmacophoric groups which is a useful tool for the design and synthesis of potent substances for diverse pharmaceutical uses. Furthermore, this invention allows the alkylation of other 4(5) substituted imidazoles such as urocanic acid with a carboxyl or ester group at position 5, which is desirable for increasing the negative charge and affinity to the receptor. The invention also provides the dialkylation of 4(5) alkyl imidazoles or 4(5) acid/ester imidazoles or fused benzoimidazoles, further increasing the negative charge required for better affinity. Finally, the invention provides the transformation of all above substances to lipophilic forms required for transdermal administration.

A two step sequence (N-3 tritylation, N-1 alkylation) is provided in this invention for a regioselective, high yielding synthesis of 1,5-disubstituted imidazoles as key intermediates after alkylation with biphenyl or phenyl tetrazole. Suitable protection of tetrazole with Trt, Cl-Trt, benzyl and subsequent hydroxymethylation, provides for lipophilic prodrug substances with high activity of long duration for treating hypertension and cardiovascular diseases through transdermal administration. Also, a simple two step sequence is provided for synthesis of lipophilic 1,3 disubstituted imidazoles for transdermal administration.

Overall, this invention describes novel potent lipophilic non peptide mimetics of angiotensin II, based on 4(5) alkyl imidazoles, urocanic acid or fused benzoimidazoles, in the treatment of hypertension and cardiovascular diseases through transdermal administration.

Various modifications and variations of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in the relevant fields are intended to be covered by the present invention.

REFERENCES

1. Ferrario, C. M. The Renin-Angiotensin System: Importance in Physiology and Pathology. *J. Cardiovasc. Pharmacol.* 1990, 15 (3), 5 1-55.
2. Sealey, J. E.; Laragh, J. H. The Renin-Angiotensin-Aldosteronie System for Normal Regulation of Blood Pressure and Sodium and Potassium Homeostasis. In *Hypertension: Pathophysiology, Diagnosis and Management*; Laragh, J. H., Brenner, B. M., Eds.; Raven Press: New York 1990; pp 1287-13 17.
3. Greenlee, W. J. Hypertension. Treatment by Blockade of the Renin-Angiotensin System. In *Proceedings, XIVth International Symposium on Medicinal Chemistry*; Awouters, F., Eds.; Elsevien: Amsterdam, 1997, pp 97-107.
4. Page, I. H., *Hypertension Mechanisms*; Harcourt Brace Jovanovich: New York, 1987, pp 347-470.
5. Gavras, H.; Gavras, I. Bioactive Peptides in the Treatment of Hypertension and Heart Failure. Bioactive Peptides in Drug Discovery and Design: Medical Aspects, (Eds.) J. Matsoukas and T. Mavromoustakos, Biomedical and Health Research, IOS Press, 1999, 22, 41-50.

6. Gavras, H.; Brunner, H. R.; Turini, G. A.; Kershaw, G. R.; Tifft, C. P.; Cuttelod, S.; Gavras, I.; Vukovich, R. A.; McKinstry, D. N. Anti-hypertensive effect of the oral angiotensin converting-enzyme inhibitor SQ 14225 in man. *N Engl. J. Med.* 1978, 298, 991-995.

7. Corvol, P. New Therapeutic Prospects of Renin-Angiotensin System Inhibition. *Clin. Exp. Hypertens., Part A* 1989, *A*11 (Suppl. 2), 463-470.

8. Berecek, K. H.; King, S. J.; Wu, J. N. *Angiotensin-Converting Enzyme and Converting Enzyme Inhibitors. Cellular and Molecular Biology of the Renin-Angiotensin System*; CRC Press: Boca Raton, Fla., 1993; pp 183-220.

9. Waeber, B.; Nussberger, J.; Brunner, H. R. Angiotensin-Converting-Enzyme Inhibitors in Hypertension. In *Hypertension: Pathophysiology, Diagnosis and Management*; Laragh, J. H., Brenner, B. M., Eds; Raven Press: New York, 1990; pp 2209-2232.

10. (a) Lindgren, B. R.; Andersson, R G. G. Angiotensin-Converting Enzyme Inhibitors and Their Influence on Inflammation, Bronchial Reactivity and Cough. *Med. Toxicol. Adverse Drug Exp.* 1989, 4, 369-380. (b) Ondetti, M. A.; Cushman, D. W. Inhibition of the Renin-Angiotensin System: A New Approach to the Therapy of Hypertension. *J. Med. Chem.* 1981, 24, 355-361.

11. (a) Wexler, R. R.; Greenlee, W. J.; Irvin, J. D.; Goldberg, M. R.; Prendergast, K.; Smith, R. D.; Timmermans, P. B. M. W. M. Nonpeptide Angiotensin II receptor antagonists: the next generation in antihypertensive therapy. *J. Med. Chem.* 1996, 39, 625-655. (b) Timmermans, P. B. M. W. M.; Carini, D. J.; Chiu, A. T.; Duncia, J. V.; Price, W. A., Jr.; Wells, G. J.; Wong, P. C.; Wexler, R. R.; Johnson, A. L. Nonpeptide Angiotensin II Receptor Antagonists. *Am. J. Hypertens.* 1990, 3, 599-604. (c) Levens, N. R.; de Gasparo, M.; Wood, J. M.; Bottari, S. P. Could the Pharmacological Differences Observed Between Angiotensin II Antagonists and Inhibitors of Angiotensin Converting Enzyme be Clinically Beneficial? *Pharmacol. Toxicol.* 1992, 71, 241-249. (d) Timmermans, P. B. M. W. M.; Wong, P. C.; Chiu, A. T.; Herblin, W. F.; Benfield, P.; Carini, D. J.; Lee, R. J.; Wexler, R. R.; Saye, J. A. M.; Smith, R. D. Angiotensin II Receptors and Angiotensin II Receptor Antagonists. *Pharmacol. Rev.* 1993, 45, 205-251. (e) Bottari, S. P.; de Gasparo, M.; Steckelings, U. M.; Levens, N. R. Angiotensin II Receptor Subtypes: Characterization, Signalling Mechanisms, and Possible Physiological Implications. *Front. Neuroendocrinol.* 1993, 14, 123-171.

12. (a) Moore, G.; Smith, J.; Baylis, B.; Matsoukas, J. Design and Pharmacology of Peptide Mimetics. *Adv. Pharmacol.* (San Diego) 1995, 6, 91-141. (b) Giannis, A.; Bubsam, F. Peptidomimetics in Drug Design. *Adv. Drug Res.* 1997, 29, 1-78. (c) Adang, A.; Hermkens, P.; Linders, J.; Ottenheijm, H.; Staveren, C. Case Histories of Peptidomimetics: Progression from Peptides to Drugs. *J. R. Neth. Chem. Soc.* 1994, 113, 63-78.

13. (a) Sasaki, K.; Yamano, Y.; Bardhan, S.; Iwai, N.; Murray, J. J.; Hasegawa, M.; Matsuda, Y.; Inagami, T. Cloning and Expression of a Complementary DNA Encoding a Bovine Adrenal Angiotensin II Type-1 Receptor. *Nature* 1991, 351, 230-233. (b) Murphy, T. J.; Alexander, R. W.; Griendling, K. K.; Runge, m. S.; Bernstein, K. E. Isolation of a cDNA Encoding the Vascular Type-1 Angiotensin II Receptor. *Nature* 1991, 351, 233-236.

14. (a) Duncia, J. V.; Chiu, A. T.; Carini, D. J.; Gregory, G. B.; Johnson, A. L.; Price, W. A.; Wells, G. J.; Wong, P. C.; Calabrese, J. C.; Timmermans, P. B. M. W. M. The Discovery of Potent Nonpeptide Angiotensin II Receptor Antagonists: A New Class of Potent Antihypertensives. *J. Med. Chem.* 1990, 33, 13 12-1329. (b) Carini, D. J.; Duncia, J. V.; Johnson, A. L.; Chiu, A. T.; Price, W. A.; Wong, P. C.; Timmermans, P. B. M. W. M. Nonpeptide Angiotensin II Receptor Antagonists: N-[(Benzyloxy)benzyl] imidazoles and Related Compounds as Potent Antihypertensives. *J. Med. Chem.* 1990, 33, 1330-1336.

15. Carini, D. J.; Duncia, J. V.; Aldrich, P. E.; Chiu, A. T.; Johnson, A. L.; Pierce, M. E.; Price, W. A.; Santella, J. B., III.; Wells, G. J.; Wexler, R. R.; Wong, P. C.; Yoo, S. E.; Timmermans, P. B. M. W. M. Nonpeptide Angiotensin II Receptor Antagonists The Discovery of a Series of N-(Biphenylmethyl)-imidazoles as Potent, Orally Active Antihypertensives. *J. Med. Chem.* 1991, 34, 2525-2547.

16. Duncia, J. V.; Carini, D. J.; Chiu, A. T.; Pierce, M. E.; Price, W. A.; Smith, R. D.; Wells, G. J.; Wong, P. C.; Wexler, R. R.; Johnson, A. L.; Timmermans, P. B. M. W. M. DuP 753 Losartan Potassium (MK-954). *Drugs Future* 1992, 17, 326-331.

17. (a) Ashton, W. T. Nonpeptide Angiotensin II Receptor Antagonists. *Exp. Opin. Invest. Drugs* 1994, 3, 1105-1142. (b) Buhlmayer, P. Angiotensin II Antagonists: Patent Activity since the Discovery of DuP 753. *Curr. Opin. Ther. Pat.* 1992, 2, 1693-1718. (c) Wexler, R. R.; Greenlee, W. J.; Irvin, J. D.; Goldberg, M. R.; Prendergast, K.; Smith, R. D.; Timmermans, P. B. M. W. M. Nonpeptide Angiotensin II Receptor Antagonists: The next Generation in Antihypertensive Therapy. *J. Med. Chem.* 1996, 39, 625-656.

18. Bradbury, R. H.; Allot, C. P.; Dennis, M.; Fisher, E.; Major, J. S.; Masek, B. B.; Oldham, A. A.; Russell, S. T. New nonpeptide Angiotensin II receptor antagonists. 2. Synthesis, biological properties, and structure-activity relationships of 2-alkyl-4-(biphenylylmethoxy) quinoline derivatives. *J Med. Chem.* 1992, 35, 4027-403 8.

19. Masek, B. B.; Merchant, A.; Matthew, J. B. Molecular shape comparison of Angiotensin II receptor antagonists. *J. Med. Chem.* 1993, 36, 1230-123 8.

20. Theodoropoulou, E.; Mavromoustakos, T.; Panagiotopoulos, D.; Matsoukas, J. M.; Smith, J. Superimposition of potent non-peptide AT1 receptor antagonists with Angiotensin II. *Lett. Pept. Sci.* 1996, 3, 209-2 15.

21. Easthope, S. E.; Jarvis, B. Candesartan cilexetil: an update of its use in essential hypertension. *Drugs* 2002, 62(8), 1253-1287.

22. Rabbat, C. G. Irbesartan was renoprotective in patients with type 2 diabetes, hypertension, and microalbuminuria. *ACP J Club.* 2002, 13 6 (3), 82-84.

23. Cheng-Lai, A. Eprosartan: an angiotensin-II receptor antagonist for the management of hypertension. *Heart Dis.* 2002, 4 (1), 54-59.

24. (a) Maillard, M. P.; Rossat, J.; Brunner, H. R.; Burnier, M. Tasosartan, enoltasosartan, and angiotensin II receptor blockade: the confounding role of protein binding. *J Pharmacol Exp Ther.* 2000, 295 (2), 649-654. (b) Rippin, J.; Bain, S. C.; Barnett, A. H. Rationale and design of diabetics exposed to telmisartan and enalapril (DETAIL) study. *J Diabetes Complications.* 2002, 16 (3), 195-200.

25. Brunner, H. R.; Gavras, H. Angiotensin blockade for hypertension: a promise fulfilled. *The Lancet* 2002, 359, 990-992.

26. Polevaya, L.; Mavromoustakos, T.; Zoumboulakis, P.; Crdadolnik, S.; Roumelioti, P.; Giatas, N.; Mutule, I.; Vlahakos, D.; Iliodromitis, E.; Kremastinos, D.; Matsoukas, J.

Synthesis and Study of a Cyclic Angiotensin II Antagonist Analogue Reveals the Role of *-* Interactions in the C-terminal Aromatic Residue for Agonist Activity and its Structure Resemblance with AT1 Non-peptide Antagonists. *Bioorg. Med. Chem.* 2001, 9, 1639-1647.

27. (a) Moore, G. J.; Ganter, R. C.; Matsoukas, J. M.; Hondrelis, J.; Agelis, G.; Barlos, K., Wilkinson, S.; Sandall, J.; Fowler, P. Receptor interactions of the position 4 side chain of angiotensin II analogues: Importance of aromatic ring quadrupole. *J. Mol. Rec.* 1994, 7, 251-256. (b) Turner, R. J.; Matsoukas, J. M.; Moore, G. J. Fluorescence properties of Angiotensin II analogues in receptor-simulating environments: relationship between tyrosinate fluorescence lifetime and biological activity. *Biochim. Biophys. Acta* 1991, 1065, 2 1-28.

28. (a) Matsoukas, J. M.; Agelis, G.; Hondrelis, J.; Yamdagni, R.; Wu, Q.; Ganter, R.; Smith, J.; Moore, D.; Moore, G. J. Synthesis and biological activities of Angiotensin II, Sarilesin and Sarmesin anologues containing Aze or Pip at position 7: conformational properties of [Sar$^1$, Aze$^7$] ANG II determined by nuclear overhauser effect (NOE) enhancement spectroscopy. *J. Med. Chem.* 1993, 36, 904-911. (b) Matsoukas, J. M.; Yamdagni, R.; Moore, G. J. 1H NMR Studies of Sarmesin and [Des$^1$] Sarmesin conformation in dimethyl sulfoxide by Nuclear Overhauser. Effect (NOE) enhancement spectroscopy: folding of the N- and C-terminal domains. *Peptides* 1990, 11, 367-374.

29. Mavromoustakos, T.; Kolocouris, A.; Zervou, M.; Roumelioti, P.; Matsoukas, J.; Weisemann, R. An Effort to Understand the Molecular Basis of Hypertension through the Study of Conformational Analysis of Losartan and Sarmesin Using a Combination of Nuclear Magnetic Resonance Spectroscopy and Theoretical Calculations. *J. Med. Chem.* 1999, 42, 1714-1722.

30. Wahhab, A.; Smith, J. R.; Ganter, R. C.; Moore, D. M.; Hondrelis, J.; Matsoukas, J.; Moore, G. J. Imidazole Based Non-Peptide Angiotensin II Receptor Antagonists. *Arzn.-Forsch./Drug Research* 1993, 43 (I), 11, 1157-1168.

31. Meyers, A. I.; Mihelich, E. D. Oxazolines. XXII. Nucloephilic Aromatic Substitution on Aryl Oxazolines. An Efficient Approach to Unsymmetrically Substituted Biphenyls and o-Alkyl Benzoic Acids. *J. Am. Chem. Soc.* 1975, 97, 7383-7385.

32. Dordor, I. M.; Mellor, J. M. Reaction of Oxazolines with Phosphorus Oxychloride. *Tetrahedron Lett.* 1983, 1437-1440.

33. Duncia, J. V.; Pierce, M. E.; Santella, J. B. Three Synthetic Routes to a Sterically Hindered Tetrazole. A New One-Step Mild Conversion of an Amide into a Tetrazole. *J. Org. Chem.* 1991, 56, 2395-2400.

34. (a) Barlos, K.; Papaioannou, D.; Theodoropoulos, D. Efficient "one-pot" Synthesis of N-trityl Amino Acids. *J. Org. Chem.* 1982, 47, 1324. (b) Athanasopoulos, C.; Balayiannis, G.; Karigiannis, G.; Papaioannou D. A. N-Tritylamino Acids in the Synthesis of Analogs of Bioactive Compounds for Structure-Activity Relationship Studies. *IOS Press* 1999, 22, 137-15 1.

35. Athanassopoulos, P.; Barlos, K.; Gatos, D.; Hatzi, O.; Tzavara, C. Application of 2-Chlorotrityl Chloride in Convergent Peptide Synthesis. *Tetr. Lett.* 1995, 36, 5645-5648.

36. Barlos, K.; Gatos, D. 9-Fluorenylmethyloxycarbonyl/tbutyl-based convergent protein synthesis. *Biopolymers.* 1999, 51 (4), 266-278.

37. Krambovitis, E.; Hatzidakis, G.; Barlos, K. Preparation of MUC-1 oligomers using an improved convergent solid-phase peptide synthesis. *J Biol. Chem.* 1998, 273 (1 8), 10874-10879.

38. Matsoukas, J. M.; Hondrelis, J.; Keramida, M.; Mavromoustakos, T.; Makriyannis, A.; Yamdagni, R.; Wu, Q.; Moore, J. Role of the N-terminal Domain of ANG II and [Sar$^1$] ANGII on Conformation and Activity. *J. Biol. Chem.*, 1994, 269, 5303-53 12.

39. Matsoukas, J. M.; Agelis, G.; Wahhab, A.; Hondrelis, J.; Panagiotopoulos, D.; Yamdagni, R.; Wu, Q.; Mavromoustakos, T.; Maia, H. L. S.; Ganter, R.; Moore, G. J. Differences in Backbone Structure between Angiotensin II Agonists and Type I Antagonists. *J. Med. Chem.* 1995, 38, 4660-4669.

40. Matsoukas, J. M.; Cordopatis, P.; Belte, U.; Goghari, M. H.; Ganter, R. C.; Franklin, K. J.; Moore, G. J. Importance of the N-terminal domain of the type II angiotensin antagonist Sarmesin for receptor blockade. *J. Med. Chem.* 1998, 31, 1418-142 1.

41. Matsoukas, J. M.; Goghari, M. A.; Scanlon, M. N.; Franklin, K. J.; Moore, G. J. Synthesis and biological activities of analogues of angiotensin II and III containing O-methyltyrosine and D-tryptophan. *J. Med. Chem.* 1985, 28, 780-783.

42. (a) Matsoukas, J.; Hondrelis, J.; Agelis, G.; Barlos, K.; Gatos, D.; Ganter, R.; Moore, D.; Moore, G. Novel Synthesis of Cyclic Amidelinked Analogues of Angiotensin II and III. *J. Med. Chem.* 1994, 37, 2958-2969. (b) Vlahakos, D. V.; Matsoukas, J. M.; Ancans, J.; Moore, G. J.; Iliodromitis, E. K.; Marathias, K. P.; Kremastinos, D. Th. Biological Activity of the Novel Cyclic Angiotensin II Analogues [Sar$^1$, Lys$^3$, Glu$^5$] ANG II. *Letters in Peptide Science (LIPS)* 1996, 3, 191-194.

43. Polevaya, L.; Mavromoustakos, T.; Zoumboulakis, P.; Grdadolnik, S. G.; Roumelioti, P.; Giatas, N.; Mutule, I.; Keivish, T.; Vlahakos, D. V.; Iliodromitis, E. K.; Kremastinos, D. T.; Matsoukas, J. Synthesis and study of a cyclic angiotensin II antagonist analogue reveals the role of *-* interactions in the C-terminal aromatic residue for agonist activity and its structure resemblance with AT(1) non-peptide antagonists. *Bioorg Med. Chem.* 2001, 6, 1639-1647.

44. Matsoukas, J.; Ancas, J.; Mavromoustakos, T.; Kolocouris, A.; Roumelioti, P.; Vlahakos, D.; Yamdagni, R.; Wu, Q.; Moore, G. The bioactive conformation of Angiotensin II. The design and synthesis of a potent Angiotensin II cyclic analogue confirms the ring cluster receptor conformation of the hormone. *Bioorg. Med. Chem.* 2000, 8, 1-10.

45. Roumelioti, P.; Polevaya, L.; Mavromoustakos, T.; Zoumboulakis, P.; Giatas, N.; Mutule, I.; Keivish, T.; Zoga, A.; Vlahakos, D. V.; Iliodromitis, E. K.; Kremastinos, D. T.; Matsoukas, J. Design, Synthesis and Biological Evaluation of Cyclic Angiotensin II Analogues with 3,5 Side-Chain Bridges: Role of C-Terminal Aromatic Residue and Ring Cluster for Activity and Implications in the Drug Design of AT1 Non Peptide Antagonists. *Bioorg Med. Chem.,* 2002 12, 2627-2633.

46. Vlahakos, D. V.; Kosmas, E. N.; Dimopoulou, I.; Ikonomou, E.; Jullien, G.; Vassilakos, P.; Marathias, K. P. Association Between Activation of the Renin-Angiotensin System and Secondary Erythrocytosis in Patients With Chronic Obstructive Pulmonary Disease. *Am J Med.* 1999, 106 (2), 158-164.

47. Polevaya, L.; Roumelioti, P.; Mavromoustakos, T.; Zoumpoulakis, P.; Giatas, N.; Mutule, I.; Keivish, T.; Zoga, A.; Vlahakos, D.; Iliodromitis, E.; Kremastinos, D.; Matsoukas, J. Design, synthesis and biological evaluation of cyclic angiotensin II analogues with 3,5 side-chain bridges: Role of C-terminal residue and positions 3,5 for activity. In *Drug*

Discovery and Design: Medical Aspects, Vol. 55, Matsoukas, J., Mavromoustakos, T., Eds.; IOS Press: The Netherlands, 2002; pp 3-12.
48. $^1$H-NMR Studies of [Sar$^1$] Angiotensin II Conformation by Nuclear Overhauser Effect Spectroscopy in the Rotating Frame (ROESY): Clustering of the Aromatic Rings in Dimethylsulfoxide, J. Matsoukas*, G. Bigam, N. Zhou and G. Moore, Peptides, 11, 359-366, (1990).
49. Tyrosinate Flyorescence Life Times for Oxytocin and Vasopressin in Receptor Simulating Environments Relationship to Biological Activity and $^1$H-NMR Data, R. J. Turner, J. M. Matsoukas, G. J. Moore, Bioch. Bioph. Res. Commun., 171, 996-1001, (1990).
50. Influence of Polyfluorination of the Phenylalanine Ring of Angiotensin II on Conformation and Biological Activity, P. R. Bovy, D. P. Getman, J. M. Matsoukas and G. J. Moore, Biochimica et Biophysica Acta, 1079, 23-28, (1991).
51. Receptor Interactions of the Position 4 Side Chains of Angiotensin II Analogues: Importance of Aromatic Ring Quadrupole, G. J. Moore, R. C. Ganter, J. M. Matsoukas, J. Hondrelis, G. Agelis, K. Barlos, S. Wilkinson, J. Sandall and P. Fowler, J. Mol. Rec., 7, 25 1-256, (1994).
52. Advances in Antihypertensive Therapy: Non-Peptide Angiotensin II Receptor Antagonists as Potent Therapeutic Agents, J. Smith, A. Wahhab, J. Hondrelis, R. Ganter, D. Moore, J. M. Matsoukas and G. J. Moore, Letters in Peptide Science (LIPS), 1996, 3, 169-174 (Guest Editor of Special Issue).
53. Design and Synthesis of Thrombin Receptor-Derived Non-Peptide Mimetics Utilizing a piperazine Scallold, K. Alexopoulos, P. Fatseas, E. Melissari, D. Vlahakos, J. Smith, T. Mavromoustakos, M. Saifeddine, G. Moore, M. Hollenberg, J. Matsoukas, Bioorganic and Medicinal Chemistry 1999, 7, 1033-1041.
54. Structural Comparison Between Type I and Type II Antagonists: Possible Implications in the Drug Design of AT1 Antagonists, P. Roumelioti, T. Tselios et al, Bioorg. And Med. Chem. Letters 2000, 10, 1-4.
55. In Hypertension Mechanisms; Harcourt Brace Jovanovich, Page I. H., New York 1987, 347-470.
56. McAreavey D., Robertson, J. I. S., Drugs 1990, 40, 326.
57. Ondetti, M. A., Rubin, A., Cushman D. W., Science 1977, 196, 441.
58. Timmermans P. B. M. W. M., Wong, P. C., Chiu A. T., Herblin W. F., Trends Pharmacol. Sci. 1991, 12, 55-62.
59. Duncia J. V., Chiu A. T., Carini D. J., Gregory, G. B., Johnson A. L., Price W. A., Wells G. J., Wong P. C., Calabrese J. C., Timmermans P. B. M. W. M., J. Med. Chem. 1990, 33, 1312.
60. Duncia J. V., Carini D. J., Chiu A. T., Johnson A. L., Price W. A., Wong P. C., Wexler R. R., Timmermans P. B. M. W. M., Med. Res. Rev. 1992, 12, 149.
61. In Hypertension: Pathophysiology, Diagnosis and Management, Timmermans .B. M. W. M., Carine D. J., Chiu A. T., Duncia J. V., Price W. A., Wells G. J., Wong P. C., Wexter R. R., Johnson A. L., Raven Press: New York, 1990, 235 1-2360.
62. Safety and efficacy of eprosartan, a new angiotensin II receptor blocker, N. H. Shusterman, American Heart Journal, 138, S23 8-S245, (1999).
63. The efficacy and tolerance of one or two daily doses of eprosartan in essential hypertension, Journal of Hypertension, 17, 129-136, (1999).
64. Pharmacokinetics of eprosartan in healthy subjects, patients with hypertension and special population, M. B. Bottorff; D. M. Tenero, Pharmacotherapy, 19, 73S-78S, (1999).
65. Review of eprosartan: A new angiotensin II receptor antagonist: Summary, D. A. Sica, Pharmacotherapy, 19, 108S-109S, (1999).
66. Treatment with the angiotensin II antagonist valsartan in patients with chronic renal failure and hypertension, J. Plum, B. Bunten, R. Nemeth, B. Grabensee, Nephrology Dialysis Transplantation, 14, 25-27, (1999).
67. Effect of valsartan on renal function in patients with hypertension and stable renal insufficiency, H. D. Faulhaber, J. F. Mann, G. Stein, L. Jansa, Current Therapeutic Research—Clinical and Experimental, 60, 170-183, (1999).
68. Influence of the angiotensin II antagonist valsartan on left ventricular hypertrophy in patients with essential hypertension, P. A. Thurmann, P. Kenedi, A. Schmidt, S. Harder, N. Rietbrock, Circulation, 98, 2037-2042, (1998).
69. Valsartan. A review of its pharmacology and therapeutic us in essential hypertension, Markham, K. L. Goa, Drugs, 54, 299-3 11, (1997).
70. Effects of the angiotensin II type 1 receptor blocker candesartan on endothelial function in patients with essential hypertension, L. Ghiadoni, A. Virdis, A. Magagna, S. Taddei, A. Salvetti, Hypertension, 35, 501-506, (2000).
71. Candesartan cilexetil: an angiotensin II receptor blocker, A. Stoukides, H. J. McVoy, A. F. Kaul, Annals of Pharmacology, 33, 1287-1298, (1999).
72. Candesartan: A new generation angiotensin II AT1 receptor blocker: Pharmacology, antihypertensive efficacy, renal function, and renoprotection, P. Morsing, Journal of the American Society of Nephrology, 10, S248-S254, (1999).
73. Candesartan cilexetil: A review of its use in essential hypertension, K. J. McClellan, K. L. Goa, Drugs, 56, 847-869, (1998).
74. Metabolites of the angiotensin II antagonist tasosartan: The importance of a second acidic group, J. W. Ellingboe, M. D. Collini, D. Quagliato, J. Med. Chem., 41, 425 1-4260, (1998).
75. Effects of angiotensin antagonism with tasosartan on regianal and systemic haemodynamics in hypertensive patients, Rheaume, P. H. Waib, Y. Lacourciere, J. Cleroux, Journal of Hypertension, 16, 2085-2089, (1998).
76. Tolerability profile of tasosartan, a long-acting angiotensin II AT1 receptor blocker, in the treatment of patients with essential hypertension, S. Oparil, A. Gradman, V. Papademetriou, M. Weber, Current Therapeutic Research—Clinical and Experimental, 58, 930-943, (1997).
77. Blood pressure control: A review on irbesartan, B. Waeber, European Heart Journal, Supplement, 2, B2-B7, (2000).
78. Safety of irbesartan in the treatment of mild to moderate systemic hypertension, T. A. Simon, R. T. Gelarden, S. A. Freitag, K. B. Kassler-Taub, R. Davies, The American Journal of Cardiology, 82, 179-182, (1998).
79. Irbesartan. A review of its pharmacodynamic and pharmacokinetic properties and therapeutic use in the management of hypertension, J. C. Gillis, A. Markham, Drugs, 54, 885-902, (1997).
80. Clinical overview of irbesartan: Expanding the therapeutic window in hupertension, J. Man in't Veld, Journal of Hypertension, Supplement, 15, S27-S33, (1997).
81. Efficacy and safety of telmisartan, a selective AT 1 receptor antagonist, compared with enalapril in elderly patients with primary hypertension, E. Karlberg, L. E. Lins, K. Hermansson, Journal of Hypertension, 17, 293-302, (1999).

82. The efficacy and safety of telmisartan compared to enalapril in patients with severe hypertension, J. M. Neutel, D. H. G. Smith, P. A. Reilly, International Journal of Clinical Practice, 53, 175-178, (1999).
83. Hypotensive effects of the angiotensin II antagonist telmisartan in conscious chronically—instrumented transgenic rats, J. C. A. Van Meel, N. Redemann, R. M. Haigh, Arzn.-Forsch./Drug Research, 46, 755-759, (1996).
84. An angiotensin converting enzyme inhibitor to identify and treat vasoconstrictor and volume factors in hypertensive patients, H. Gavras, H. R. Brunner, J. H. Laragh, J. E. Sealey, I. Gavras, R. A. Vukovich, N. Engl. J. Med. 291, 817-821, (1974).
85. Angiotensin II inhibition: treatment of congestive cardiac failure in a high-renin hypertension, H. Gavras, A. Flesas, T. J. Ryan, H. R. Brunner, D. P. Faxon, I. Gavras, JAMA, 238, 880-882, (1997).
86. Suppressing sympathetic activation in congestive heart failure. A. J. Manolis, C. Olympios, M. Sifaki, S. Handanis, M. Bresnaban, I. Gavras, H. Gavras, Hypertension, 26, 719-724, (1995).
87. Combined sympathetic suppression and angiotensin converting enzyme inhibition in congestive heart failure, A. J. Manolis, C. Olympios, M. Sifaki, S. Handanis, D. Cokkinos, M. Bresnahan, I. Gavras, H. Gavras, Hypertension, 29 (part 2), 525-530, (1997).
88. Effects of specific inhibitor of the vascular action of vasopressin in humans, H. Gavras, A. B. Ribeiro, O. Kohlmann, M. Saragoca, R. A. Mulinari, I. Gavras, Hypertension, 6 (Suppl 1), 156-160, (1984).
89. Synthesis and some pharmacologic properties of five novel V1 or Z1/V2 antagonists of AVP, B. Lammek, Y. X. Wang, I. Derdowska, R. franco, H. Gavras, Peptides, 10, 1109-1112, (1989).
90. Oral administration of DuP753, a specific angiotensin II receptor antagonist, to normal male volunteers, Y. Christen, B. Waeber, J. Nussberger, M. Porchet, R. m. Borland, R. J. Lee, K. Maggon, L. Shu, P. B. M. W. M. Timmermans, H. R. Brunnear, Circulation, 83, 1333-1342, (1991).
91. Regioselective alkylation in ionic liquids, Martyn J. Earle, Paul B. Mc Cormac and Kenneth R. Seddon, *Chem.*
92. *Commun.* 2245-2246 (1998).

The invention claimed is:
1. A compound of formula I,

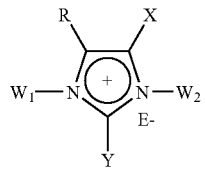

I wherein
R is H, halogen;
X is alkyl, alkenyl, —(CH$_2$)$_v$COOR$^1$ or CH=CH—(CH$_2$)$_v$COOR$^1$, where v is 0 to 10; or R and X are linked so as to form a fused benzimidazole;
R$^1$ is H, alkyl, aralkyl, trityl, halogen, haloalkyl, cycloalkyl, alkenyl, alkynyl, alkoxyalkyl, haloalkoxyalkyl, alkoxy, aryloxy alkoxyalkoxy, cyano, hydroxy, hydroxyalkyl, nitro, tetrazolyl, oxadiazolyl, triazolyl, OCH(CH$_3$)—OCOO-cyclohexyl, cycloanhydride or methyl-5-methyl-[1,3]-dioxolane;
Y is H, CH$_2$O-alkyl, CH$_2$S-alkyl, CH$_2$-halogen, CH$_2$OH, CH$_2$SH, CHO, COOH or halogen;

W$_1$ and W$_2$ are each independently —(CH$_2$)$_n$—K—Z—Z$_1$, where n is 1 to 5;
K is biphenyl or monophenyl;
Z is tetrazolyl or COO—;
Z$_1$ is H, trityl, halotrityl, CH$_2$Ph, COOH, COO-alkyl or CH(Ph)$_2$, wherein each Ph group is optionally substituted by one or more halogens; and
E is an anion;
or a pharmaceutically acceptable salt thereof.
2. A compound according to claim 1:
wherein said compound is of formula M,

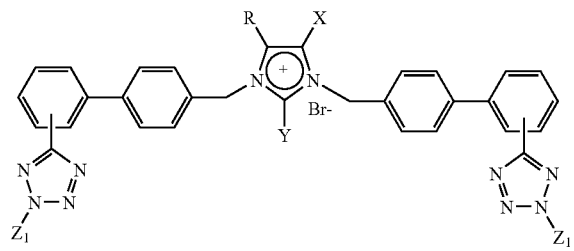

Formula M wherein:
X is CH=CH—COOMe;
R is H or halogen;
Z$_1$ is H, trityl, 2-chlorotrityl or benzyl; and
Y is as defined in claim 1; or
wherein said compound is of formula N,

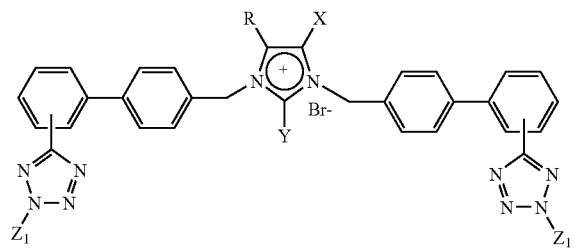

Formula N wherein:
X is CH$_2$CH$_2$COOMe;
R is H or halogen;
Z$_1$ is H, trityl, 2-chlorotrityl or benzyl; and
Y is as defined in claim 1; or
wherein said compound is of formula Q,

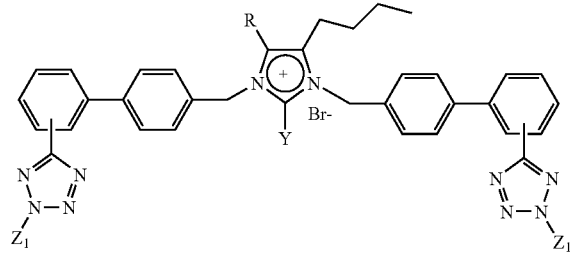

Formula Q wherein:
R is H or halogen;
Z$_1$ is H, trityl, 2-chlorotrityl or benzyl; and
Y is as defined in claim 1.

3. A compound of formula II or formula III,

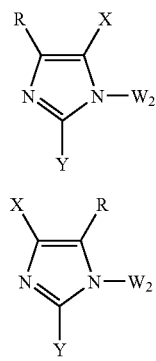

wherein
R is H, halogen;
X is —COOR¹, —CH₂CH₂COOR¹, or CH=CH—COOR¹; or
X is alkyl, when Z₁ is halotrityl, COOH, COO-alkyl, CH₂(C₆H₄-Hal) or CH(Ph)₂, wherein each Ph group is optionally substituted by one or more halogens;
R¹ is H, alkyl, aralkyl, trityl, halogen, haloalkyl, cycloalkyl, alkenyl, alkynyl, alkoxyalkyl, haloalkoxyalkyl, alkoxy, aryloxy, alkoxyalkoxy, cyano, hydroxy, hydroxyalkyl, nitro, tetrazolyl, oxadiazolyl, triazolyl, OCH(CH₃)—OCOO-cyclohexyl, cycloanhydride or methyl-5-methyl-[1,3]-dioxolane;
Y is H, CH₂O-alkyl, CH₂S-alkyl, CH₂-halogen, CH₂OH, CH₂SH, COOH, halogen or CHO;
W₂ is —(CH₂)ₙ—K—Z—Z₁, where n is 1 to 5;
K is biphenyl or monophenyl;
Z is tetrazolyl or COO—; and
Z₁ is H, trityl, halotrityl, CH₂Ph, COOH, COO-alkyl, or CH(Ph)₂, wherein each Ph group is optionally substituted by one or more halogens;
or a pharmaceutically acceptable salt thereof.

4. A compound according to claim 3 wherein W₂ is

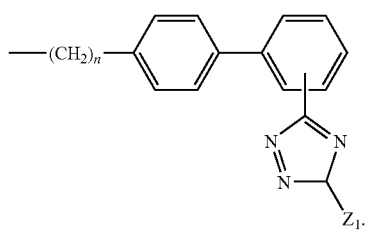

5. A compound according to claim 3 wherein n is 1.
6. A compound according to claim 3 wherein Y is H, CH₂OH, CH₂OMe, CH₂OEt, CH₂SH, CH₂SMe, COOH or halogen or CH₂SEt.
7. A compound according to claim 3 wherein R is H, Br, F, I or Cl.
8. A compound according to claim 3 wherein Z₁ is H, trityl, halotrityl, dibenzyl or benzyl.
9. A compound according to claim 3 wherein X is CH=CH—COOR¹, CH₂CH₂COOR¹ or COOR¹.
10. A compound according to claim 3 wherein R¹ is H, Me or Et.
11. A compound according to claim 3, wherein said compound is of formula A,

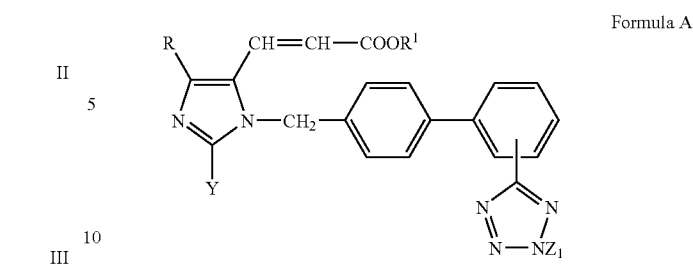

wherein:
R=H or halogen;
R¹=H, CH₃, or —CH₂CH₃;
Z₁=H, chlorotrityl, benzyl or trityl;
Y is as defined in claim 3.

12. A compound according to claim 3, wherein said compound is of formula B,

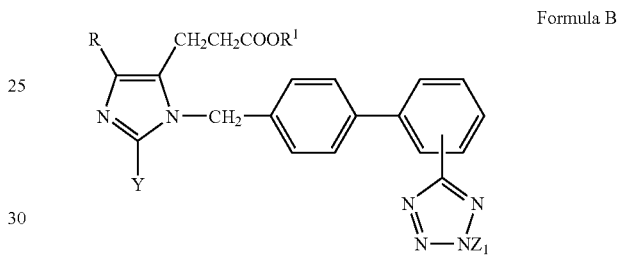

wherein:
R=H or halogen;
R¹=H, CH₃, or —CH₂CH₃;
Z₁=H or trityl;
Y is as defined in claim 3.

13. A pharmaceutical composition comprising a compound as defined in claim 3, or a pharmacuetically acceptable salt thereof, admixed with a pharmaceutically acceptable diluent, excipient or carrier.

14. A pharmaceutical composition according to claim 13 which is in the form of a transdermal patch.

15. A method of treating hypertension or a cardiovascular disorder in a subject, said method comprising administering to the subject a therapeutically effective amount of a compound according to claim 3, or a pharmaceutically acceptable salt thereof.

16. A method according to claim 15 wherein the compound is administered transdermally, subcutaneously or intravenously.

17. A method according to claim 16 wherein the compound is administered transdermally by means of a transdermal patch.

18. A process for preparing a compound of formula I as defined in claim 1, said process comprising the steps of:

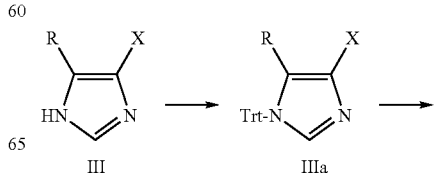

-continued

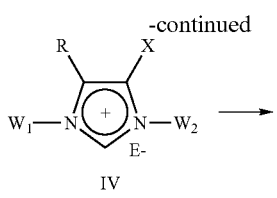

IV → I (i) reacting a compound of formula III with trityl chloride to form a compound of formula IIIa;
(ii) reacting said compound of formula IIIa with Br—$(CH_2)_n$—K—Z—$Z_1$ to form a compound of formula IV;
(iii) converting said compound of formula IV to a compound of formula I.

19. A process according to claim 18 wherein step (ii) comprises reacting said compound of formula IIIa with Br—$(CH_2)_n$—K—Z'—$Z'_1$, wherein Z' is tetrazoyl and $Z'_1$ is trityl, chlorotrityl, benzyl or $CH(Ph)_2$, to form a compound of formula IVa,

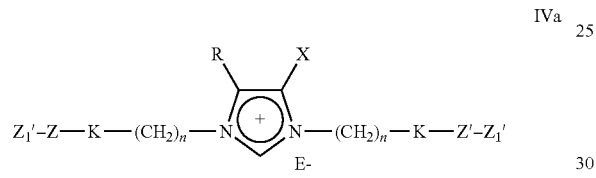

IVa and converting said compound of formula IVa to a compound of formula I.

20. A process according to claim 19 wherein $Z'_1$ is trityl or benzyl.

21. A process according to claim 18 wherein step (ii) is carried out in the presence of potassium carbonate, and the ratio of Br—$(CH_2)_2$—K—Z'—$Z'_1$ to compound IIIa is at least 3:1.

22. A process according to claim 18 wherein step (iii) comprises the steps of:

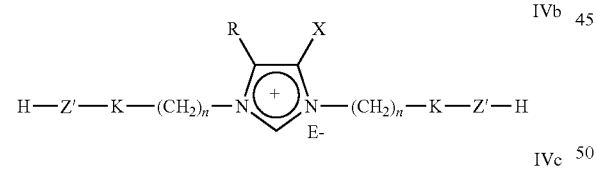

IVb

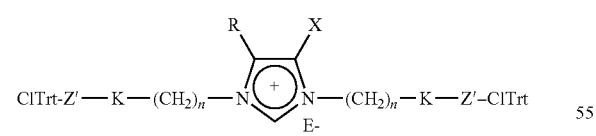

IVc (iii)(a) converting said compound of formula IVa to a compound of formula IVb;
(iii)(b) treating said compound of formula IVb with 2-chlorotrityl chloride to form a compound of formula IVc;
(iii)(c) converting said compound of formula IVc to a compound of formula I.

23. A process according to claim 22 wherein step (iii)(c) comprises treating said compound of formula IVc with formaldehyde to form a compound of formula I, wherein Y is $CH_2OH$.

24. A process for preparing a compound of formula II as defined in claim 3, said process comprising the steps of:

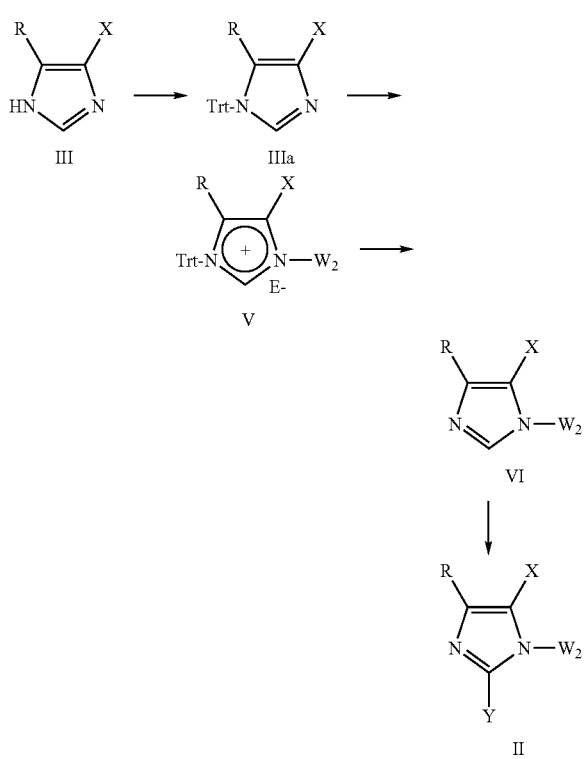

(i) reacting a compound of formula III with trityl chloride to form a compound of formula IIIa:
(ii) reacting said compound of formula IIIa with Br—$(CH_2)_n$—K—Z—$Z_1$ to form a compound of formula V;
(iii) converting said compound of formula V to a compound of formula VI;
(iv) converting said compound of formula VI to a compound of formula II.

25. A process according to claim 24 wherein step (ii) comprises reacting said compound of formula IIIa with Br—$(CH_2)_n$—K—Z'—$Z'_1$, wherein Z' is tetrazoyl and $Z'_1$ is trityl, chlorotrityl, benzyl or $CH(Ph)_2$, to form a compound of formula Va,

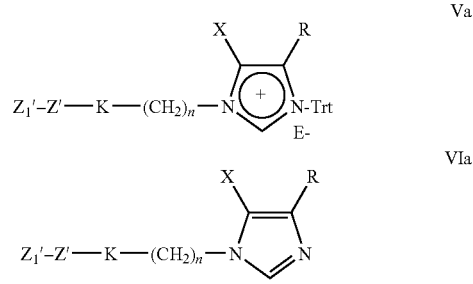

Va

VIa and converting said compound of formula Va to a compound of formula VIa, and converting said compound of formula VI to a compound of formula II.

26. A process according to claim 25 wherein step (iv) comprises the steps of:

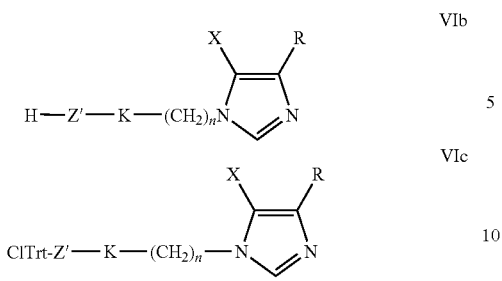

(iv)(a) converting said compound of formula VIa to a compound of formula VIb;
(iv)(b) treating said compound of formula VIb with 2-chlorotrityl chloride to form a compound of formula VIc;
(iv)(c) converting said compound of formula VIc to a compound of formula II.

27. A process according to claim 26 wherein step (iv)(c) comprises treating said compound of formula VIc with formaldehyde to form a compound of formula I, wherein Y is $CH_2OH$.

28. A process according to claim 24 wherein steps (ii) and (iii) are carried out in a one-pot procedure.

* * * * *

UNITED STATES PATENT AND TRADEMARK OFFICE
CERTIFICATE OF CORRECTION

PATENT NO.        : 8,563,586 B2
APPLICATION NO.   : 12/601402
DATED             : October 22, 2013
INVENTOR(S)       : John Matsoukas et al.

It is certified that error appears in the above-identified patent and that said Letters Patent is hereby corrected as shown below:

In the Claims

In column 77, claim 4, replace entire formula with the following formula:

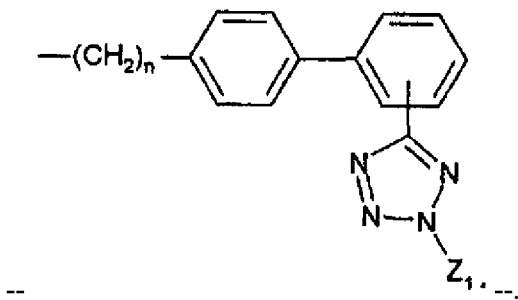

In column 79, claim 19, line 29, formula IVa, replace "$Z_1'$-Z-K-$(CH_2)_n$" with --$Z_1'$-Z'-K-$(CH_2)_n$--.

In column 79, claim 21, line 37, after "according to claim" replace "18" with --19--.

In column 79, claim 21, line 39, after "ratio of Br-" replace "$(CH_2)_2$" with --$(CH_2)_n$--.

Signed and Sealed this
Twenty-third Day of September, 2014

Michelle K. Lee
*Deputy Director of the United States Patent and Trademark Office*

UNITED STATES PATENT AND TRADEMARK OFFICE
CERTIFICATE OF CORRECTION

PATENT NO.       : 8,563,586 B2
APPLICATION NO.  : 12/601402
DATED            : October 22, 2013
INVENTOR(S)      : Matsoukas et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 824 days.

Signed and Sealed this

Fifteenth Day of September, 2015

Michelle K. Lee
*Director of the United States Patent and Trademark Office*